US012629358B2

(12) United States Patent
Li et al.

(10) Patent No.: US 12,629,358 B2
(45) Date of Patent: May 19, 2026

(54) COMPOUND USED AS RET KINASE INHIBITOR AND APPLICATION THEREOF

(71) Applicant: TYK MEDICINES, INC., Huzhou (CN)

(72) Inventors: Jun Li, Huzhou (CN); Maolin Zheng, Huzhou (CN); Chengshan Niu, Huzhou (CN); Apeng Liang, Huzhou (CN); Yusheng Wu, Huzhou (CN)

(73) Assignee: TYK MEDICINES, INC., Huzhou (CN)

( * ) Notice: Subject to any disclaimer, the term of this patent is extended or adjusted under 35 U.S.C. 154(b) by 922 days.

(21) Appl. No.: 17/613,311

(22) PCT Filed: May 20, 2020

(86) PCT No.: PCT/CN2020/091425

§ 371 (c)(1),
(2) Date: Nov. 22, 2021

(87) PCT Pub. No.: WO2020/233641

PCT Pub. Date: Nov. 26, 2020

(65) Prior Publication Data

US 2022/0233513 A1 Jul. 28, 2022

(30) Foreign Application Priority Data

May 20, 2019 (CN) ......................... 201910417078.6

(51) Int. Cl.

| | |
|---|---|
| ***A61K 31/444*** | (2006.01) |
| ***A61K 31/4355*** | (2006.01) |
| ***A61K 31/437*** | (2006.01) |
| ***A61K 31/4725*** | (2006.01) |
| ***A61K 31/497*** | (2006.01) |
| ***A61K 31/4985*** | (2006.01) |
| ***A61K 31/506*** | (2006.01) |
| ***A61K 31/519*** | (2006.01) |

(52) U.S. Cl.

CPC ........ *A61K 31/444* (2013.01); *A61K 31/4355* (2013.01); *A61K 31/437* (2013.01); *A61K 31/4725* (2013.01); *A61K 31/497* (2013.01); *A61K 31/4985* (2013.01); *A61K 31/506* (2013.01); *A61K 31/519* (2013.01)

(58) Field of Classification Search

CPC .............. A61K 31/444; A61K 31/4355; A61K 31/437; A61K 31/4725; A61K 31/497; A61K 31/4985; A61K 31/506; A61K 31/519

See application file for complete search history.

(56) References Cited

U.S. PATENT DOCUMENTS

2006/0084650 A1* 4/2006 Dong ...................... A61P 19/02 514/243
2014/0179668 A1 6/2014 Chakravarty et al.
2016/0083369 A1 3/2016 Shia et al.
2017/0121312 A1 5/2017 Brubaker et al.

FOREIGN PATENT DOCUMENTS

| | | | |
|---|---|---|---|
| CN | 101184758 | A | 5/2008 |
| CN | 101535303 | A | 9/2009 |
| CN | 104039956 | A | 9/2014 |
| CN | 108473468 | A | 8/2018 |
| CN | 108689994 | A | 10/2018 |
| CN | 109180677 | A | 1/2019 |
| CN | 111285882 | A | 6/2020 |
| CN | 111961034 | A | 11/2020 |
| EP | 0995750 | A1 | 4/2000 |
| WO | 200068208 | A1 | 11/2000 |
| WO | 2006104889 | A2 | 10/2006 |
| WO | 2007147103 | A2 | 12/2007 |
| WO | 2007147109 | A2 | 12/2007 |
| WO | 2009050236 | A1 | 4/2009 |
| WO | 2014105958 | A2 | 7/2014 |
| WO | 2016083369 | A1 | 6/2016 |

(Continued)

OTHER PUBLICATIONS

Fleming et al., J. Med. Chem., 2010, 53, 7902-7917 (Year: 2010).*

(Continued)

*Primary Examiner* — John S Kenyon
*Assistant Examiner* — Sara Elizabeth Bell
(74) *Attorney, Agent, or Firm* — NKL Law; Bin Lu; Allen Xue

(57) ABSTRACT

The present invention belongs to the field of medical technology and specifically disclosed is a compound represented by formula (I'), or a pharmaceutically acceptable salt, stereoisomer, solvate or prodrug thereof, and each symbol therein is as defined in the claims. The compound of the present invention may be used as a drug for regulating RET kinase activity or treating RET-related diseases, and has better pharmacokinetic properties.

I'

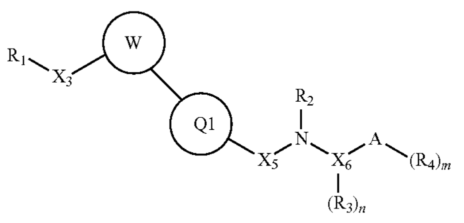

10 Claims, No Drawings

(56) References Cited

FOREIGN PATENT DOCUMENTS

| | | | | | |
|---|---|---|---|---|---|
| WO | 2018017983 | A1 | | 1/2018 | |
| WO | 2018022761 | A1 | | 2/2018 | |
| WO | 2018136663 | A1 | | 7/2018 | |
| WO | WO-2018213329 | A1 | * | 11/2018 | ........... A61K 31/436 |
| WO | WO-2020175968 | A1 | * | 9/2020 | |

OTHER PUBLICATIONS

Acharya et al., Expert Opinion on Therapeutic Patents, 2022, 32, 1067-1077 (Year: 2022).*
Han, H., AAPS Pharmsci., 2000, 2, 1-11 (Year: 2000).*
International Search Report and Written Opinion; PCT Application No. PCT/CN2020/091425; mailed Jun. 30, 2020.
English abstract of International Search Report; retrieved from https://patentscope.wipo.int/search/en/detail.jsf?docld=WO2020233641&_cid=P10-KW15WP-52452-1; on Nov. 15, 2021.
English abstract of CN108473468; retrieved from www.espacenet.com on Nov. 15, 2021.
English abstract of CN109180677; retrieved from www.espacenet.com on Nov. 15, 2021.
English abstract of CN108689994; retrieved from www.espacenet.com on Nov. 15, 2021.
Database Registry [Online], "1-[6, 7-dihydro-2-(4-morpholinylmethyl)-SH cyclopenta[4,5]thieno[2, 3-d]pyri midin-4-yl]-N-(phenylmethyl)-4-Piperidinecarboxamide" (Abstract) Database Accession No. 877136-72-6, Chemical Abstracts Service, Columbus, Ohio, US (Mar. 17, 2006): 1 page.

* cited by examiner

COMPOUND USED AS RET KINASE INHIBITOR AND APPLICATION THEREOF

CROSS REFERENCE TO RELATED APPLICATIONS

The present application is the U.S. National Phase under 35 U.S.C. § 371 of International Application No. PCT/CN2020/091425, filed May 20, 2020, which claims the benefit of Chinese Patent Application No. 201910417078.6, which was filed with State Intellectual Property of P. R. China on May 20, 2019, the entire content of each of which is herein incorporated by reference.

TECHNICAL FIELD

The invention relates to the technical field of medicine, in particular to a compound used as RET kinase inhibitor and application thereof in regulating RET kinase activity or treating RET-related diseases.

BACKGROUND OF THE INVENTION

RET (Rearranged during transfection) gene is located on chromosome 10, RET protein encoded thereby is a receptor tyrosine kinase (RTK) which exists on cell membrane. Its mutation types mainly include fusion mutation with KIF5B, TRIM33, CCDC6 and NCOA4 genes, and point mutation such as M918T. Common RET mutations mainly occur in thyroid cancer, non-small cell lung cancer and other cancer types. The incidence of RET gene fusion is about 1%~2% in NSCLC patients, and is 10%~20% in papillary thyroid carcinoma (accounting for about 85% of all thyroid cancers). RET fusion is more common in young patients, especially in young non-smoking lung adenocarcinoma patients, and the incidence is as high as 7%~17%. At present, the treatment scheme for RET gene change is mainly to use multi-kinase inhibitors, such as carbotinib and vandetanil. Due to the low targeting, serious toxicity related to VEGFR inhibition caused by off-target usually occurs.

Blueprint and Loxo Oncology have disclosed their highly effective and selective oral RET inhibitors BLU-667 and LOXO-292. The results of Blueprint Phase I clinical data show that BLU-667 shows broad anti-tumor activity, and the overall remission rate (ORR) in tumor patients with RET fusion and mutation is 45%, among which the ORR in patients with non-small cell lung cancer and medullary thyroid carcinoma is 50% and 40%, respectively. Recently, FDA granted LOXO-292, a research drug of Loxo Oncology Company, as a breakthrough therapy for treating patients with non-small cell lung cancer (NSCLC) and medullary thyroid cancer (MTC) carrying RET genetic mutations.

Both BLU-667 and LOXO-292 are still in clinical trial stage. Therefore, developing novel compounds with RET kinase inhibitory activity and better pharmacodynamic and pharmacokinetic properties has become an important research project to develop new anti-tumor drugs which can be finally used in the treatment of human tumors and other diseases.

SUMMARY OF THE INVENTION

The invention provides a novel compound with RET kinase inhibitory activity and better pharmacodynamic and pharmacokinetic properties.

In the first aspect of the invention, a compound for use as a RET kinase inhibitor is provided, and the compound is a compound of formula I' or a pharmaceutically acceptable salt, stereoisomer, solvate or prodrug thereof,

I'

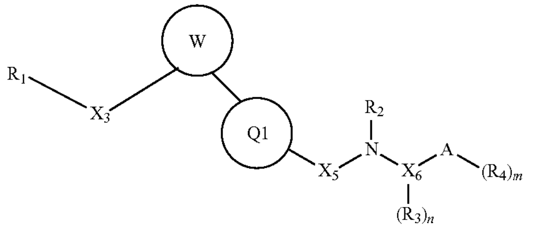

wherein, $R_1$ is substituted or unsubstituted 5-6-membered heterocyclyl or 5-6-membered heteroaryl; the "substituted" means optionally substituted b one or more $R_2$;

$X_3$ is selected from O, $NR_8$, $CR_9R_{10}$,

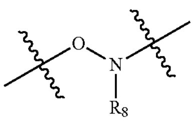

or

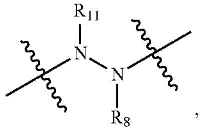

, wherein, $R_8$ and $R_{11}$ are each independently selected from the group consisting of hydrogen, C1-C6 alkyl, C2-C6 alkenyl, C2-C6 alkynyl, C1-C6 haloalkyl, C1-C6 heteroalkyl, C3-C6 cycloalkyl, C3-C6 halocycloalkyl, aryl, heteroaryl, aralkyl and C3-C6 heterocycloalkyl; $R_9$ and $R_{10}$ are each independently selected from the group consisting of hydrogen, halogen, C1-C6 alkyl, C1-C6 haloalkyl, C2-C6 alkenyl, C2-C6 alkynyl, C1-C6 alkoxy, C1-C6 heteroalkyl, C3-C6 cycloalkyl, C3-C6 halocycloalkyl, aryl, heteroaryl, aryloxy, aralkyl, C3-C6 heterocycloalkyl, C1-C6 alkylamino, and C3-C6 cycloalkylamino;

ring W is a substituted or unsubstituted heterocyclylene or heteroarylene, the "substituted" means optionally substituted by 0-2 $R_5$;

ring Q1 is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on the ring Q1 can be substituted by deuterium, hydroxy, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl;

$X_5$ is selected from C(O), S(O), $S(O)_2$,

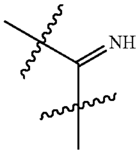

or

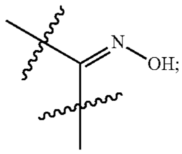

;

$X_6$ is selected from $CR_9$, N or O;

$R_2$ is optionally selected from hydrogen, C1-C6 alkyl, C1-C6 alkoxy, C1-C6 alkylamino, C3-C6 cycloalkyl, or C1-C6 heteroalkyl, wherein alkyl, alkoxy, alkylamino, cycloalkyl and heteroalkyl are each optionally and independently substituted by 0-5 $R^a$;

A is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on the ring A can be substituted by deuterium, hydroxy, halogen, cyano, ester, amide, keto-carbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl;

$R_3$ is optionally selected from hydrogen, deuterium, C1-C6 alkyl, C1-C6 alkoxy, C1-C6 alkylamino, C3-C6 cycloalkyl, or C1-C6 heteroalkyl, wherein alkyl, alkoxy, alkylamino, cycloalkyl and heteroalkyl are each optionally and independently substituted by 0-5 $R^a$;

$R_4$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, aryl, heteroaryl, aryloxy, aralkyl, heterocyclyl, heterocycloalkyl, nitro, cyano, $-C(O)R_6$, $-OC(O)R_6$, $-C(O)OR_6$, $-(C1\text{-}C6\ alkylene)\text{-}C(O)R_6$, $-SR_6$, $-S(O)_2R_6$, $-S(O)_2-N(R_6)(R_7)$, $-(C1\text{-}C6\ alkylene)\text{-}S(O)_2R_6$, $-(C1\text{-}C6\ alkylene)\text{-}S(O)_2-N(R_6)(R_7)$, $-N(R_6)(R_7)$, $-C(O)-N(R_6)(R_7)$, $-N(R_6)-C(O)R_7$, $-N(R_6)-C(O)OR_7$, $-(C1\text{-}C6\ alkylene)\text{-}N(R_6)-C(O)R_7$, $-N(R_6)S(O)_2R_7$ or $-P(O)(R_6)(R_7)$; wherein alkyl, alkenyl, alkynyl, alkoxy, alkylamino, heteroalkyl, cycloalkyl, aryl, heteroaryl, aryloxy, aralkyl, heterocyclyl and heterocycloalkyl are each independently substituted by 0-5 $R^a$;

$R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, aryl, heteroaryl, aryloxy, aralkyl, heterocyclyl, heterocycloalkyl, nitro, oxo, cyano, $-C(O)R_6$, $-OC(O)R_6$, $-C(O)OR_6$, $-(C1\text{-}C6\ alkylene)\text{-}C(O)R_6$, $-SR_6$, $-S(O)_2R_6$, $-S(O)_2-N(R_6)(R_7)$, $-(C1\text{-}C6\ alkylene)\text{-}S(O)_2R_6$, $-(C1\text{-}C6\ alkylene)\text{-}S(O)_2-N(R_6)(R_7)$, $-N(R_6)(R_7)$, $-C(O)-N(R_6)(R_7)$, $-N(R_6)-C(O)R_7$, $-N(R_6)-C(O)OR_7$, $-(C1\text{-}C6\ alkylene)\text{-}N(R_6)-C(O)R_7$, $-N(R_6)S(O)_2R_7$ or $-P(O)(R_6)(R_7)$; wherein alkyl, alkenyl, alkynyl, alkoxy, alkylamino, heteroalkyl, cycloalkyl, aryl, heteroaryl, aryloxy, aralkyl, heterocyclyl and heterocycloalkyl are each independently substituted by 0-5 $R^a$;

$R_6$ and $R_7$ are each independently selected from the group consisting of H, C1-C6 alkyl, C2-C6 alkenyl, C2-C6 alkynyl, C1-C6 alkoxy, C1-C6 heteroalkyl, C3-C6 cycloalkyl, aryl, heteroaryl, aryloxy, aralkyl, C3-C6 heterocycloalkyl, C1-C6 alkylamino, and C3-C6 cycloalkylamino;

$R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano;

m is 0, 1, 2, 3, 4, 5 or 6;

n is 0 or 1;

with the proviso that when the ring W is a substituted or unsubstituted 6-membered heteroaryl, the ring W is substituted by $X_4$, wherein $X_4$ is selected from CN,

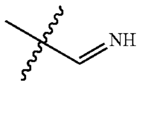

or

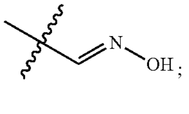

;

and Q1 is connected to the ring W only by carbon atoms on Q1 ring.

In another preferred embodiment, the W ring is substituted or unsubstituted substitutents selected from the group consisting of 5-6-membered monocyclic heterocyclylene, 8-10-membered bicyclic heterocyclylene or 5-6-membered monocyclic heteroarylene or 8-10-membered bicyclic heteroarylene; the "substituted" means optionally substituted by 0-2 $R_5$; $R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, aryl, heteroaryl, aryloxy, aralkyl, heterocyclyl, heterocycloalkyl, nitro, oxo, cyano, $-C(O)R_6$, $-OC(O)R_6$, $-C(O)OR_6$, $-(C1\text{-}C6\ alkylene)\text{-}C(O)R_6$, $-SR_6$, $-S(O)_2R_6$, $-S(O)_2-N(R_6)(R_7)$, $-(C1\text{-}C6\ alkylene)\text{-}S(O)_2R_6$, $-(C1\text{-}C6\ alkylene)\text{-}S(O)_2-N(R_6)(R_7)$, $-N(R_6)(R_7)$, $-C(O)-N(R_6)(R_7)$, $-N(R_6)-C(O)R_7$, $-N(R_6)-C(O)OR_7$, $-(C1\text{-}C6\ alkylene)\text{-}N(R_6)-C(O)R_7$, $-N(R_6)S(O)_2R_7$ or $-P(O)(R_6)(R_7)$; wherein alkyl, alkenyl, alkynyl, alkoxy, alkylamino, heteroalkyl, cycloalkyl, aryl, heteroaryl, aryloxy, aralkyl, heterocyclyl and heterocycloalkyl are each independently substituted by 0-5 $R^a$; $R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano.

In another preferred embodiment, the compound represented by formula I', or pharmaceutically acceptable salt, stereoisomer, solvate or prodrug thereof, the W ring is selected from

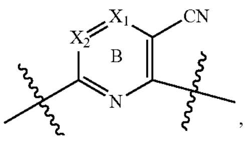

,

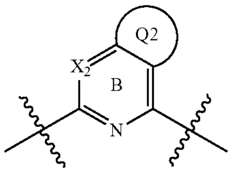

( or

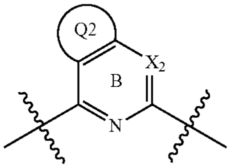

) or

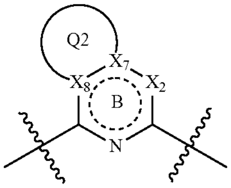

( or

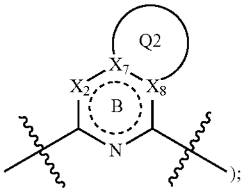

);

wherein $X_1$, $X_2$, $X_7$ and $X_8$ are each independently selected from N or $CR_5$; and at least one of $X_7$ and $X_8$ is N;

$R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein alkyl, alkenyl, alkynyl, alkoxy, alkylamino, heteroalkyl and cycloalkyl are each independently substituted by 0-5 $R^a$; $R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano; ring Q2 is optionally selected from five-membered, six-membered or seven-membered saturated ring, unsaturated ring, aromatic ring, heteroaromatic ring, spiro ring or bridge ring, and can contain 0-3 heteroatoms optionally selected from N, O or S, and any hydrogen atom on the ring Q2 can be substituted by deuterium, hydroxy, halogen, cyano, ester, amide, keto-carbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

In another preferred embodiment, the compound of formula I', or the pharmaceutically acceptable salt, stereoisomer, solvate or prodrug thereof has the structure represented by formula (II), formula (III) or formula (IV), (II)

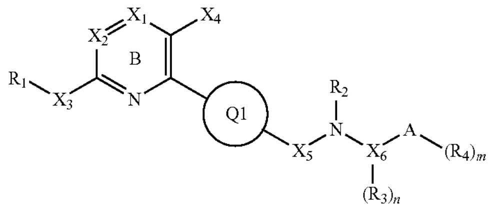

(III)

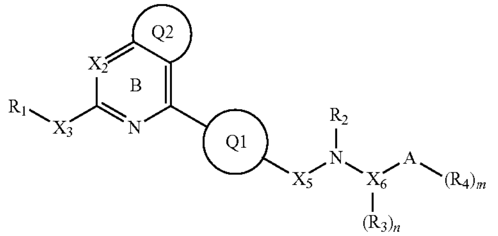

(IV)

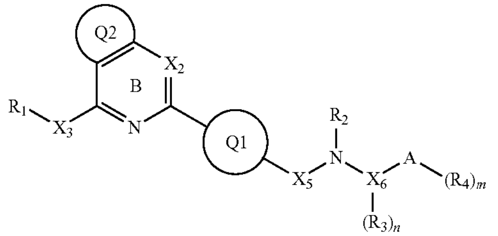

wherein,

A is optionally selected from 3-7 membered saturated ring, unsaturated ring, aromatic ring, heteroaromatic ring, spiro ring or bridge ring, and can contain 0-3 heteroatoms optionally selected from N, O or S;

ring Q1 is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on the ring Q1 can be substituted by deuterium, hydroxy, halogen, cyano, ester, amide, keto-carbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl; In formula (II), Q1 is connected to the ring B only by carbon atoms on ring Q1;

$R_1$ is optionally selected from one of the following structures:

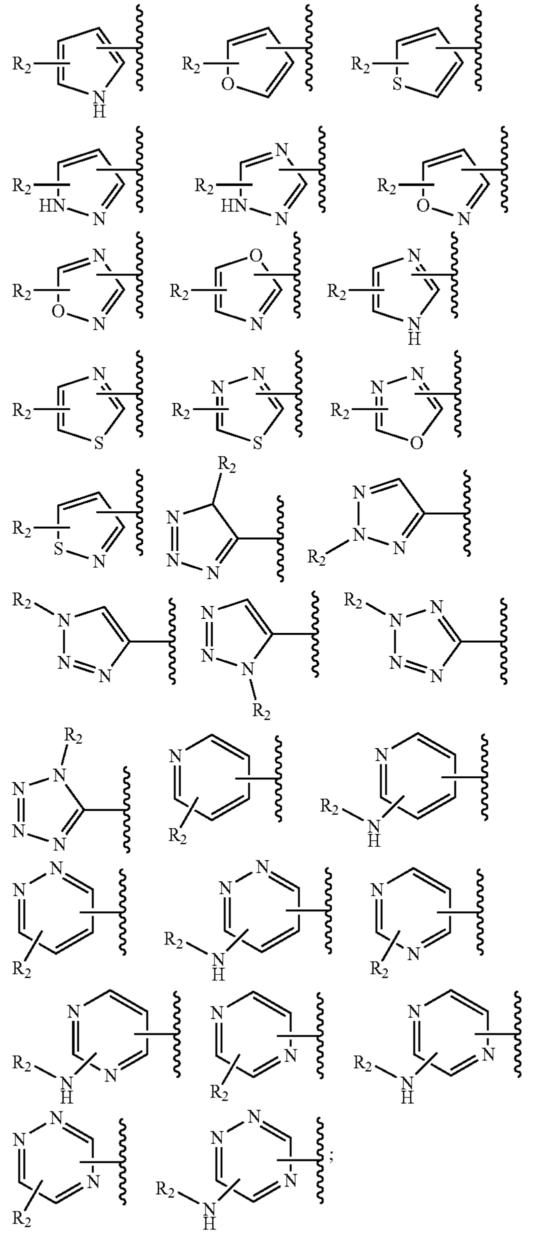

$R_2$ is optionally selected from hydrogen, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$;

$R_3$ is optionally selected from hydrogen, deuterium, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$;

$R^a$ is optionally selected from C1-C6 alkyl, halogen, hydroxy, C1-C6 heteroalkyl, C1-C6 alkoxy, cycloalkyl, heterocycloalkyl or cyano;

$X_1$ and $X_2$ are each independently selected from N or $CR_5$;

$X_3$ is selected from O, $NR_8$, $CR_9R_{10}$,

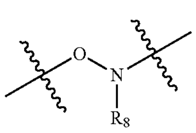 or 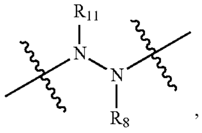, wherein, $R_8$ and $R_{11}$ are each independently selected from the group consisting of hydrogen, C1-C6 alkyl, C2-C6 alkenyl, C2-C6 alkynyl, C1-C6 haloalkyl, C1-C6 heteroalkyl, C3-C6 cycloalkyl, C3-C6 halocycloalkyl, aryl, heteroaryl, aralkyl and C3-C6 heterocycloalkyl; $R_9$ and $R_{10}$ are each independently selected from the group consisting of hydrogen, halogen, C1-C6 alkyl, C1-C6 haloalkyl, C2-C6 alkenyl, C2-C6 alkynyl, C1-C6 alkoxy, C1-C6 heteroalkyl, C3-C6 cycloalkyl, C3-C6 halocycloalkyl, aryl, heteroaryl, aryloxy, aralkyl, C3-C6 heterocycloalkyl, C1-C6 alkylamino, and C3-C6 cycloalkylamino;

$X_4$ is selected from CN,

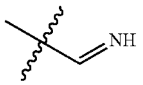 or 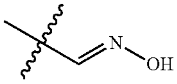;

$X_5$ is selected from C(O), S(O), $S(O)_2$,

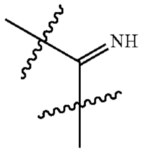 or 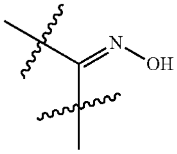;

$X_6$ is selected from $CR_9$, N or O;

$R_4$ and $R_5$ are each independently selected from hydrogen, C1-C6 alkyl, C2-C6 alkenyl, C2-C6 alkynyl, C1-C6 alkoxy, halogen, C1-C6 heteroalkyl, cycloalkyl, aryl, heteroaryl, aryloxy, aralkyl, heterocyclyl, heterocycloalkyl, nitro, cyano, —$C(O)R_6$, —$OC(O)R_6$, —C(O)$OR_6$, —(C1-C6 alkylene)-$C(O)R_6$, —$SR_6$, —$S(O)_2R_6$, —$S(O)_2$—$N(R_6)(R_7)$, —(C1-C6 alkylene)-$S(O)_2R_6$, —(C1-C6 alkylene)-$S(O)_2$—$N(R_6)(R_7)$, —$N(R_6)(R_7)$, —C(O)—$N(R_6)(R_7)$, —$N(R_6)$—$C(O)R_7$, —$N(R_6)$—C(O)$OR_7$, —(C1-C6 alkylene)-$N(R_6)$—$C(O)R_7$, —$N(R_6)S(O)_2R_7$ or —P(O) $(R_6)(R_7)$; wherein alkyl, alkenyl, alkynyl, alkoxy, heteroalkyl, cycloalkyl, aryl, heteroaryl, aryloxy, aralkyl, heterocyclyl and heterocycloalkyl are each independently substituted by 0-5 $R^a$;

$R_6$ and $R_7$ are each independently selected from C1-C6 alkyl, C2-C6 alkenyl, C2-C6 alkynyl, C1-C6 alkoxy, C1-C6 heteroalkyl, C3-C6 cycloalkyl, aryl, heteroaryl, aryloxy, aralkyl, C3-C6 heterocycloalkyl, C1-C6 alkylamino, C3-C6 cycloalkylamino;

ring Q2 is optionally selected from five-membered, six-membered or seven-membered saturated ring, unsaturated ring, aromatic ring, heteroaromatic ring, spiro ring or bridge ring, and can contain 0-3 heteroatoms optionally selected from N, O or S; any hydrogen atom on the ring Q2 can be substituted by deuterium, hydroxy, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl;

m is 0, 1, 2, 3, 4, 5 or 6;

n is 0 or 1.

In another preferred embodiment, $X_3$ is $NR_8$, wherein, $R_8$ is H.

In another preferred embodiment, the compound of formula I', or the pharmaceutically acceptable salt, stereoisomer, solvate or prodrug thereof has the structure represented by formula (2), formula 3) or formula (4).

(2)

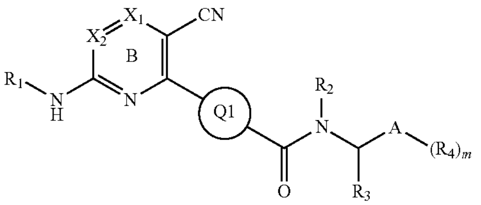

(3)

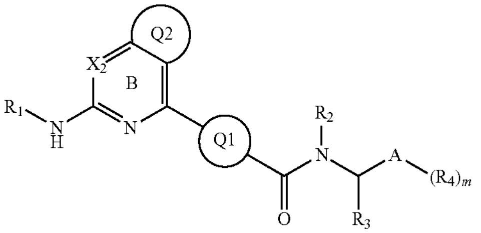

(4)

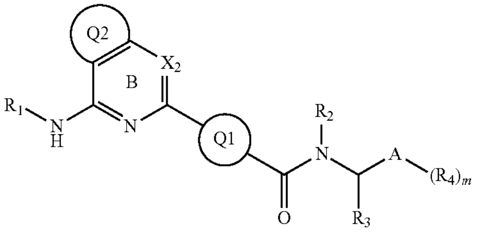

wherein,

A is optionally selected from 3-7 membered saturated ring, unsaturated ring, aromatic ring, heteroaromatic ring, spiro ring or bridge ring, and can contain 0-3 heteroatoms optionally selected from N, O or S;

ring Q1 is optionally selected from 3-7 membered saturated ring, unsaturated ring, aromatic ring, heteroaromatic ring, spiro ring or bridge ring, and can contain 0-3 heteroatoms optionally selected from N, O or S; any hydrogen atom on the ring Q1 can be substituted by deuterium, hydroxy, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl; in formula (2), Q1 is connected to the ring B only by carbon atoms on ring Q1;

$R_1$ is optionally selected from one of the following structures:

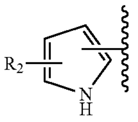 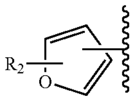 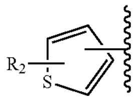

-continued

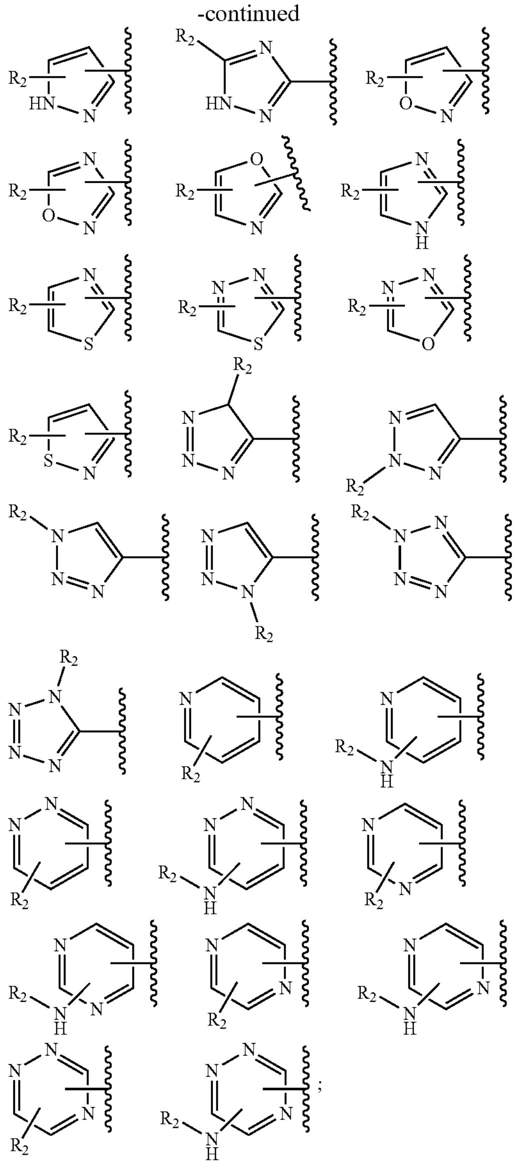

$R_2$ is optionally selected from hydrogen, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$;

$R_3$ is optionally selected from hydrogen, deuterium, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$;

$R^a$ is optionally selected from C1-C6 alkyl, halogen, hydroxy, C1-C6 heteroalkyl, C1-C6 alkoxy, cycloalkyl, heterocycloalkyl or cyano;

$X_1$ and $X_2$ are each independently selected from N or $CR_5$;

$R_4$ and $R_5$ are each independently selected from hydrogen, C1-C6 alkyl, C2-C6 alkenyl, C2-C6 alkynyl, C1-C6 alkoxy, halogen, C1-C6 heteroalkyl, cycloalkyl, aryl, heteroaryl, aryloxy, aralkyl, heterocyclyl, heterocycloalkyl, nitro, cyano, $—C(O)R_6$, $—OC(O)R_6$, $—C(O)OR_6$, —(C1-C6 alkylene)-$C(O)R_6$, $—SR_6$, $—S(O)_2R_6$, $—S(O)_2—N(R_6)(R_7)$, —(C1-C6 alkylene)-$S(O)_2R_6$, —(C1-C6 alkylene)-$S(O)_2—N(R_6)(R_7)$, $—N(R_6)(R_7)$, $—C(O)—N(R_6)(R_7)$, $—N(R_6)—C(O)R_7$, $—N(R_6)—C(O)OR_7$, —(C1-C6 alkylene)-$N(R_6)—C(O)R_7$, $—N(R_6)S(O)_2R_7$ or $—P(O)(R_6)(R_7)$; wherein alkyl, alkenyl, alkynyl, alkoxy, heteroalkyl, cycloalkyl, aryl, heteroaryl, aryloxy, aralkyl, heterocyclyl and heterocycloalkyl are each independently substituted by 0-5 $R^a$;

$R_6$ and $R_7$ are each independently selected from C1-C6 alkyl, C2-C6 alkenyl, C2-C6 alkynyl, C1-C6 alkoxy, C1-C6 heteroalkyl, C3-C6 cycloalkyl, aryl, heteroaryl, aryloxy, aralkyl, C3-C6 heterocycloalkyl, C1-C6 alkylamino, or C3-C6 cycloalkylamino;

ring Q2 is optionally selected from five-membered, six-membered or seven-membered saturated ring, unsaturated ring, aromatic ring, heteroaromatic ring, spiro ring or bridge ring, and can contain 0-3 heteroatoms optionally selected from N, O or S; any hydrogen atom on the ring Q2 can be substituted by deuterium, hydroxy, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl;

m is 0, 1, 2, 3, 4, 5 or 6.

In another preferred embodiment, the compound of formula I', or the pharmaceutically acceptable salt, stereoisomer, solvate or prodrug thereof, the W ring is selected from the group consisting of

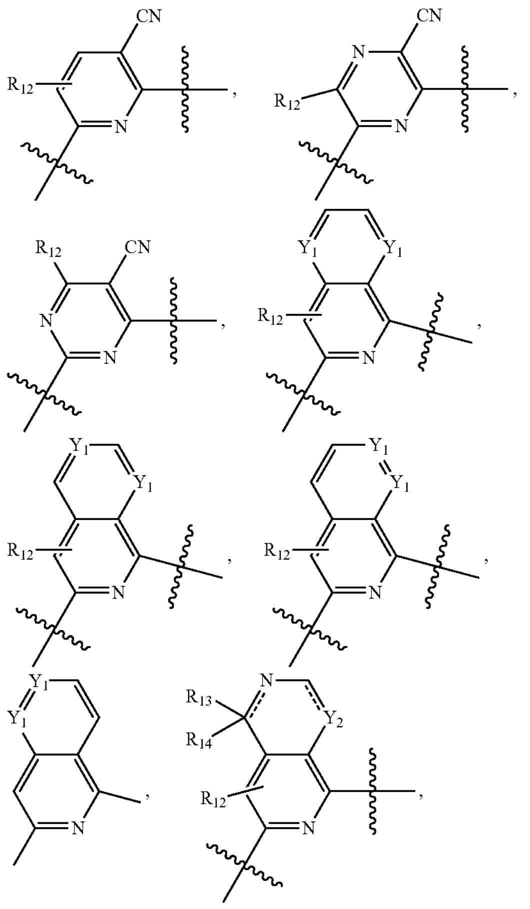

-continued

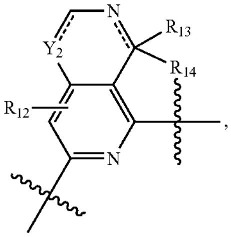,
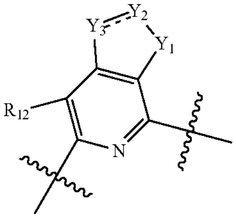,
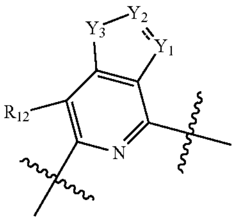,
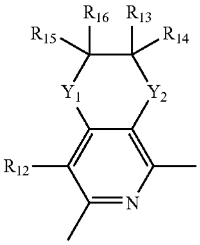,
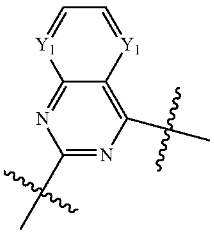,
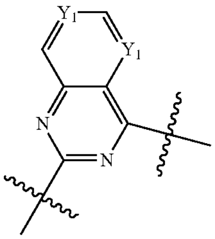,
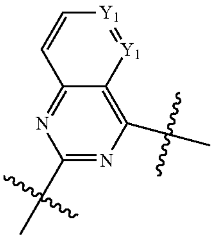,
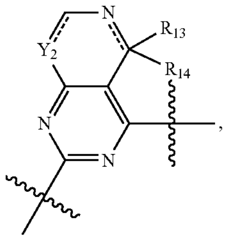,
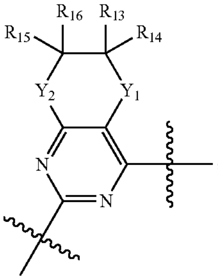,
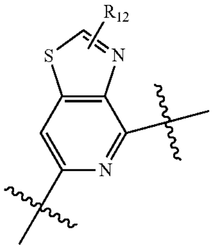,
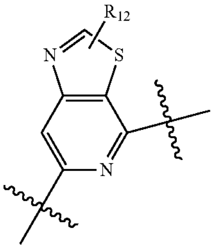,
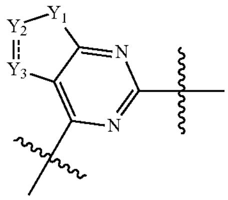,
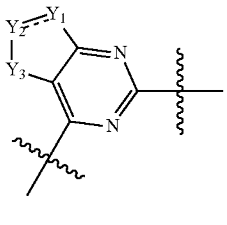,
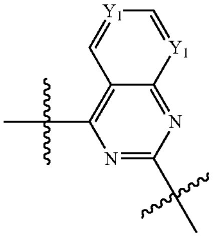, -continued

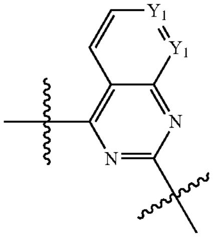,
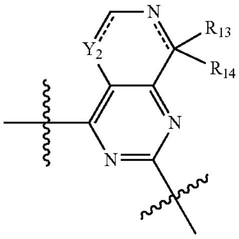,
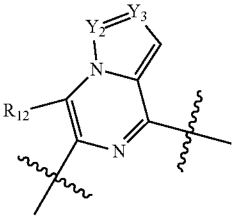,
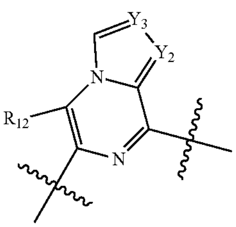,
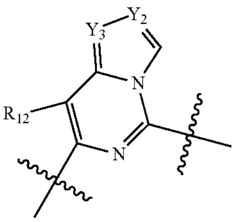,
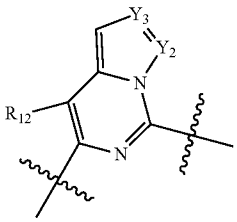,
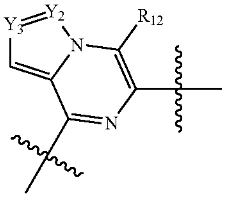,
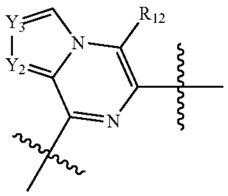,
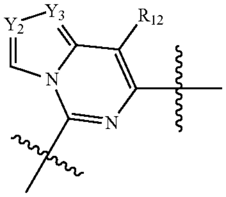, and
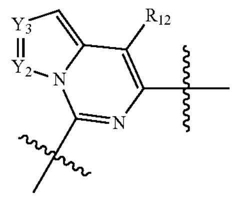, wherein, ═ is a single bond or a double bond;

$R_{12}$ is independently selected from H, halogen, C1-C6 alkyl, C1-C6 alkoxy, C1-C6 alkylamino, nitro, cyano, or amino;

$Y_1$, $Y_2$, and $Y_3$ are each independently selected from O, N, $NR_{17}$, $CR_{13}$ or $CR_{13}R_{14}$;

$R_{13}$, $R_{14}$, $R_{15}$ and $R_{16}$ are each independently selected from H, halogen, C1-C6 alkyl, C1-C6 alkoxy, C1-C6 alkylamino, nitro, cyano, or amino; or $R_{13}$ and $R_{14}$ together with the C atom attached to them form a carbonyl (C═O); or $R_{15}$ and $R_{16}$ together with the C atom attached to them form a carbonyl (C═O);

$R_{17}$ is selected from H or C1-C6 alkyl.

In another preferred embodiment, the W ring is selected from

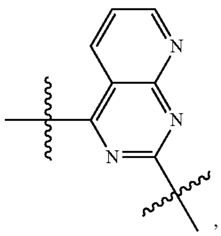
,
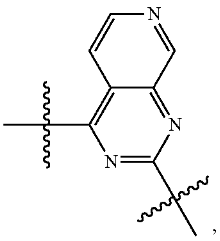
,
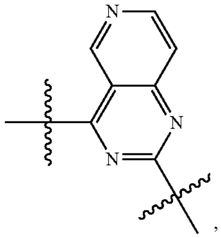
, or
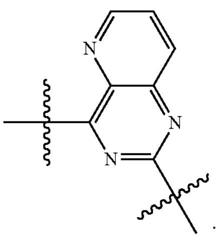
.

In another preferred embodiment, the compound of formula I', or the pharmaceutically acceptable salt, stereoisomer, solvate or prodrug thereof has the structure represented by formula 2',

2'

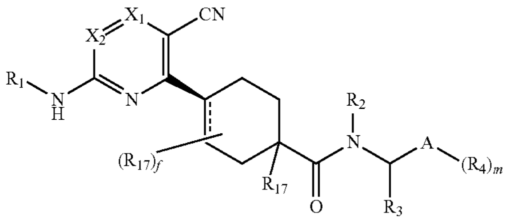

wherein, ⎓ is a single bond or a double bond;

$R_{17}$ is each independently selected from deuterium, halogen, hydroxy, amino, C1-C6 alkyl, C1-C6 haloalkyl, C1-C6 thioalkyl, C1-C6 alkoxy, C1-C6 alkylamino or C3-C6 cycloalkyl;

f is 0, 1, 2, 3, 4, 5, 6, 7, 8 or 9;

$X_1$, $X_2$, $R_1$, $R_2$, $R_3$, $R_4$, A and m are as defined above.

In another preferred embodiment, the compound of formula I', or the pharmaceutically acceptable salt, stereoisomer, solvate or prodrug thereof has the structure represented by formula 2'',

2''

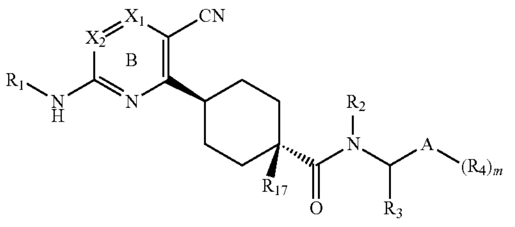

wherein, $R_1$, $R_2$, $R_3$, $R_4$, A, m, $X_1$, $X_2$ and $R_{17}$ are as defined above.

In another preferred embodiment,

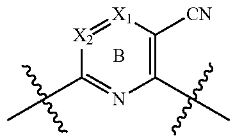

is selected from

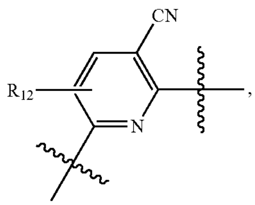
,
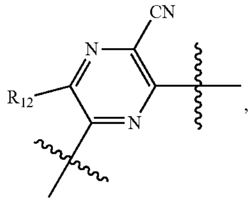
, or
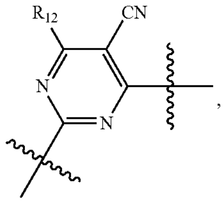
, $R_{12}$ is as defined above.

In another preferred embodiment, the compound of formula I', or the pharmaceutically acceptable salt, stereoisomer, solvate or prodrug thereof has the structure represented by formula 3',

3'

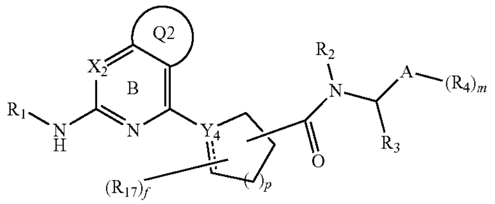

wherein, ⎓ is a single bond or a double bond;

when ⎓ is a single bond, $Y_4$ is selected from N or $CR_{17}$, when ⎓ is a double bond, $Y_4$ is C;

$R_{17}$ is each independently selected from deuterium, halogen, hydroxy, amino, C1-C6 alkyl, C1-C6 haloalkyl, C1-C6 thioalkyl, C1-C6 alkoxy, C1-C6 alkylamino or C3-C6 cycloalkyl;

f is 0, 1, 2, 3, 4, 5, 6, 7, 8 or 9;

p is 0, 1, 2 or 3;

$X_2$, Q2, $R_1$, $R_2$, $R_3$, $R_4$, A and m are as defined above.

In another preferred embodiment, the compound of formula I', or the pharmaceutically acceptable salt, stereoisomer, solvate or prodrug thereof has the structure represented by formula 3', 3″
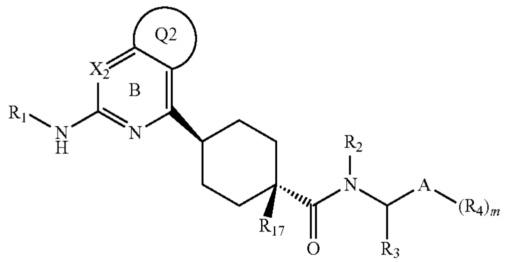
$R_1$, $X_2$, $R_2$, $R_3R_4$, A, Q2, m and $R_{17}$ are as defined above. In another preferred embodiment,
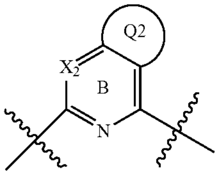
(or
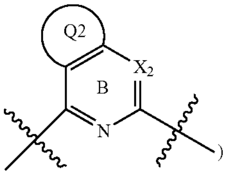
)
is selected from:
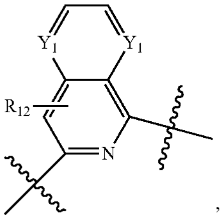
,
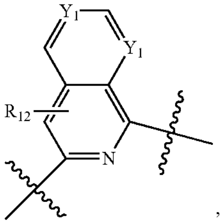
,
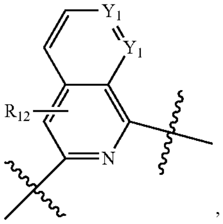
,
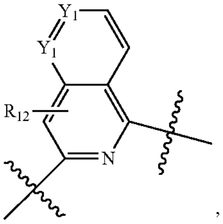
,
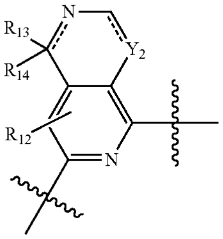
,
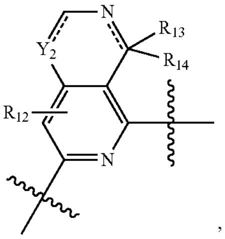
,
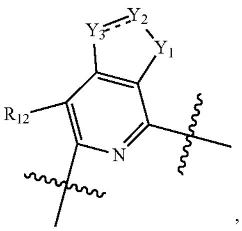
,
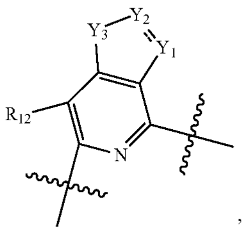
,
-continued
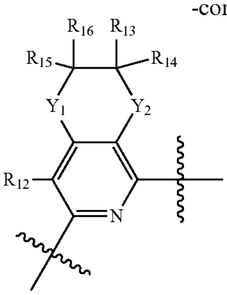
,
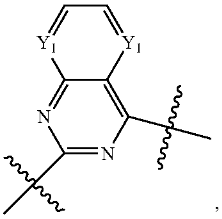
,
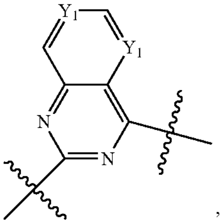
,
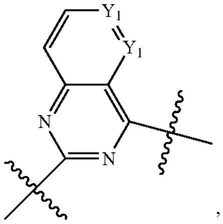
,
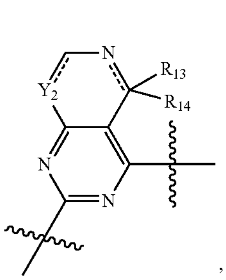
,
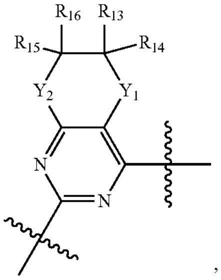
,
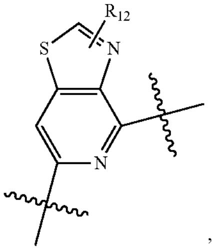
,
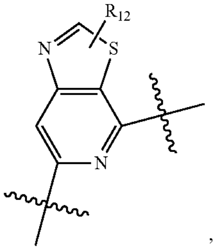
,
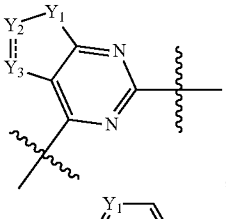
,
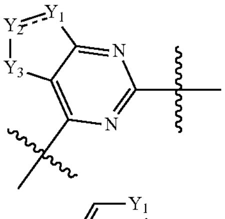
,
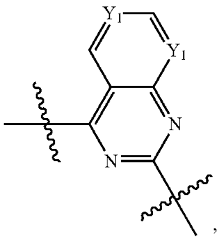
,
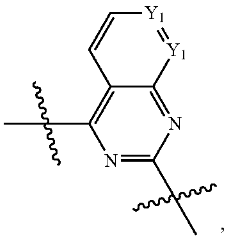
, or
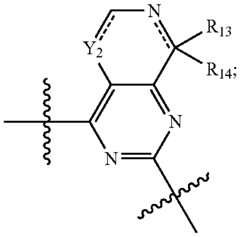

wherein, $\overline{==}$ is a single bond or a double bond;

$Y_1$, $Y_2$, $Y_3$, $R_{12}$, $R_{13}$, $R_{14}$, $R_{15}$ and $R_{16}$ are as defined above.

In another preferred embodiment, the compound of formula I', or the pharmaceutically acceptable salt, stereoisomer, solvate or prodrug thereof has the structure represented by formula 4',

4'

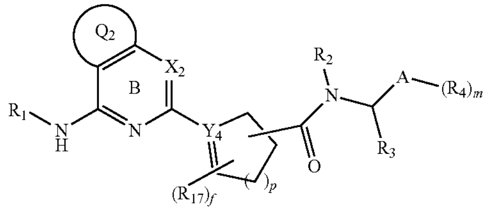

wherein, $\overline{==}$ is a single bond or a double bond;

when $\overline{==}$ is a single bond, $Y_4$ is selected from N or $CR_{17}$, when $\overline{==}$ is a double bond, $Y_4$ is C;

$R_{17}$ is each independently selected from deuterium, halogen, hydroxy, amino, C1-C6 alkyl, C1-C6 haloalkyl, C1-C6 thioalkyl, C1-C6 alkoxy, C1-C6 alkylamino or C3-C6 cycloalkyl;

f is 0, 1, 2, 3, 4, 5, 6, 7, 8 or 9;

p is 0, 1, 2 or 3;

$X_2$, Q2, $R_1$, $R_2$, $R_3$, $R_4$, A and m are as defined above.

In another preferred embodiment, the compound of formula I', or the pharmaceutically acceptable salt, stereoisomer, solvate or prodrug thereof has the structure represented by formula 4',

4''

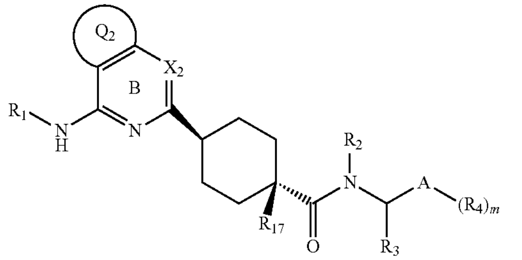

$R_1$, $X_2$, $R_2$, $R_3$, $R_4$, A, Q2, m and $R_{17}$ are as defined above.

In another preferred embodiment,

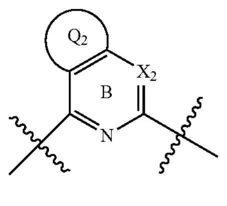

is

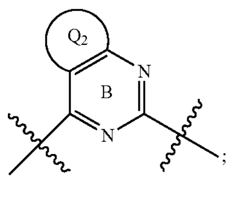

;

wherein $Q_2$ is as defined above.

In another preferred embodiment, the compound of formula I', or the pharmaceutically acceptable salt, stereoisomer, solvate or prodrug thereof has the structure represented by formula 5 or formula 6,

5

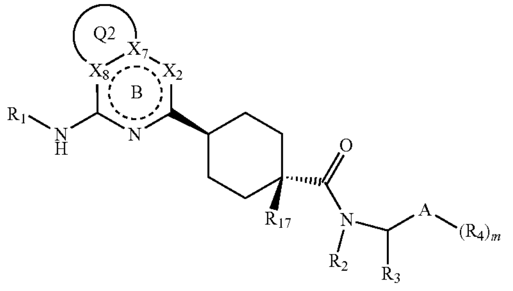

6

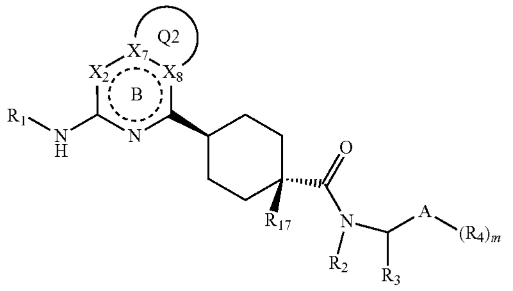

wherein $R_1$, $X_7$, $X_8$, $X_2$, Q2, $R_2$, $R_3$, $R_4$, $R_{17}$, A and m are as defined above, and at least one of $X_7$, $X_8$ is N.

In another preferred embodiment, the compound of formula I', or the pharmaceutically acceptable salt, stereoisomer, solvate or prodrug thereof, A is aromatic ring or heteroaromatic ring, the heteroaromatic ring contains 0 to 3 heteroatoms selected from N, O or S; any hydrogen atom on the ring A can be substituted by deuterium, hydroxy, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

In another preferred embodiment, A is phenyl, pyridyl, pyrazinyl, pyrimidinyl or pyridazinyl, and any hydrogen atom on the ring A can be substituted by deuterium, hydroxyl, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

In another preferred embodiment, the compound of formula I', or the pharmaceutically acceptable salt, stereoisomer, solvate or prodrug thereof, $R_4$ is each independently selected from aryl, heteroaryl, aryloxy, aralkyl, or heterocyclyl; wherein each aryl, heteroaryl, aryloxy, aralkyl and heterocyclyl are independently substituted by 0 to 5 $R^a$; $R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano.

In another preferred embodiment, $R_4$ is 5-membered heteroaryl, which can be independently substituted by 0 to 5 $R^a$; $R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano.

In another preferred embodiment, $R_4$ is selected from

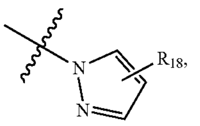

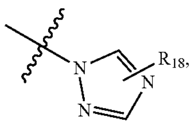

-continued

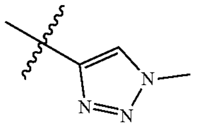 or 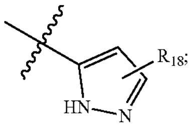

wherein $R_{18}$ is selected from halogen (preferably F) or C1-C6 alkyl.

In another preferred embodiment, m is 1.

In another preferred embodiment, $R_3$ is H, C1-C6 alkyl or C1-C6 alkoxy.

In another preferred embodiment, $R_2$ is H.

In another preferred embodiment, $R_1$, $X_3$, W, Q1, $X_5$, $X_6$, $R_2$, $R_3$, $R_4$, A, m and n are the specific group corresponding to each specific compound in the Example.

In another preferred embodiment, $R_1$, $X_1$, $X_2$, $X_3$, Q1, Q2, $X_5$, $X_6$, $R_2$, $R_3$, $R_4$, A, m and n are the specific group corresponding to each specific compound in the Example.

In another preferred embodiment,

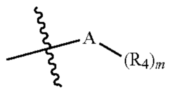 is 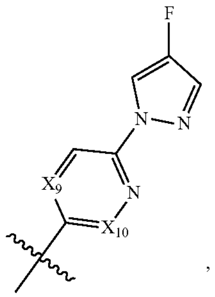, where $X_9$ and $X_{10}$ are each independently selected from N or $CR_5$, wherein, $R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein each alkyl, alkenyl, alkynyl, alkoxy, alkylamino, heteroalkyl and cycloalkyl is independently substituted by 0 to 5 $R^a$; $R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano.

In another preferred embodiment, the compound of formula I', or the pharmaceutically acceptable salt, stereoisomer, solvate or prodrug thereof has the structure represented by formula 5' or formula 6'

5'

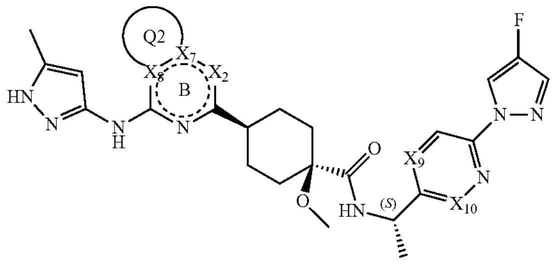

-continued

6'

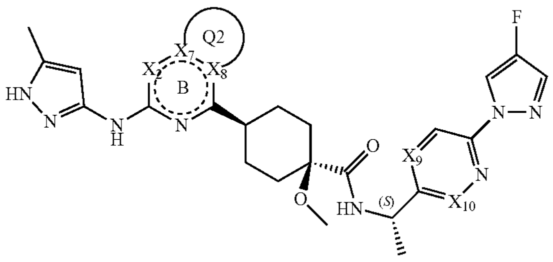

wherein $X_2$, $X_7$, $X_8$, $X_9$ and $X_{10}$ are each independently selected from N or $CR_5$, and at least one of $X_7$ and $X_8$ is N, $R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein each alkyl, alkenyl, alkynyl, alkoxy, alkylamino, heteroalkyl and cycloalkyl is independently substituted by 0 to 5 $R^a$; $R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano;

ring Q2 is optionally selected from five-membered, six-membered or seven-membered saturated ring, unsaturated ring, aromatic ring, heteroaromatic ring, spiro ring or bridge ring, and can contain 0-3 heteroatoms optionally selected from N, O or S; any hydrogen atom on the ring Q2 can be substituted by deuterium, hydroxy, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

In another preferred embodiment,

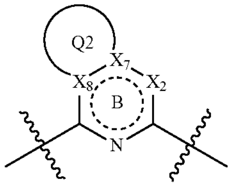 (or 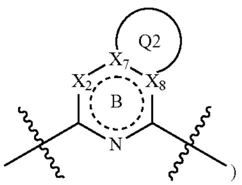)

is selected from

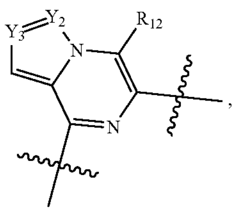, 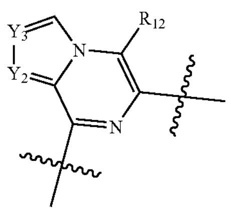,

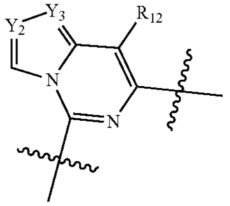, 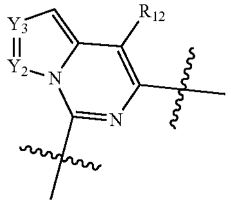,

-continued
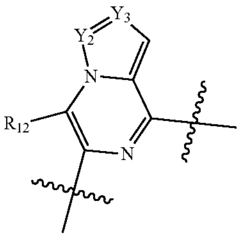
,
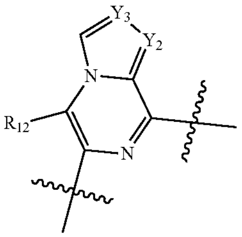
,
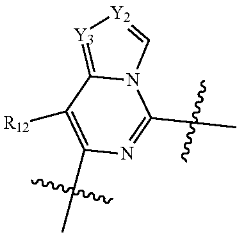
, or
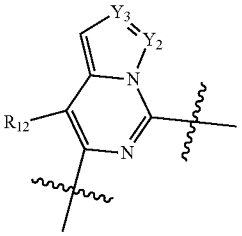
,
$Y_2$, $Y_3$ and $R_{12}$ are as defined above.
In another preferred embodiment, the compound, or the pharmaceutically acceptable salt, stereoisomer, solvate or prodrug thereof can be optionally selected from the following compound:
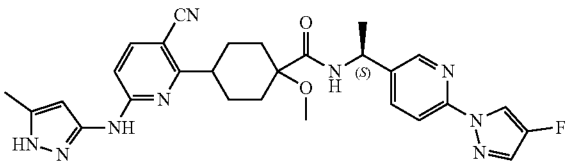
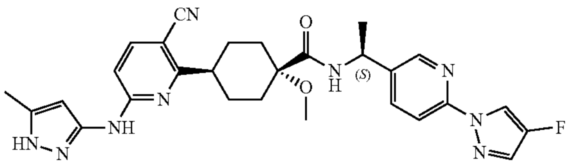
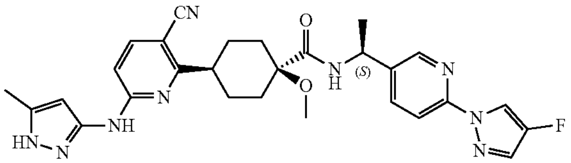
-continued
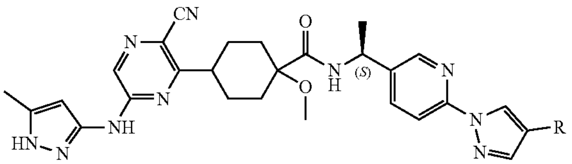
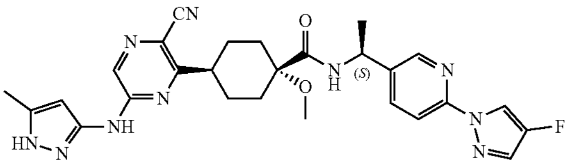
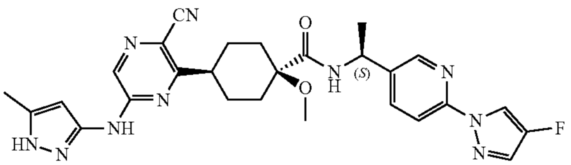
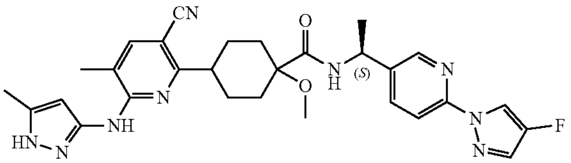
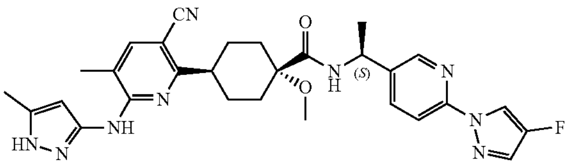
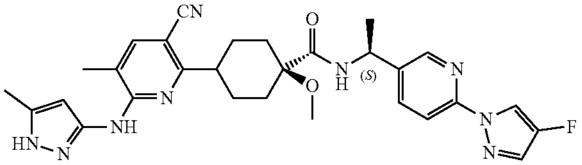
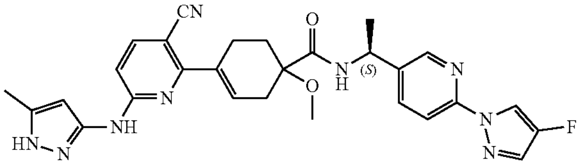
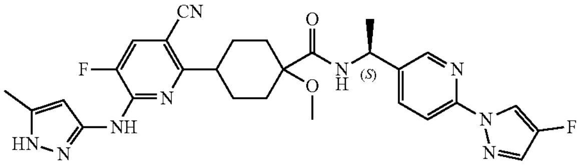
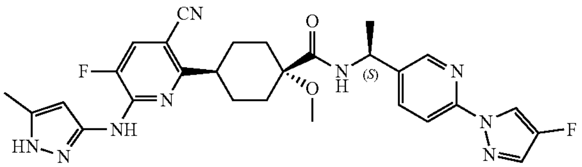
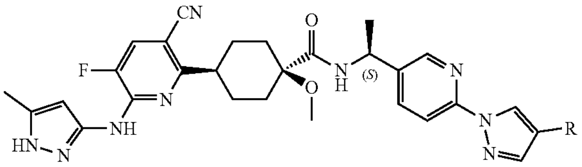

-continued
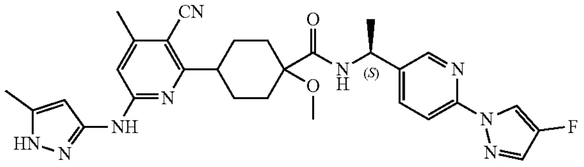
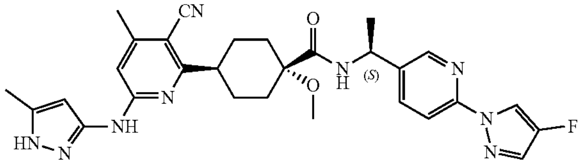
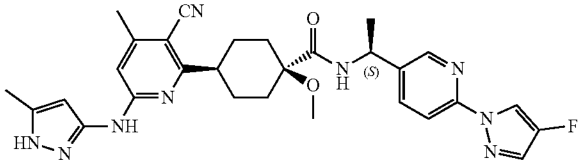
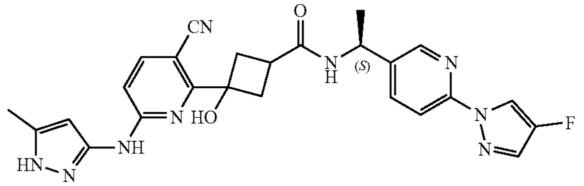
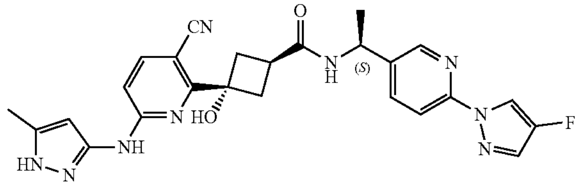
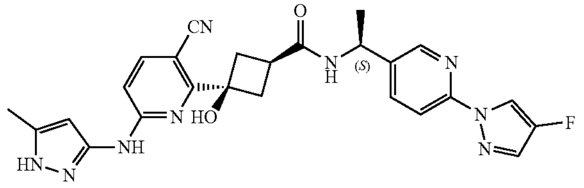
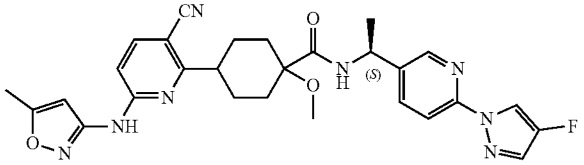
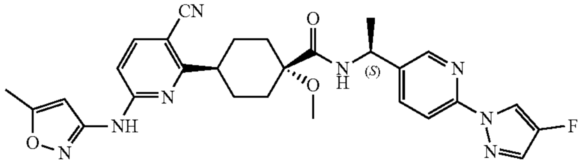
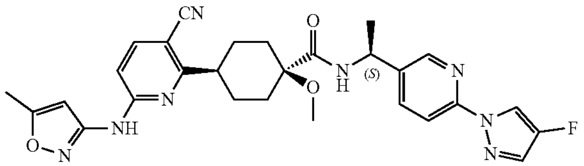
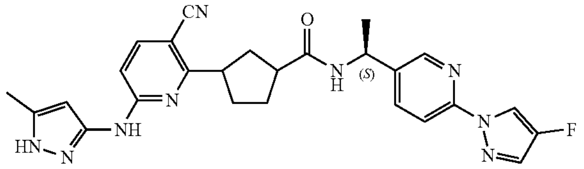
-continued
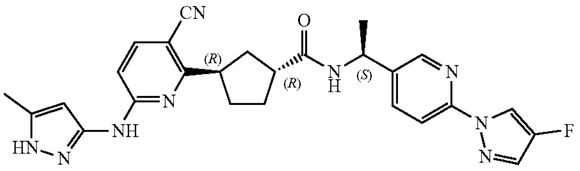
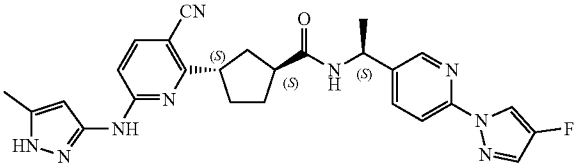
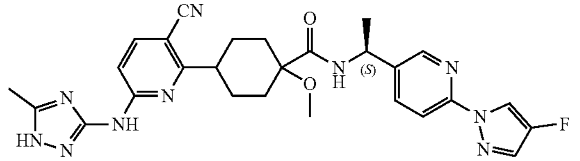
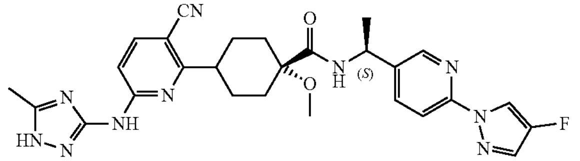
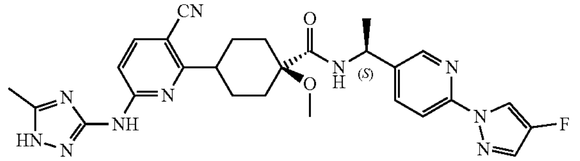
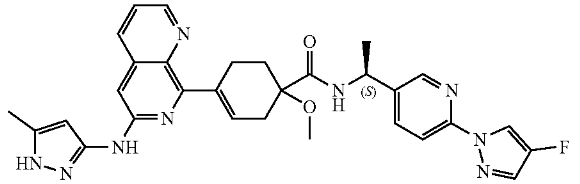
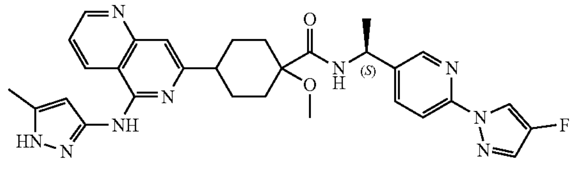
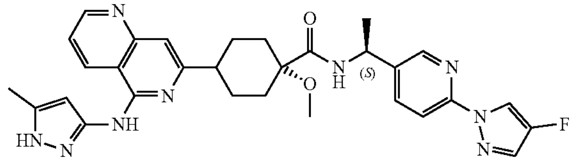
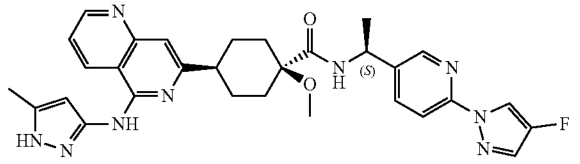
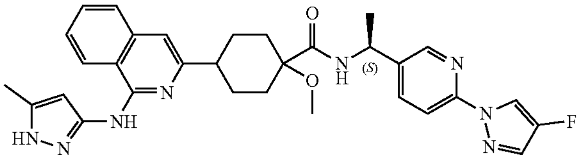

-continued
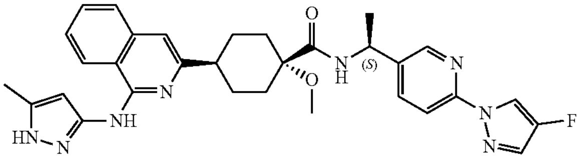
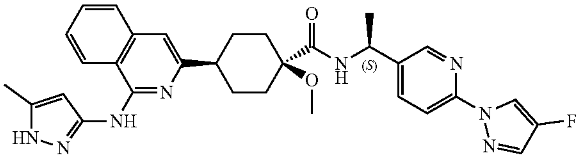
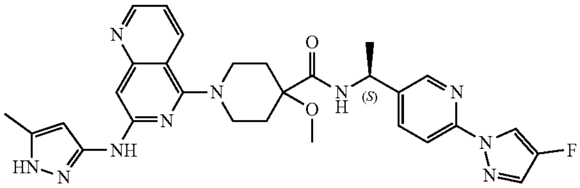
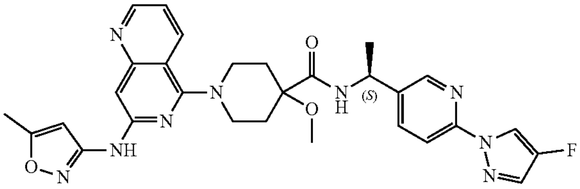
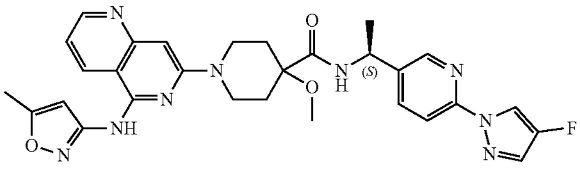
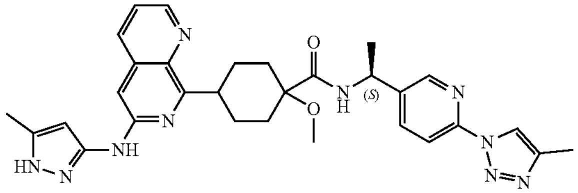
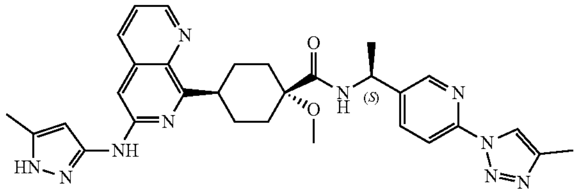
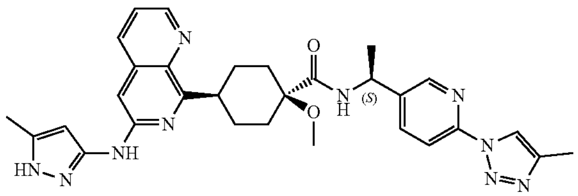
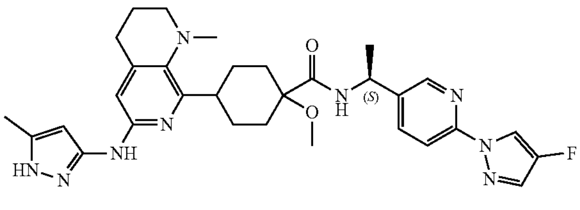
-continued
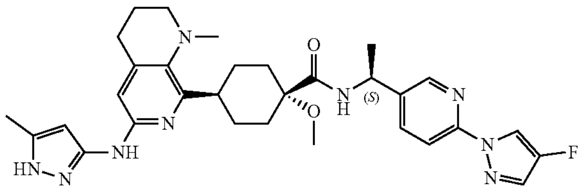
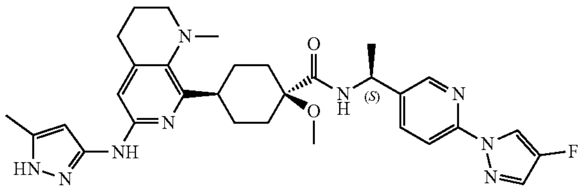
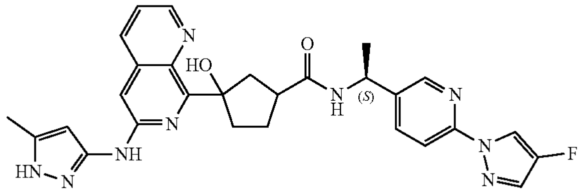
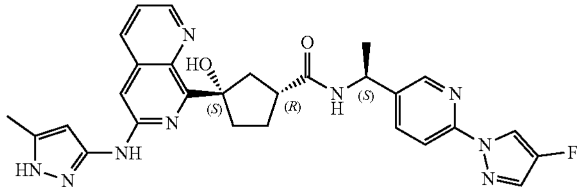
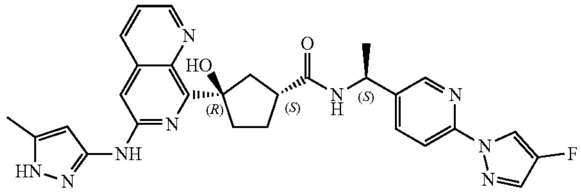
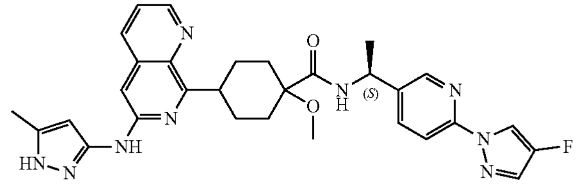
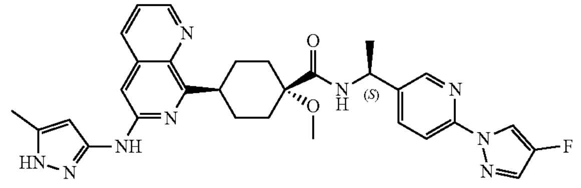
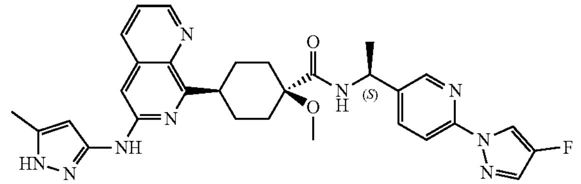
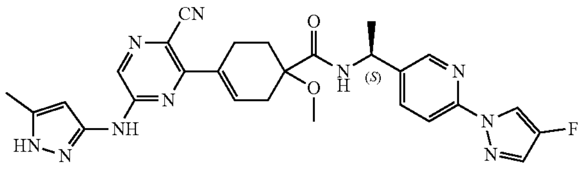

-continued
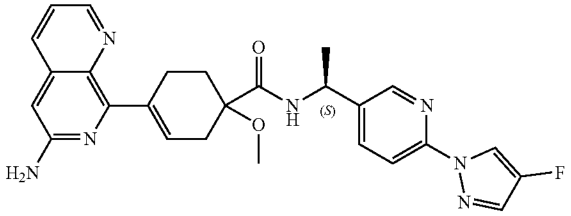
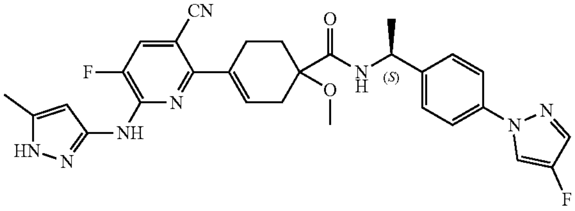
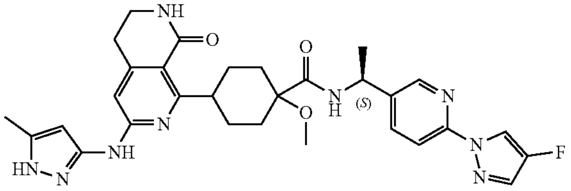
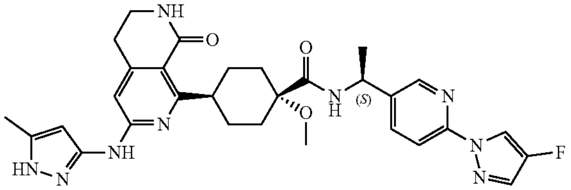
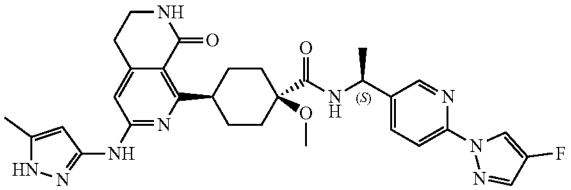
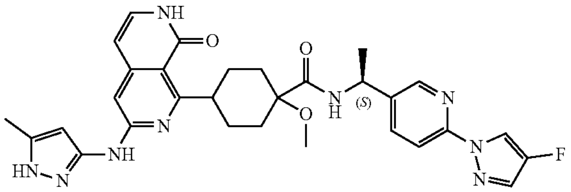
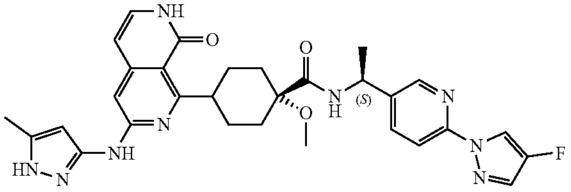
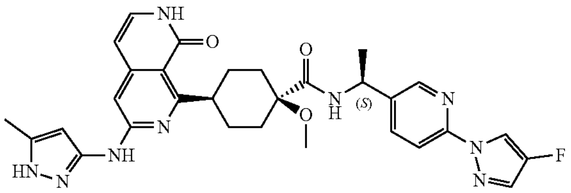
-continued
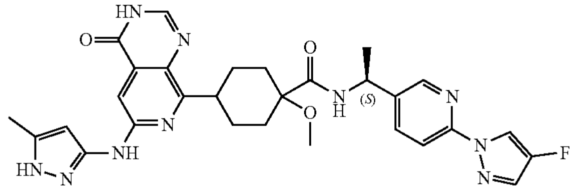
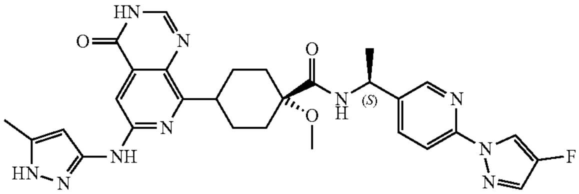
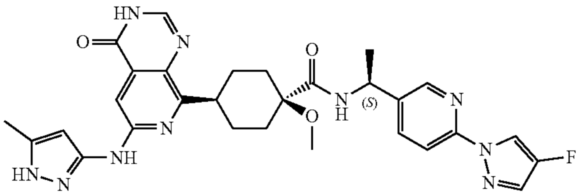
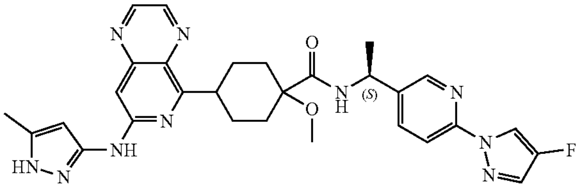
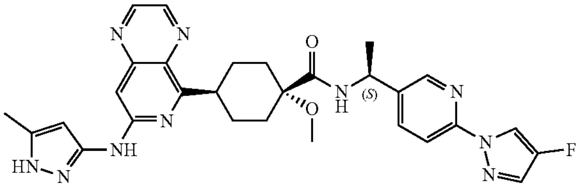
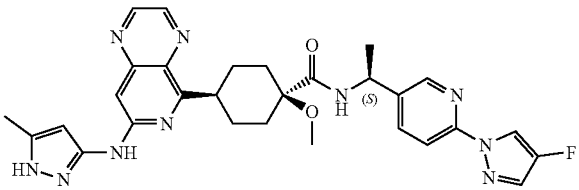
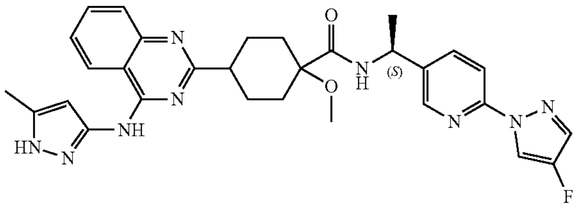
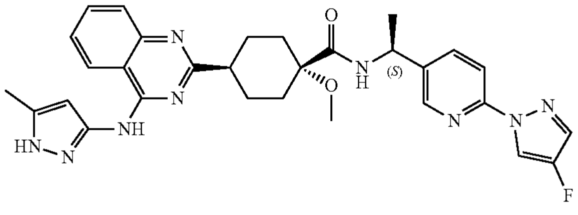

-continued
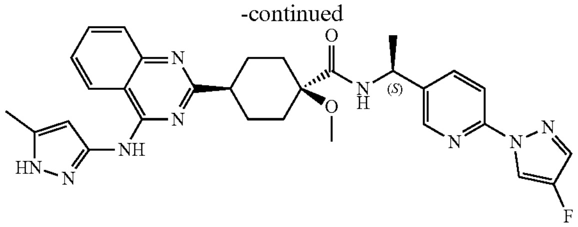
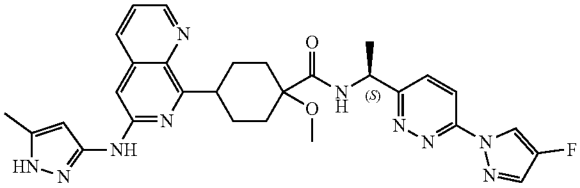
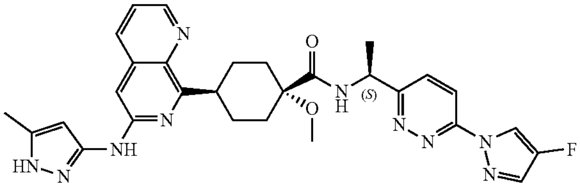
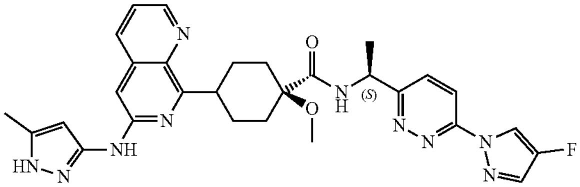
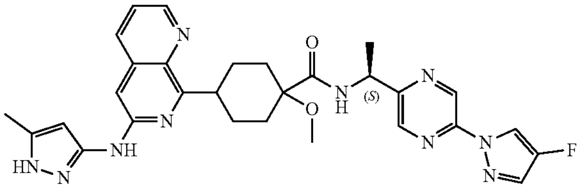
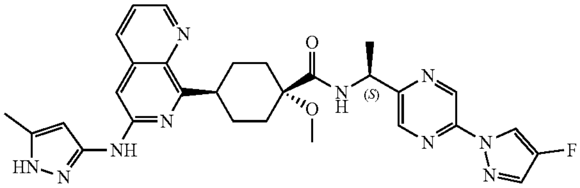
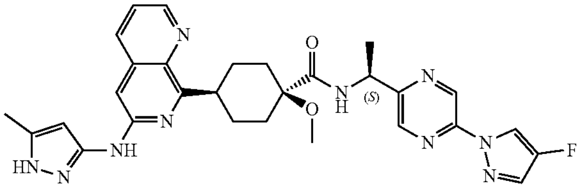
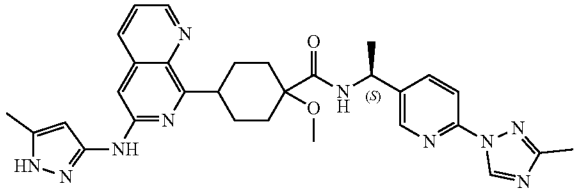
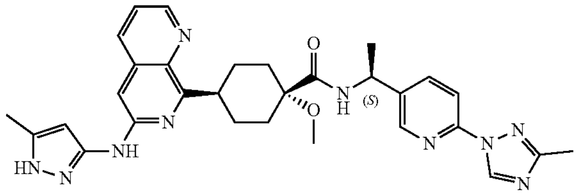
-continued
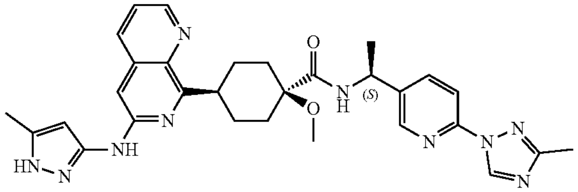
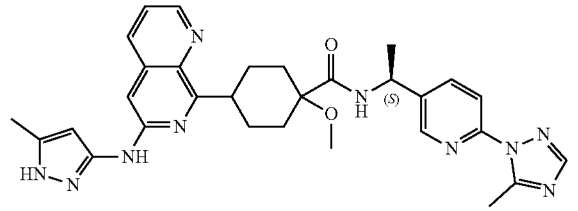
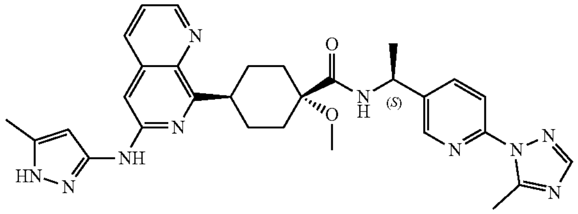
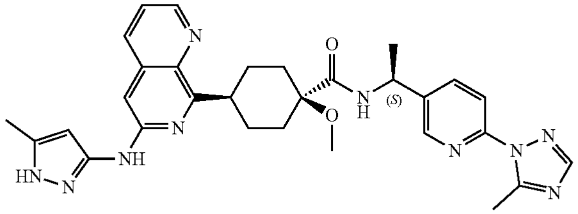
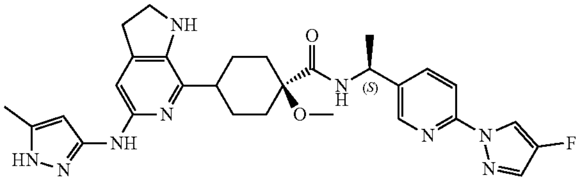
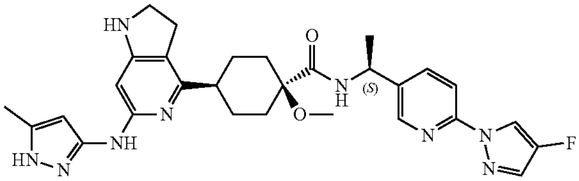
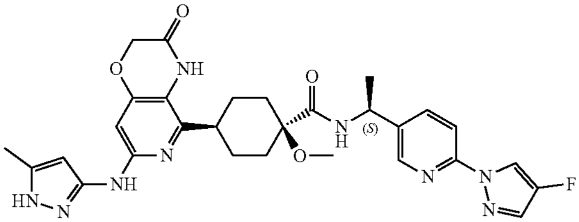
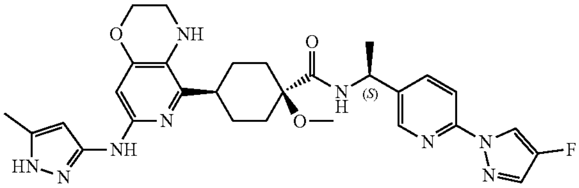

-continued
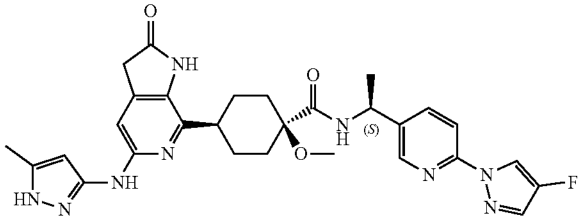
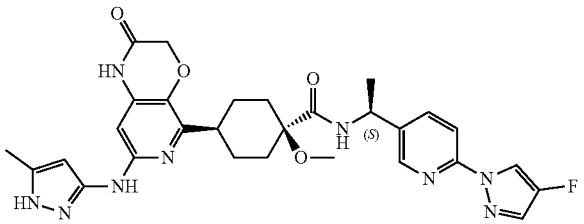
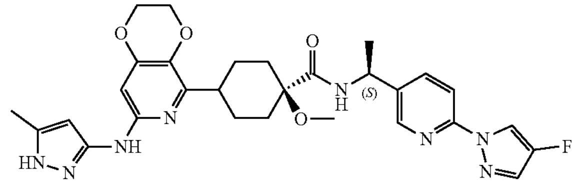
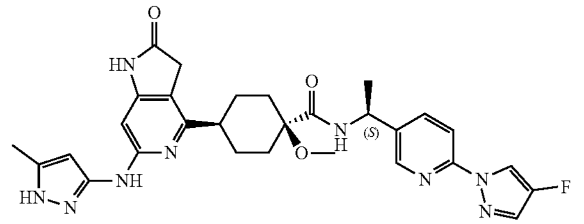
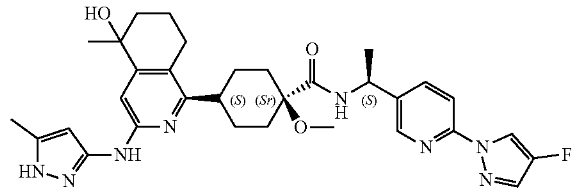
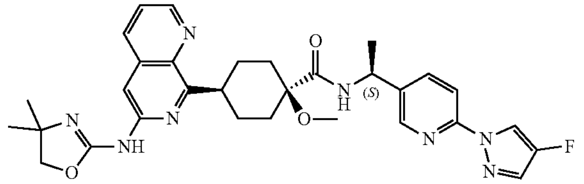
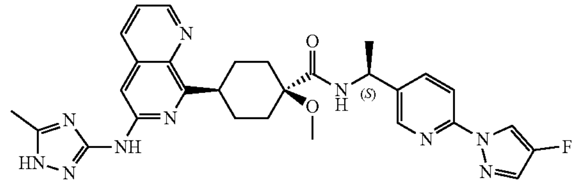
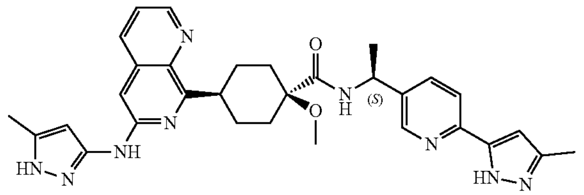
-continued
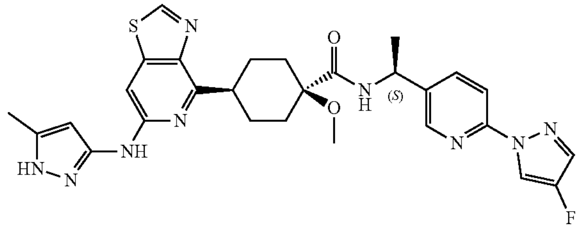
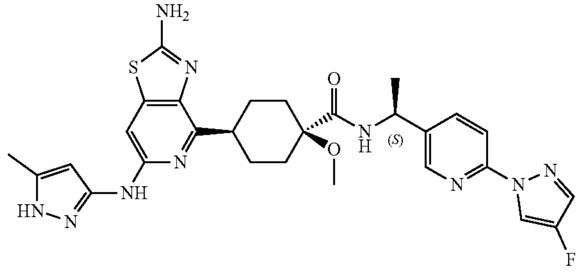
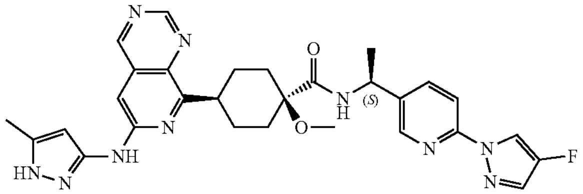
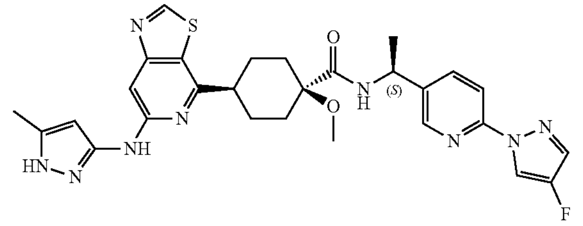
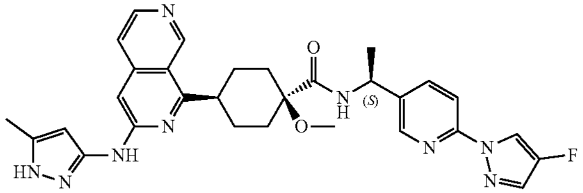
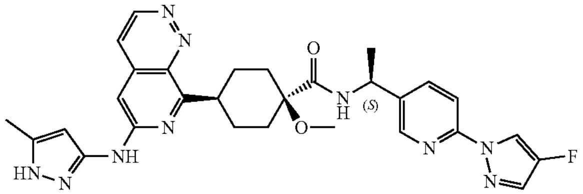
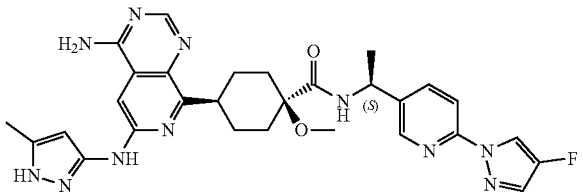
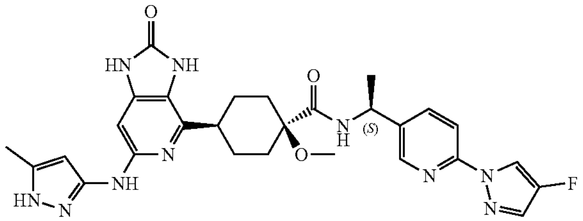

-continued
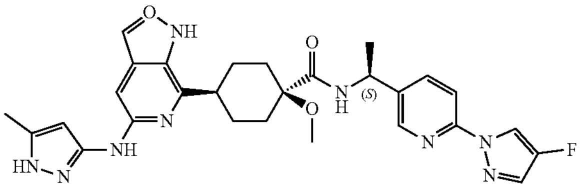
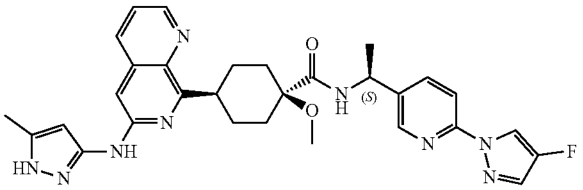
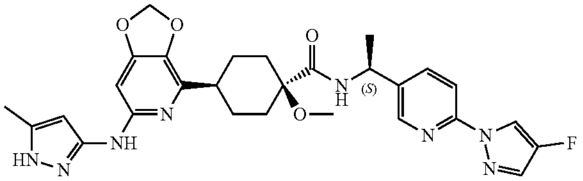
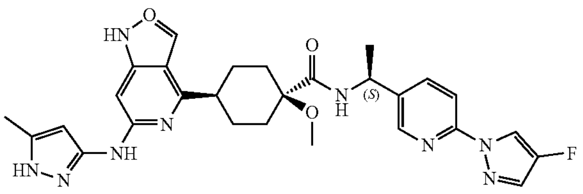
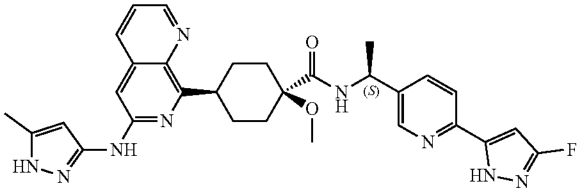
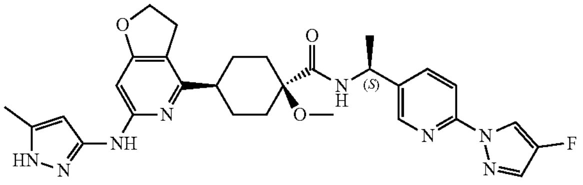
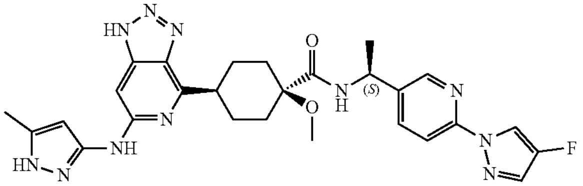
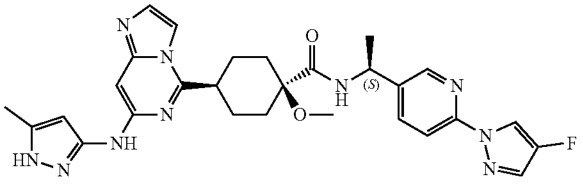
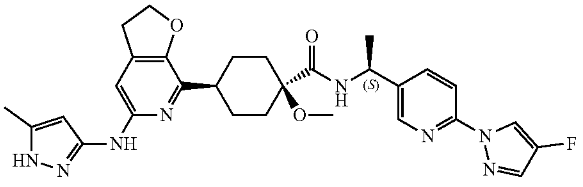
-continued
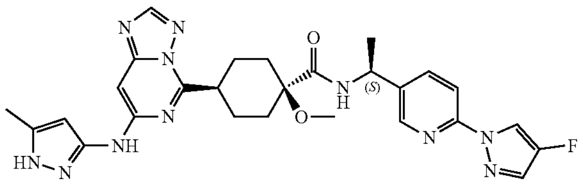
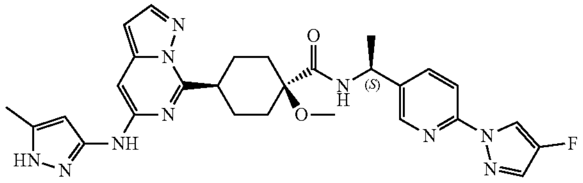
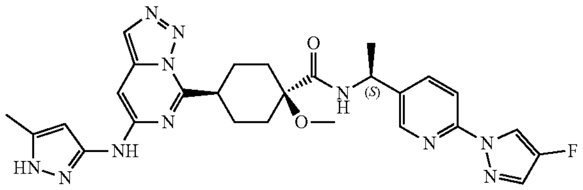
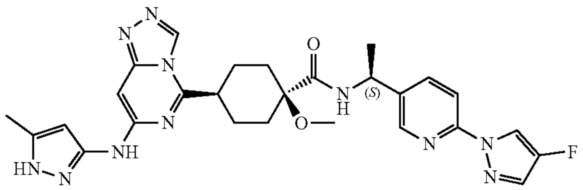
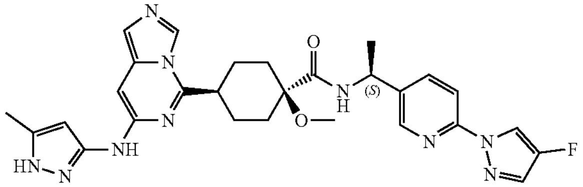
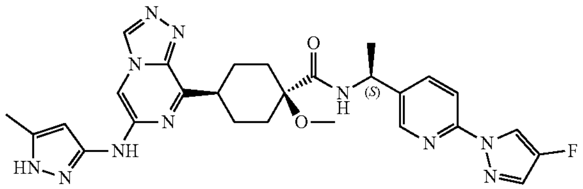
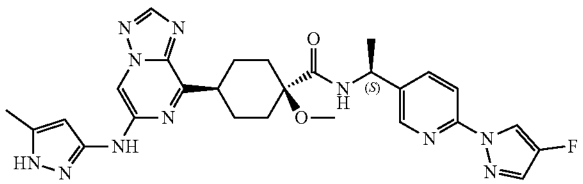
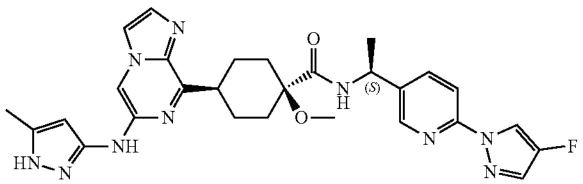
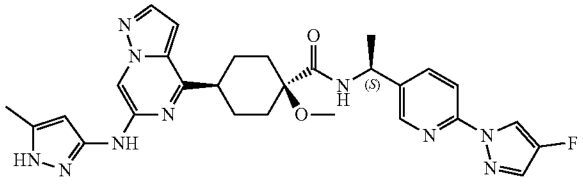

-continued
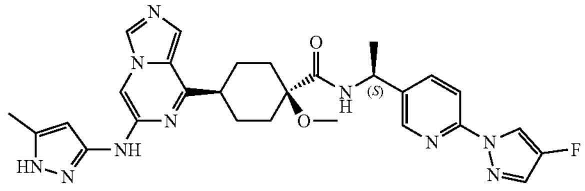
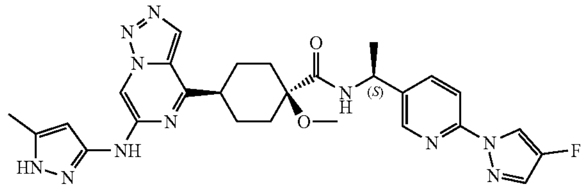
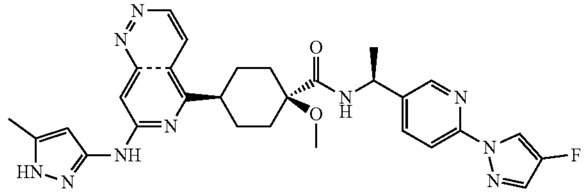
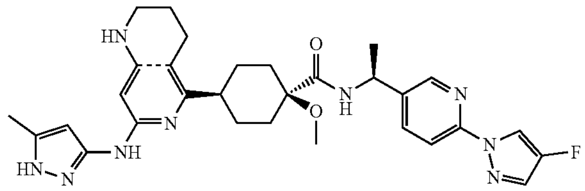
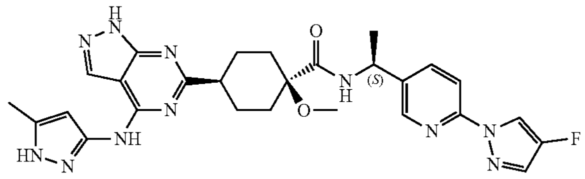
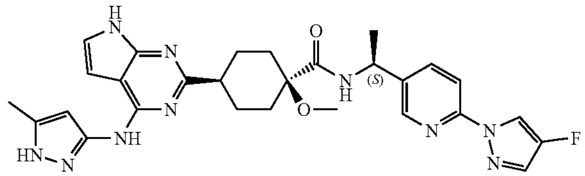
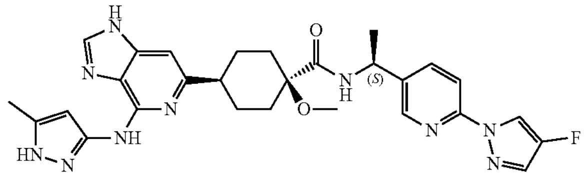
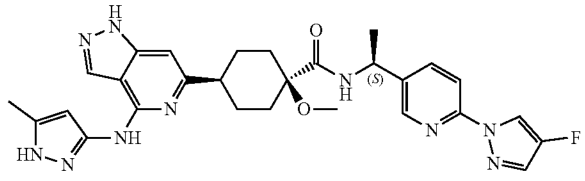
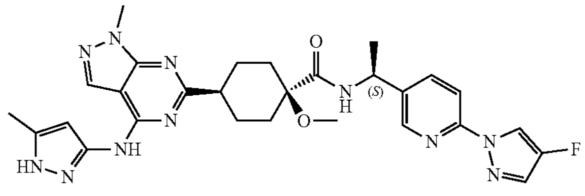
-continued
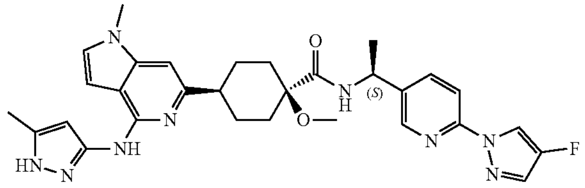
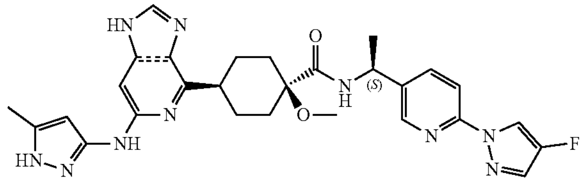
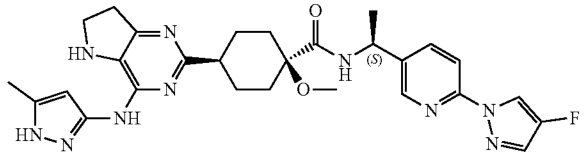
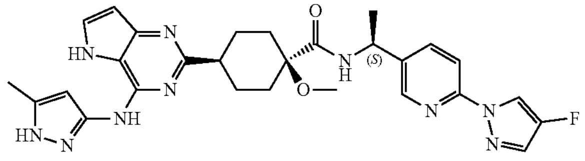
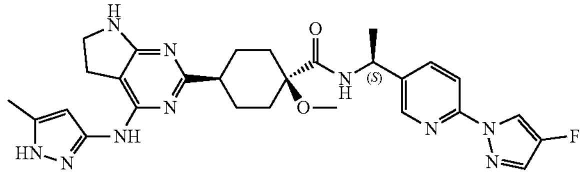
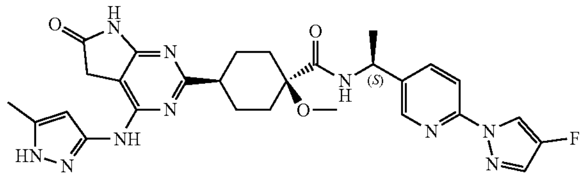
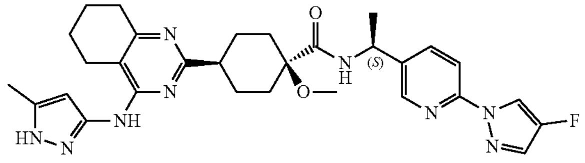
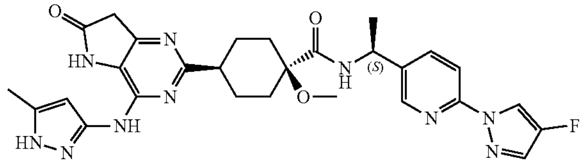
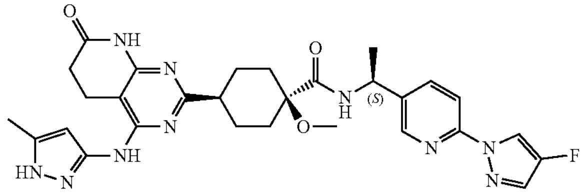
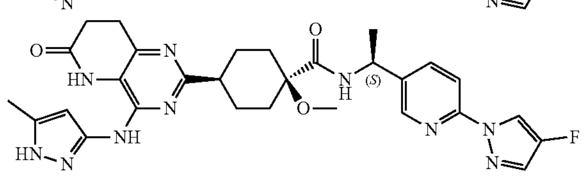

-continued

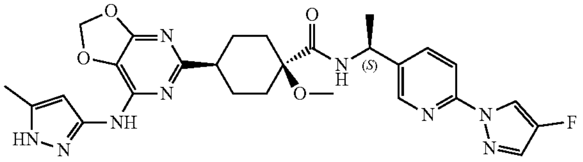

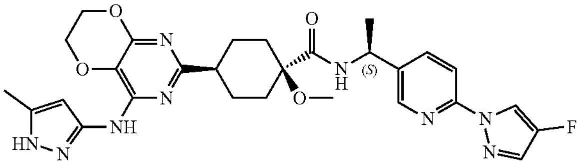

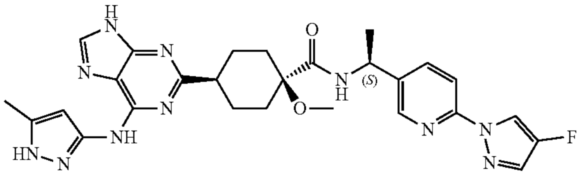

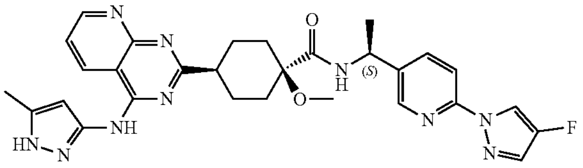

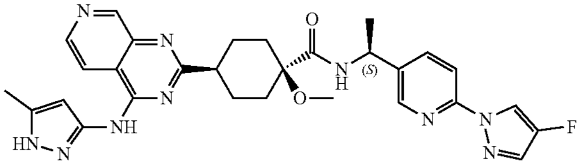

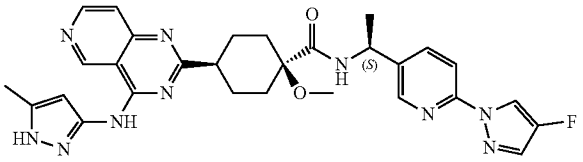

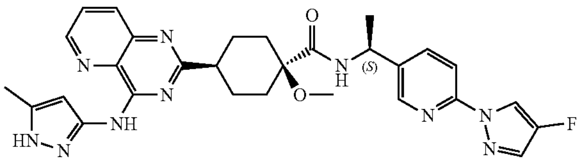

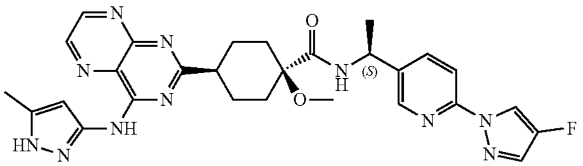

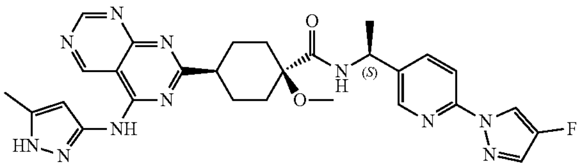

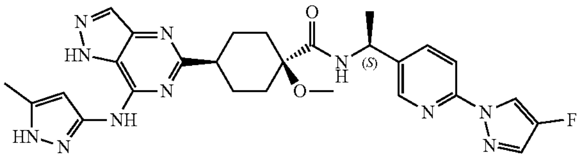

-continued

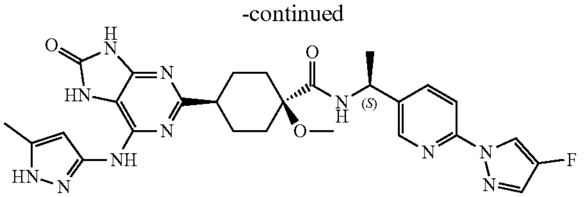

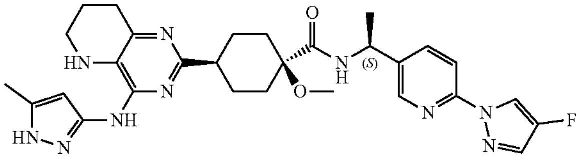

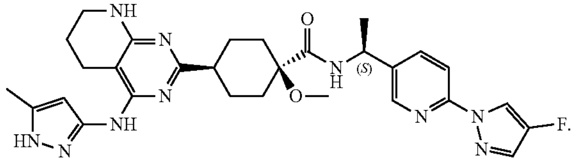

In another preferred embodiment, the compound is selected from the compounds shown in the Example.

In another preferred embodiment, the compound, or the pharmaceutically acceptable salt, stereoisomer, solvate or prodrug thereof, wherein the pharmaceutically acceptable salt is an inorganic acid salt or an organic acid salt, wherein the inorganic acid salt is selected from hydrochloride, hydrobromide, hydroiodide, sulfate, bisulfate, nitrate, phosphate or acid phosphate; the organic acid salt is selected from formate, acetate, trifluoroacetate, propionate, pyruvate, hydroxyacetate, oxalate, malonate, fumarate, maleate, lactate, malate, citrate, tartrate, methanesulfonate, ethanesulfonate, benzenesulfonate, salicylate, picrate, glutamate, ascorbate, camphorate, or camphor sulfonate.

In the second aspect of the invention, a pharmaceutical composition comprising a therapeutically effective amount of the compound of formula I' of the first aspect, or the pharmaceutically acceptable salt, stereoisomer, solvate or prodrug thereof, and a pharmaceutically acceptable carrier is provided.

In another preferred embodiment, the pharmaceutical composition may also comprise one or more other therapeutic agents, and the other therapeutic agents are selected from: PD-1 inhibitor (such as nivolumab, pembrolizumab, JS-001, SHR-120, BGB-A317, IBI-308, GLS-010, GB-226, STW204, HX008, HLX10, BAT 1306, AK105, LZM 009 or the biological analogue thereof, etc.), PD-L1 inhibitor (such as durvalumab, atezolizumab, CS1001, KN035, HLX20, SHR-1316, BGB-A333, JS003, CS1003, KL-A167, F 520, GR1405, MSB2311 or the biological analogue thereof, etc.), CD20 antibody (such as rituximab, obinutuzumab, ofatumumab, tositumomab, ibritumomab, etc.), CD47 antibody (such as Hu5F9-G4, CC-90002, TTI-621, TTI-622, OSE-172, SRF-231, AIX-148, NI-1701, SHR-1603, IBI188, IMM01), ALK inhibitor (such as Ceritinib, Alectinib, Brigatinib, Lorlatinib, Ocatinib), PI3K inhibitor (such as Idelalisib, Dactolisib, Taselisib, Buparlisib, etc.), BTK inhibitor (such as Ibrutinib, Tirabrutinib, Acalabrutinib, etc.), EGFR inhibitor (such as Afatinib, Gefitinib, Erlotinib, Lapatinib, Dacomitinib, Icotinib, Canertinib, etc.), VEGFR inhibitor (such as Sorafenib, Pazopanib, Regorafenib, Cabozantinib, Sunitinib, Donafenib, etc.), HDAC inhibitor (such as Givinostat, Droxinostat, Entinostat, Dacinostat, Tacedinaline, etc.), CDK inhibitor (such as Palbociclib, Ribociclib, Abemaciclib, Lerociclib, etc.), MEK inhibitor (such as Selumetinib (AZD6244), Trametinib (GSK1120212), PD0325901, U0126, AS-703026, PD184352 (CI-1040), etc.), mTOR inhibitor (such as Vistusertib, etc.), SHP2 inhibitor (such as RMC-4630, JAB-3068, TNO 155, etc.), IGF-1R inhibitor (such as Ceritinib, Okatinib, linsitinib, BMS-754807, GSK1838705A, etc.) or combinations thereof.

In the third aspect of the invention, a use of the compound of formula I' of the first aspect, or the pharmaceutically acceptable salt, stereoisomer, solvate or prodrug thereof in the preparation of a medicament used as a RET kinase inhibitor is provided.

In the fourth aspect of the invention, a use of the compound of formula I' of the first aspect, or the pharmaceutically acceptable salt, stereoisomer, solvate or prodrug thereof, in the preparation of a medicament for modulating RET kinase activity or for the treatment of RET-related diseases is provided.

In another preferred embodiment, the RET-related diseases include cancer.

In another preferred embodiment, the cancer is thyroid cancer or lung cancer.

In another preferred embodiment, the cancer is medullary thyroid carcinoma or non-small cell lung cancer.

DETAILED DESCRIPTION OF THE INVENTION

After extensive and in-depth research, the inventor unexpectedly discovered a class of compounds with excellent RET kinase inhibitory activity. In addition, the compounds have excellent inhibitory activity against RET kinase and have better pharmacodynamic/pharmacokinetic properties. On this basis, the present invention was completed.

Term

Unless otherwise stated, the following terms used in this application (including the specification and claims) have the definitions given below.

When a substituent is described by a conventional chemical formula written from left to right, the substituent also includes a chemically equivalent substituent obtained by writing a structural formula from right to left. For example, $—CH_2O—$ is equivalent to $—OCH_2—$.

"Alkyl (alone or as part of other groups)" refers to a monovalent linear or branched saturated hydrocarbon group containing 1 to 12 carbon atoms composed only of carbon and hydrogen atoms. The alkyl is preferably C1-C6 alkyl (i.e. containing 1, 2, 3, 4, 5 or 6 carbon atoms). Examples of alkyl include but are not limited to methyl, ethyl, propyl, isopropyl, isobutyl, sec-butyl, tert-butyl, amyl, n-hexyl, octyl and dodecyl etc. In the present application, alkyl is also intended to comprise a substituted alkyl, i.e. one or more positions in the alkyl are substituted, in particular 1-4 substituents, which may be substituted at any position. "Haloalkyl" refers to an alkyl as defined herein in which one or more hydrogen is replaced by the same or different halogens. Examples of haloalkyl include $—CH_2Cl$, $—CH_2CF_3$, $—CH_2CCl_3$, perfluoroalkyl (e.g. $—CF_3$), etc.

"Alkylene" refers to divalent group of alkyl, e.g. $—CH_2—$, $—CH_2CH_2—$ and $—CH_2CH_2CH_2—$.

"Alkoxy (alone or as part of other groups)" refers to alkyl to which an oxy is attached with a formula alkyl O—, wherein the alkyl has the definition described above, and preferably the alkoxy is C1-C6 alkoxy. Alkoxy includes but is not limited to methoxy, ethoxy, propoxy, tert-butoxy, etc. "Haloalkoxy" refers to the formula —OR, wherein, R is a halogenated alkyl as defined herein. Examples of haloalkoxy include but are not limited to trifluoromethoxy, difluoromethoxy, and 2,2,2-trifluoroethoxy, etc.

"Thioalkyl" refers to that the carbon in the alkyl is substituted by S, S(O) or S(O)2.

"Alkenyl (alone or as part of other groups)" refers to aliphatic group containing at least one double bond, typically having between 2 and 20 carbon atoms. In the present invention, "C2-C6 alkenyl" refers to alkenyl containing 2, 3, 4, 5 or 6 carbon atoms. The alkenyl includes but is not limited to, for example, vinyl, propenyl, butenyl, 1-methyl-2-buten-1-yl, etc. In the present invention, the alkenyl includes substituted alkenyl.

"Alkenylene" refers to alkenyl having two connection points. For example, "vinylidene" refers to the group —CH═CH—. The alkenylene may also be in an unsubstituted form or in a substituted form having one or more substituents.

"Alkynyl (alone or as part of other groups)" refers to a straight or branched hydrocarbon chain containing more than 2 carbon atoms and characterized by one or more triple bonds, typically having 2 to 20 carbon atoms. In the present invention, "C2-6 alkynyl" refers to alkynyl having 2, 3, 4, 5 or 6 carbon atoms. Alkynyl includes but is not limited to ethynyl, propargyl and 3-hexynyl. One of the triple-bond carbons can optionally be the connection point of alkynyl substituent. In the invention, the alkynyl also includes substituted alkynyl.

"Alkynylene" refers to alkynyl having two connecting points. For example, "ethynylene" refers to the group: —C≡C—. The alkynylene may also be in an unsubstituted form or in a substituted form having one or more substituents.

"Aliphatic group" refers to straight-chain, branched or cyclic hydrocarbon group including saturated and unsaturated group, such as alkyl, alkenyl and alkynyl.

"Aromatic ring system" refers to monocyclic, bicyclic or polycyclic hydrocarbon ring system in which at least one ring is aromatic.

"Aryl (alone or as part of other groups)" refers to a monovalent group of an aromatic ring system. Representative aryl include all aromatic ring systems, such as phenyl, naphthyl and anthryl; and ring systems in which aromatic carbocyclic rings are fused with one or more non-aromatic carbocyclic rings, such as indanyl, phthalimide, naphthylimide or tetrahydronaphthyl, etc. In the present invention, the aryl is preferably C6-C12 aryl. In the present invention, aryl is also intended to comprise substituted aryl.

"Arylalkyl" or "aralkyl" refers to an alkyl moiety in which the alkyl hydrogen atom is substituted by an aryl. An aralkyl includes a group in which one or more hydrogen atoms are substituted by aryl, wherein aryl and alkyl are as defined above. Examples of "arylalkyl" or "aralkyl" include benzyl, 2-phenylethyl, 3-phenylpropyl, 9-fluorenyl, diphenylmethyl and tritylmethyl, etc.

"Aryloxy" refers to —O-(aryl), wherein the aryl moiety is as defined herein.

"Heteroalkyl" refers to a substituted alkyl having one or more skeleton chain atoms selected from atoms other than carbon, such as oxygen, nitrogen, sulfur, phosphorus, or a combination thereof. Numeric ranges may be given for example C1-C6 heteroalkyl refers to the number of carbons in the chain which includes 1 to 6 carbon atoms. For example, $—CH_2OCH_2CH_3$ is called "C3" heteroalkyl. The connection with the rest of the molecule can be through heteroatoms or carbons in heteroalkyl chain. "Heteroalkylene" refers to an optionally substituted divalent alkyl having one or more skeleton chain atoms selected from atoms other than carbon, such as oxygen, nitrogen, sulfur, phosphorus, or a combination thereof.

"Carbocyclic system" refers to a monocyclic, dicyclic or polycyclic hydrocarbon ring system in which each ring is fully saturated or contains one or more unsaturated units, but none of the rings are aromatic.

"Carbocyclic group" refers to a monovalent group of a carbocyclic system. These include, for example, cycloalkyl (cyclopentyl, cyclobutyl, cyclopropyl, cyclohexyl, etc.) and cycloalkenyl (e.g. cyclopentenyl, cyclohexenyl, cyclopentadienyl, etc.).

"Cycloalkyl" refers to a monovalent saturated carbocyclic group consisting of monocyclic or dicyclic ring having 3-12, preferably 3-10, more preferably 3-6 ring atoms. The cycloalkyl may optionally be substituted with one or more substituents, wherein each substituent is independently a hydroxyl, alkyl, alkoxy, halogen, haloalkyl, amino, monoalkylamino or dialkylamino. Examples of cycloalkyl include but are not limited to cyclopropyl, cyclobutyl, cyclopentyl, cyclohexyl and cycloheptyl, etc.

"Cycloalkoxy" refers to the formula —OR, wherein R is a cycloalkyl as defined herein. Examples of cycloalkyloxy include cyclopropyloxy, cyclobutyloxy, cyclopentyloxy and cyclohexyloxy, etc. "Cycloalkyl alkyl" means -(cycloalkyl)-alkyl in which cycloalkyl and alkyl are as disclosed herein. "Cycloalkyl alkyl" is bonded to the parent molecular structure by a cycloalkyl.

"Heteroaromatic ring system" refers to a monocyclic (e.g. 5 or 6 membered), dicyclic (6-12 membered), or polycyclic system in which at least one ring is both aromatic and contains at least one heteroatom (e.g. N, O, or S); and none of the other rings are heterocyclyl (as defined below). In some cases, rings that are aromatic and contain heteroatoms contain 1, 2, 3 or 4 ring heteroatoms in the ring. At least one ring is heteroaromatic, and the remaining rings may be saturated, partially unsaturated or completely unsaturated.

"Heteroaryl" refers to a monocyclic (e.g. 5 or 6 membered), dicyclic (e.g. 8-10 membered) or tricyclic group with 5 to 12 ring atoms, and it contains at least one aromatic ring containing 1, 2 or 3 cyclic heteroatoms selected from N, O or S, and the remaining ring atoms are C. It should be clear that the connection point of the heteroaryl should be located on the aromatic ring. Examples of heteroaryl include but are not limited to imidazolyl, aoxazolyl, isoxazolyl, thiazolyl, isothiazolyl, oxadiazolyl, thiadiazolyl, pyrazinyl, thienyl, furanyl, pyranyl, pyridyl, pyrrolyl, pyrazolyl, pyrimidinyl, quinolinyl, isoquinolinyl, benzofuranyl, benzothienyl, benzothiopyranyl, benzimidazolyl, benzoxazolyl, benzoxadiazolyl, benzothiazolyl, benzothiadiazolyl, benzopyranyl, indolyl, isoindolyl, triazolyl, triazinyl, quinoxalinyl, purinyl, quinazolinyl, quinazinyl, naphthyridinyl, pterridinyl, carbazolyl, azepinyl, diazepinyl and acridinyl, etc. Heteroarylene refers to heteroaryl having two connecting points.

"Heterocyclic system" refers to monocyclic, bicyclic and polycyclic systems where at least one ring is saturated or partially unsaturated (but not aromatic) and the ring contains at least one heteroatom. The heterocyclic system can be attached to the side group of any heteroatom or carbon atom to produce a stable structure and any ring atom can be optionally substituted.

"Heterocyclyl" refers to a monovalent group of a heterocyclic system. It usually refers to stable monocyclic (such as 3-8 membered, i.e. 3 membered, 4 membered, 5 membered, 6 membered, 7 membered or 8 membered) or bicyclic (such as 5-12 membered, i.e. 5 membered, 6 membered, 7 membered, 8 membered, 9 membered, 10 membered, 11 membered or 12 membered) or polycyclic (such as 7-14 membered, i.e. 7 membered, 8 membered, 9 membered, 10 membered, 11 membered, 12 membered, 13 membered or 14 membered), including fused ring, spiro ring and/or bridge ring structure, which is saturated and partially unsaturated and contains carbon atoms and 1, 2, 3 or 4 heteroatoms independently selected from N, O or S. Representative heterocyclyl include the following ring systems, where (1) each ring is non-aromatic and at least one ring contains a heteroatom, for example, tetrahydrofuryl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl and quinuclidinyl; (2) at least one ring is non-aromatic and contains heteroatoms and at least one other ring is an aromatic carbocyclic ring, for example, 1,2,3,4-tetrahydroquinolinyl, 1,2,3,4-tetrahydroisoquinolinyl; and (3) at least one ring is non-aromatic and contains a heteroatom and at least one other ring is aromatic and contains a heteroatom, for example, 3,4-dihydro-1H-pyrano[4,3-c] pyridine and 1,2,3,4-tetrahydro-2,6-naphthyridine. Heterocyclylene refers to heterocyclyl having two connecting points. In the present invention, the heterocyclylene is preferably bicyclic, wherein one ring is a heteroaryl and connected to the other parts of the general formula through the heteroaryl. In the present invention, the heterocyclylene is preferably a 5-6-membered monocyclic heterocyclylene or an 8-10-membered bicyclic heterocyclylene.

"Heterocyclyl alkyl" refers to an alkyl substituted with a heterocyclyl, wherein the heterocyclyl and alkyl are as defined above.

"Alkylamino" refers to a group having a structure of alkyl-NR—, where R is H, or an alkyl, cycloalkyl, aryl, heteroaryl, etc. are as described above.

"Cycloalkylamino" refers to the formula —NRaRb, wherein Ra is H, an alkyl as defined herein or a cycloalkyl as defined herein, and Rb is a cycloalkyl as defined herein; or Ra and Rb together with their attached N atoms form a 3-10-membered N-containing monocyclic or bicyclic heterocyclyl, such as tetrahydropyrrolyl. As used herein, C3-C8 cycloalkylamino refers to an amino containing 3-8 carbon atoms.

As used herein, an "ester" refers to —C(O)—O—R or R—C(O)—O—, wherein R independently represents hydrogen, alkyl, cycloalkyl, aryl, heteroaryl, heterocyclyl are as defined above.

As used herein, the term "amide" refers to a group with a structure of —CONRR', wherein R and R' independently represent hydrogen, alkyl or substituted alkyl, cycloalkyl or substituted cycloalkyl, aryl or substituted aryl, heterocyclyl or substituted heterocyclyl with the definitions as described above. R and R' may be the same or different in the dialkylamino segments.

As used herein, the term "sulfonamide" refers to a group with a structure of $—SO_2NRR'$, wherein R and R' independently represent hydrogen, alkyl or substituted alkyl, cycloalkyl or substituted cycloalkyl, aryl or substituted aryl, heterocyclyl or substituted heterocyclyl with the definitions as described above. R and R' may be the same or different in the dialkylamino segments.

"Ketocarbonyl" refers to R—C(═O)—, wherein R is alkyl, cycloalkyl, etc. with the definitions as described above.

When the substituent is a non-terminal substituent, it is a subunit of the corresponding substituent, such as alkyl corresponding to alkylene, cycloalkyl corresponding to cycloalkylene, heterocyclyl corresponding to heterocyclylene, alkoxy corresponding to alkyleneoxy, etc.

In the present invention, each of the above-mentioned groups of alkyl, alkoxy, cycloalkyl, heteroalkyl, aryl, heteroaryl, cycloheteroalkyl, alkenyl, alkynyl, heterocycle, heterocyclyl, etc. may be substituted or unsubstituted.

As used herein, the term "substituted" refers to the substitution of one or more hydrogen atoms on a specific group by specific substituent. The specific substituents are those described in the preceding paragraph or those present in each Example. Unless otherwise specified, a substituted group may have a substituent selected from a specific group at any substitutable position of the group, and the substituent may be the same or different in each position. Those skilled in the art should understand that the combinations of substituents contemplated by the present invention are those that are stable or chemically achievable. Typical substituents include but are not limited to one or more of the following groups: such as hydrogen, deuterium, halogen (such as monohalogenated substituent or polyhalogenated substituents, and the latter such as trifluoromethyl or alkyl containing $Cl_3$), cyano, nitro, oxo (=O), trifluoromethyl, trifluoromethoxy, cycloalkyl, alkenyl, alkynyl, heterocycle, aromatic ring, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$ or $NR_bP(=O)_2R_e$, wherein $R_a$ can independently represent hydrogen, deuterium, alkyl, cycloalkyl, alkenyl, alkynyl, heterocycle or aromatic ring, $R_b$, $R_c$ and $R_d$ can independently represent hydrogen, deuterium, alkyl, cycloalkyl, heterocycle or aromatic ring, or $R_b$ and $R_c$ together with the N atom form a heterocycle, $R_e$ can independently represent hydrogen, alkyl, cycloalkyl, alkenyl, alkynyl, heterocycle or aromatic ring. The above typical substituents, such as alkyl, cycloalkyl, alkenyl, cycloalkenyl, alkynyl, heterocyclyl or aromatic ring can be optionally substituted. The substituent is such as (but is not limited to): halogen, hydroxy, cyano, carboxy (—COOH), C1-C6 alkyl, C2-C6 alkenyl, C2-C6 alkynyl, C3-C8 cycloalkyl, 3- to -12 membered heterocyclyl, aryl, heteroaryl, C1-C8 aldehydyl, C2-C10 acyl, C2-C10 ester, amino, C1-C6 alkoxy, C1-C10 sulfonyl, and C1-C6carbamido, etc.

"Cyano" refers to —CN.

"Nitro" refers to $—NO_2$.

"Hydroxyl" refers to —OH.

"Amino" refers to $—NH_2$ or RNH—, wherein R is keto-carbonyl, sulfonyl, sulfonamide, $R^a—C(=O)—$, $R_aR_bN—C(=O)—$ and so on, wherein $R_a$ and $R_b$ is alkyl, cycloalkyl, aryl or heteroaryl, etc.

"Halogen (halogenated)" refers to any halogen group, e.g. —F, —Cl, —Br or —I.

"Deuterated compound" refers to the compound obtained by replacing one hydrogen atom (H) or multiple hydrogen atoms (H) with deuterium atoms (D) in a compound.

In the present invention, the term "multiple" independently refers to 2, 3, 4 or 5.

Active Ingredient

As used herein, the terms "compounds of the invention" or "active ingredients of the invention" are used interchangeably and refer to compounds of formula I', or pharmaceutically acceptable salt, hydrate, solvate, isotope compound (e.g. deuterated compound) or prodrug thereof. The term also includes racemate and optical isomer.

The compound of formula I' has the following structure:

I'

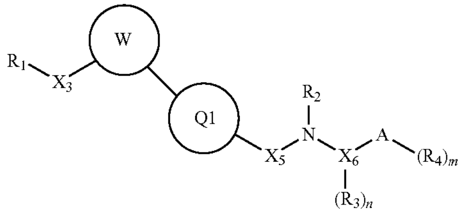

$R_1$, $X_3$, W, Q1, $X_5$, $X_6$, $R_2$, $R_3$, $R_4$, A, m and n are defined as above, preferably the W ring is substituted or unsubstituted substitutents selected from the group consisting of 5-6-membered monocyclic heterocyclylene, 8-10-membered bicyclic heterocyclylene or 5-6-membered monocyclic heteroarylene or 8-10-membered bicyclic heteroarylene; the "substituted" means optionally substituted by 0-2 $R_5$; $R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, aryl, heteroaryl, aryloxy, aralkyl, heterocyclyl, heterocycloalkyl, nitro, oxo, cyano, $—C(O)R_6$, $—OC(O)R_6$, $—C(O)OR_6$, —(C1-C6 alkylene)-$C(O)R_6$, $—SR_6$, $—S(O)_2R_6$, $—S(O)_2—N(R_6)(R_7)$, —(C1-C6 alkylene)-$S(O)_2R_6$, —(C1-C6 alkylene)-$S(O)_2—N(R_6)(R_7)$, $—N(R_6)(R_7)$, $—C(O)—N(R_6)(R_7)$, $—N(R_6)—C(O)R_7$, $—N(R_6)—C(O)OR_7$, —(C1-C6 alkylene)-$N(R_6)—C(O)R_7$, $—N(R_6)S(O)_2R_7$ or $—P(O)(R_6)(R_7)$; wherein alkyl, alkenyl, alkynyl, alkoxy, alkylamino, heteroalkyl, cycloalkyl, aryl, heteroaryl, aryloxy, aralkyl, heterocyclyl and heterocycloalkyl are each independently substituted by 0-5 $R^a$; $R^a$ is optionally selected from C1-C6 alkyl, halogen, hydroxy, C1-C6 heteroalkyl, C1-C6 alkoxy, C1-C6 alkylamino, cycloalkyl heterocycloalkyl or cyano, more preferably, W ring is selected from

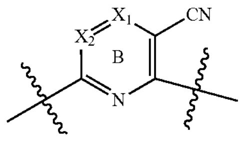
,
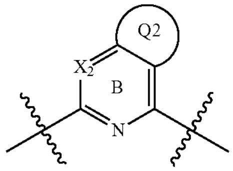

(or
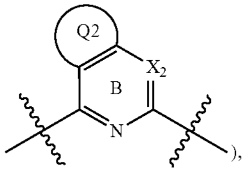
),

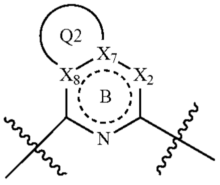
(or
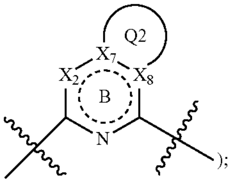
);

wherein, $X_1$, $X_2$, $X_7$, $X_8$ and Q2 are defined as above, and at least one of $X_7$ and $X_8$ is N.

Preferably, the compound of formula I', or the pharmaceutically acceptable salt, stereoisomer, solvate or prodrug thereof has the structure represented by formula (II), formula (III) or formula (IV), (II)

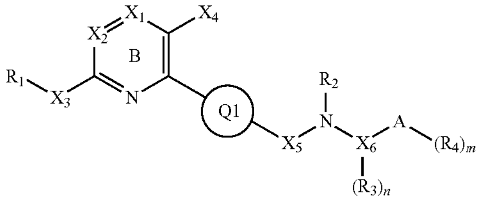

(III)

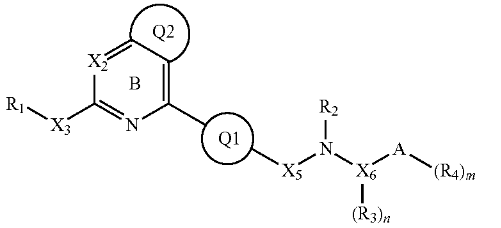

(IV)

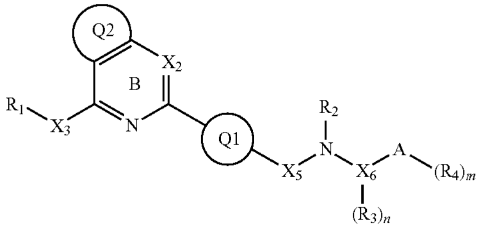

wherein, $R_1$, $X_1$, $X_2$, $X_3$, Q1, Q2, $X_5$, $X_6$, $R_2$, $R_3$, $R_4$, A, m, and n are defined as above.

Preferably, the compound of formula I', or the pharmaceutically acceptable salt, stereoisomer, solvate or prodrug thereof has the structure represented by formula (2), formula (3) or formula (4), (2)

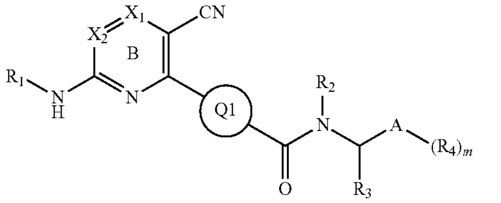

(3)

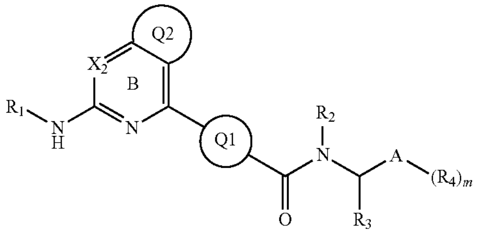

(4)

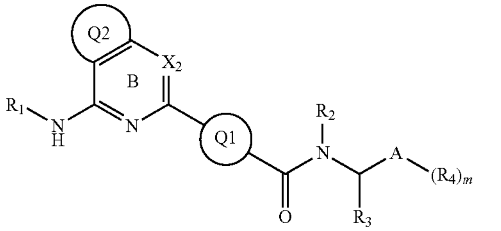

wherein $R_1$, $X_1$, $X_2$, Q1, Q2, $R_2$, $R_3$, $R_4$, A and m are defined as above.

Preferably, the compound, or the pharmaceutically acceptable salt, stereoisomer, solvate or prodrug thereof has the structure represented by formula 2',

2'

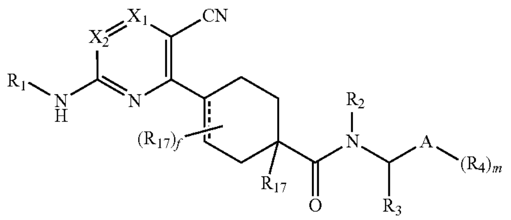

wherein, ═ is a single bond or a double bond;

$X_1$, $X_2$, $R_1$, $R_2$, $R_3$, $R_4$, A, $R_{17}$, f and m are defined as above.

Preferably, the compound, or the pharmaceutically acceptable salt, stereoisomer, solvate or prodrug thereof has the structure represented by formula 2"

2"

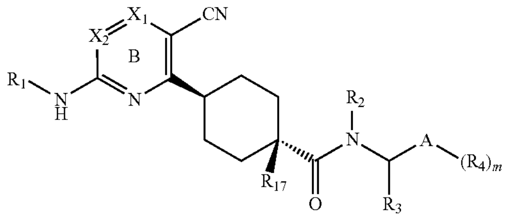

wherein, $X_1$, $X_2$, $R_1$, $R_2$, $R_3$, $R_4$, A, m and $R_{17}$ are defined as above.

Preferably, the compound of formula I', or the pharmaceutically acceptable salt, stereoisomer, solvate or prodrug thereof has the structure represented by formula 3',

3'

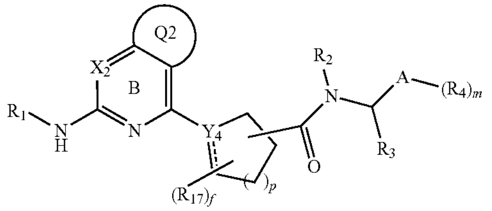

wherein, ═ is a single bond or a double bond;

when ═ is a single bond, $Y_4$ is selected from N or $CR_{17}$, when ═ is a double bond, $Y_4$ is C;

$R_1$, $X_2$, $R_2$, $R_3$, $R_4$, $R_{17}$, A, m, f, p and Q2 are defined as above.

In another preferred embodiment, the compound of formula I', or the pharmaceutically acceptable salt, stereoisomer, solvate or prodrug thereof has the structure represented by formula 3',

3″

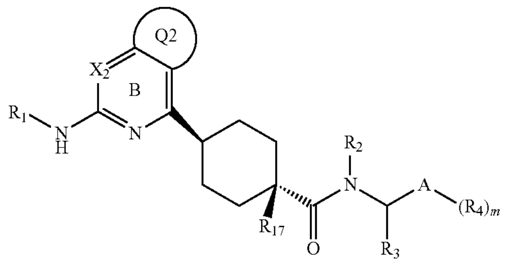

$R_1$, $X_2$, $R_2$, $R_3$, $R_4$, A, Q2, m and $R_{17}$ are defined as above.

Preferably, the compound of formula I', or the pharmaceutically acceptable salt, stereoisomer, solvate or prodrug thereof has the structure represented by formula 4',

4′

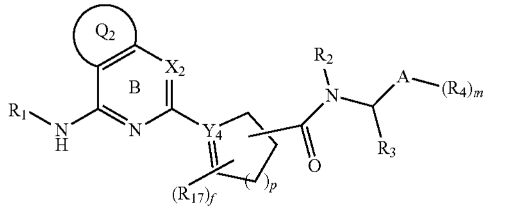

wherein, ═ is a single bond or a double bond;

when ═ is a single bond, $Y_4$ is selected from N or $CR_{17}$, when ═ is a double bond, $Y_4$ is C;

$R_1$, $X_2$, $R_2$, $R_3$, $R_4$, $R_{17}$, A, m, f, p and Q2 are defined as above.

Preferably, the compound of formula I', or the pharmaceutically acceptable salt, stereoisomer, solvate or prodrug thereof has the structure represented by formula 4",

4″

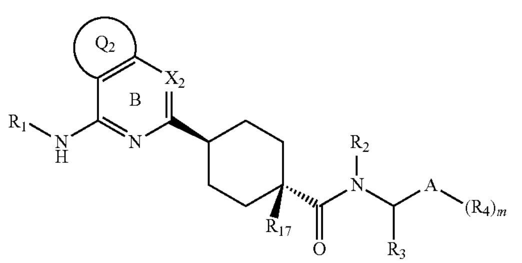

$R_1$, $X_2$, $R_2$, $R_3$, $R_4$, A, Q2, m and $R_{17}$ are defined as above.

Preferably, the compound of formula I', or the pharmaceutically acceptable salt, stereoisomer, solvate or prodrug thereof has the structure represented by formula 5 or formula 6,

5

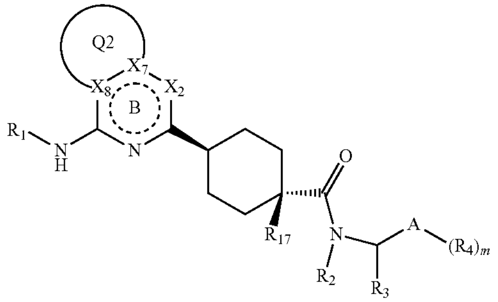

6

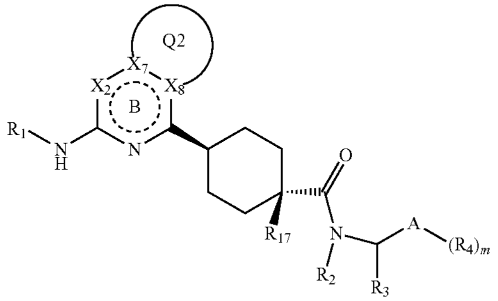

wherein $R_1$, $X_7$, $X_8$, $X_2$, Q2, $R_2$, $R_3$, $R_4$, $R_{17}$, A and m are defined as above, and at least one of $X_7$, $X_8$ is N.

Preferably, in the above each formula, $R_1$ is optionally selected from one of the following structures:

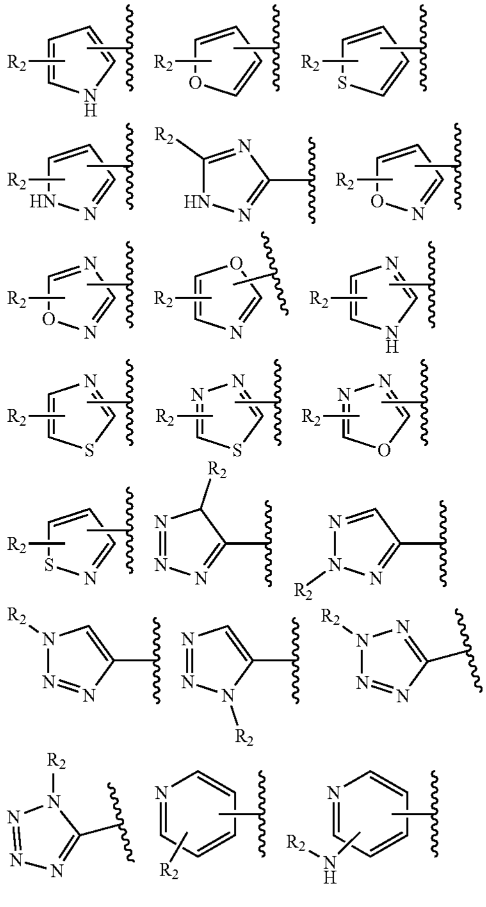

-continued

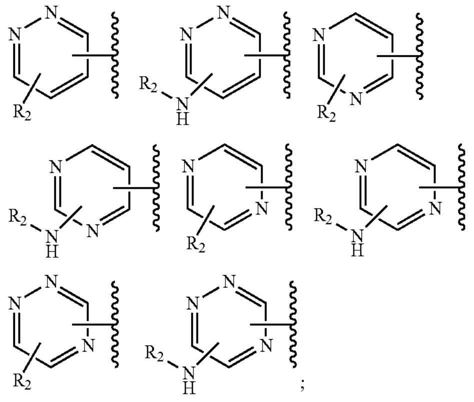

;

more preferably $R_1$ is

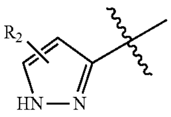

;

$R_2$ is optionally selected from hydrogen, C1-C6 alkyl, C1-C6 alkoxy, C3-C6 cycloalkyl, or C1-C6 heteroalkyl, wherein alkyl, alkoxy, cycloalkyl and heteroalkyl are each optionally and independently substituted by 0-5 $R^a$;

$R^a$ is optionally selected from C1-C6 alkyl, halogen, hydroxy, C1-C6 heteroalkyl, C1-C6 alkoxy, cycloalkyl, heterocycloalkyl or cyano.

Preferably, in the above each formula, the W ring is selected from

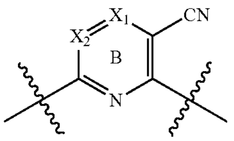

,

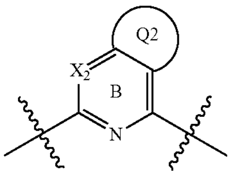

(or

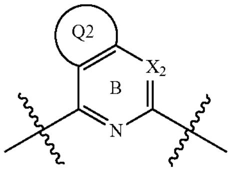

) or

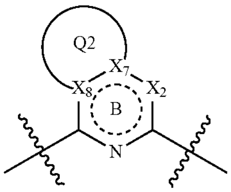

(or

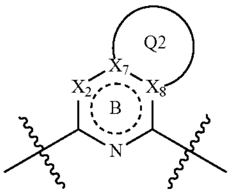

);

wherein,

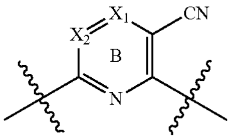

is selected from

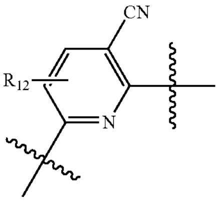

,

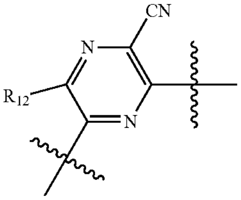

or

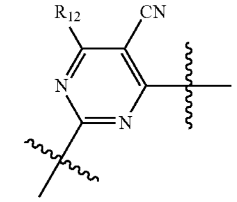

;

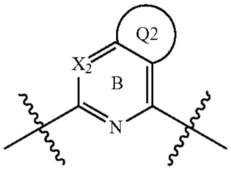

(or

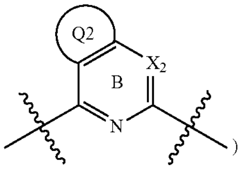

)

is selected from

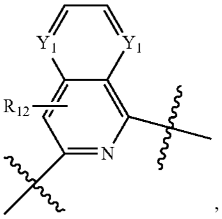

,

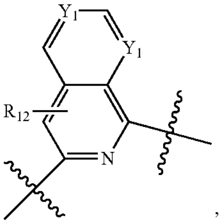

,

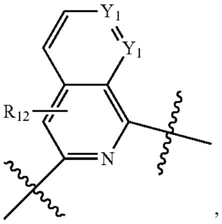

,

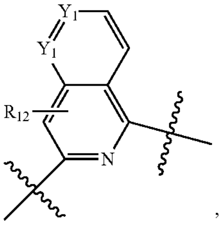

,

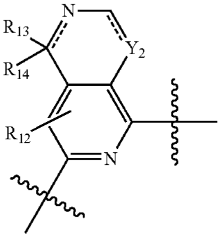

,

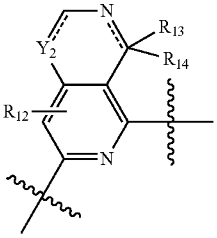

,

-continued
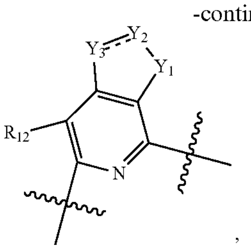
,
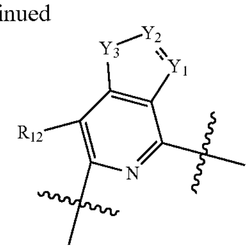
,
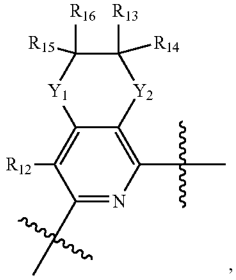
,
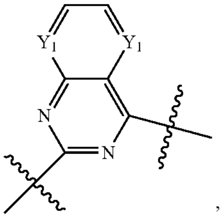
,
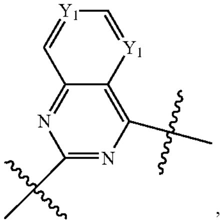
,
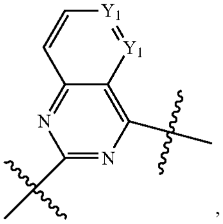
,
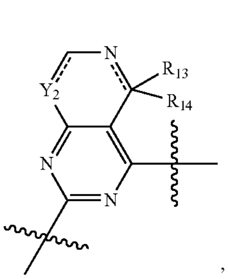
,
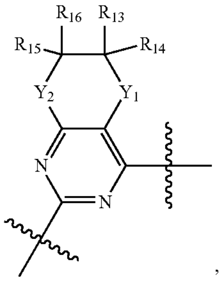
,
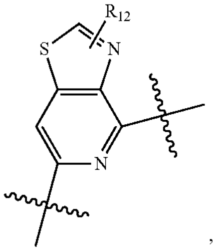
,
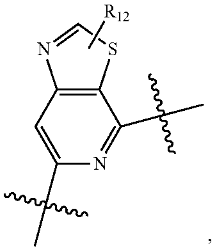
,
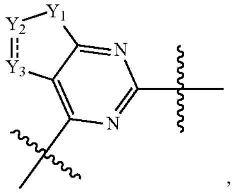
,
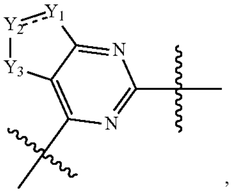
,
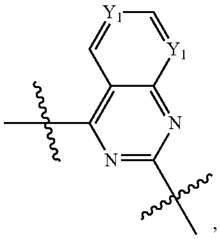
,
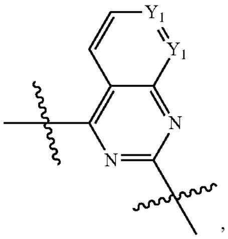
, or
-continued
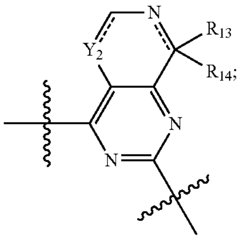
preferably
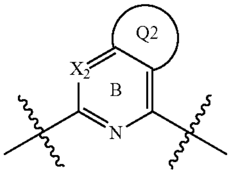
(or
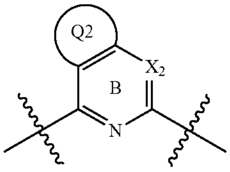
)
is selected from
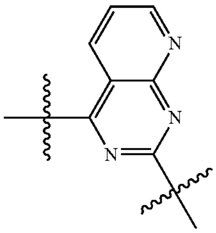
,
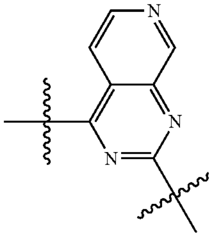
,
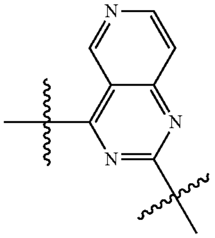
or
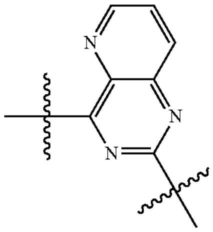
;
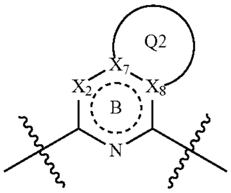
(or
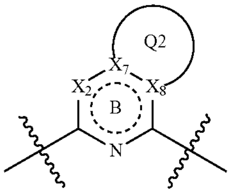
)
is selected from
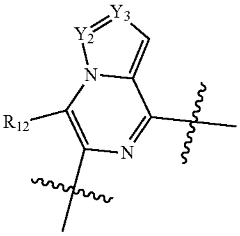
, -continued

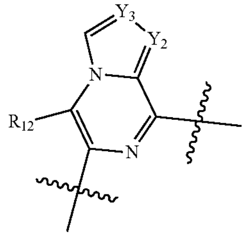

,

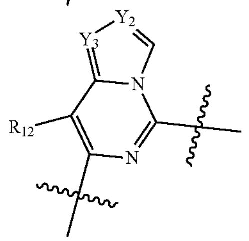

,

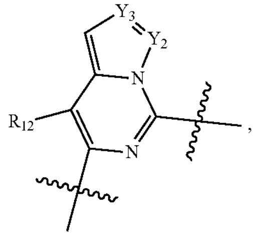

,

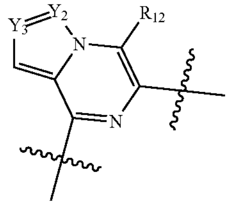

,

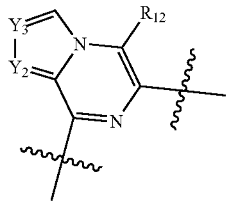

,

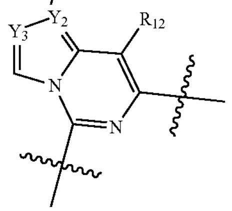

or

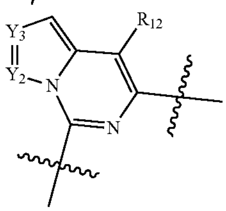

;

wherein, ═ is a single bond or a double bond;

$R_{12}$ is independently selected from H, halogen, C1-C6 alkyl, C1-C6 alkoxy, nitro, cyano or amino;

$Y_1$, $Y_2$ and $Y_3$ are each independently selected from O, N, $NR_{17}$, $CR_{13}$ or $CR_{13}R_{14}$;

$R_{13}$, $R_{14}$, $R_{15}$ and $R_{16}$ are each independently selected from H, halogen, C1-C6 alkyl, C1-C6 alkoxy, C1-C6 alkylamino, nitro, cyano, or amino; or $R_{13}$ and $R_{14}$ together with the C atom attached to them form a carbonyl (C═O); or $R_{15}$ and $R_{16}$ together with the C atom attached to them form a carbonyl (C═O);

$R_{17}$ is selected from H or C1-C6 alkyl.

Preferably, in the above each formula, A is aromatic ring or heteroaromatic ring, and more preferably, A is phenyl, pyridyl, pyrazinyl, pyrimidyl or pyridazinyl; the heteroaromatic ring contains 0-3 heteroatoms optionally selected from N, O or S; any hydrogen atom in the A ring may be substituted by deuterium, hydroxy, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl or heteroaryl.

Preferably, in the above each formula, $R_4$ is each independently selected from aryl, heteroaryl, aryloxy, aralkyl, or heterocyclyl, and more preferably $R_4$ is 5-membered heteroaryl; wherein aryl, heteroaryl, aryloxy, aralkyl, heterocyclyl, and heterocycloalkyl are each independently substituted by 0 to 5 $R^a$; $R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano more preferably $R_4$ is selected from:

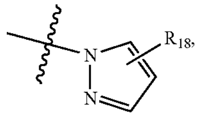

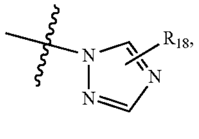

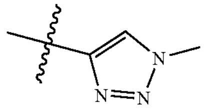

or

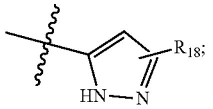

wherein $R_{18}$ is selected from halogen (preferably F) or C1-C6 alkyl.

Preferably, in the above each formula, m is 1.

Preferably, in the above each formula, $R_3$ is H, C1-C6 alkyl or C1-C6 alkoxy.

Preferably, in the above each formula, $R_2$ is H.

Preferably, in the above each formula,

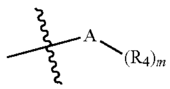

is

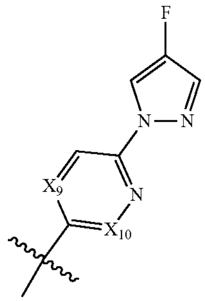

, wherein $X_9$ and $X_{10}$ are each independently selected from N or $CR_5$, wherein, $R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein each alkyl, alkenyl, alkynyl, alkoxy, alkylamino, heteroalkyl and cycloalkyl is independently substituted by 0 to 5 $R^a$; $R^a$ is optionally selected from C1-C6 alkyl, halogen, hydroxy, C1-C6 heteroalkyl, C1-C6 alkoxy, C1-C6 alkylamino, cycloalkyl, heterocycloalkyl or cyano.

Preferably, the compound of formula I', or the pharmaceutically acceptable salt, stereoisomer, solvate or prodrug thereof has the structure represented by formula 5' or formula 6',

5'

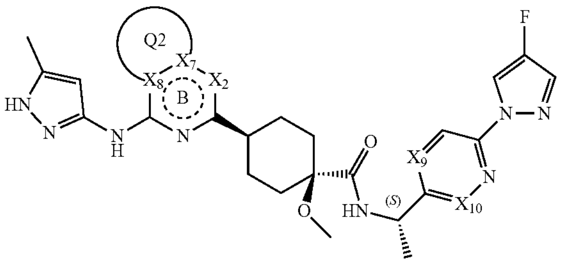

6'

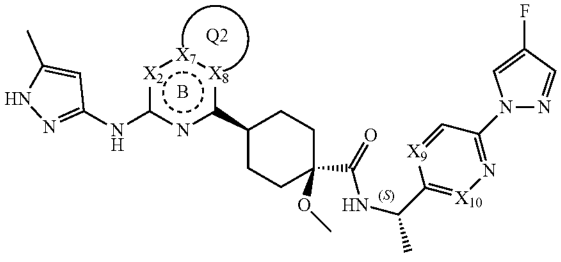

$X_2$, $X_7$, $X_8$, $X_9$, $X_{10}$ and ring Q2 are defined as above, and at least one of $X_7$ and $X_8$ is N.

The salts that may be formed by the compound in the present invention are also within the scope of the present invention. Unless otherwise stated, the compound in the present invention is understood to include its salt. The term "salt" as used herein refers to a salt formed in the form of acid or base from inorganic or organic acid and base. Further, when the compound in the present invention contains a base fragment which includes, but is not limited to pyridine or imidazole, when it contains an acid segment which includes, but is not limited to carboxylic acid. The zwitter-ion that may form "inner salt" is included within the range of the term "salt". Pharmaceutically acceptable (i.e., non-toxic, physiologically acceptable) salt is preferred, although other salts are also useful and may be used, for example, in the separation or purification steps of the preparation process. The compound of the present invention may form a salt, for example, compound I' is reacted with a certain amount (such as an equivalent amount) of an acid or base, and precipitated in a medium, or freeze-dried in aqueous solution.

The base fragment contained in the compounds of the present invention includes but is not limited to amines or pyridine or imidazole rings, and may form salt with organic or inorganic acid. Typical acids that form salts include acetate (such as acetic acid or trihalogenated acetic acid, such as trifluoroacetic acid), adipate, alginate, ascorbate, aspartate, benzoate, benzene sulfonate, disulfate, borate, butyrate, citrate, camphorate, camphor sulfonate, cyclopentane propionate, diethylene glycolate, lauryl sulfate, ethanesulphonate, fumarate, gluceptate, glycerophosphate, hemisulphate, enanthate, caproate, hydrochloride, hydrobromide, hydriodate, isethionate (e.g., 2-hydroxy-ethesulfonate), lactate, maleate, mesylate, naphthalenesulfonate (e.g., 2-naphthalenesulfonate), nicotinate, nitrate, oxalate, pectate, persulfate, phenylpropionate (e.g., 3-phenylpropionate), phosphate, picrate, pivalate, propionate, salicylate, succinate, sulfate (e.g., formed with sulfuric acid), sulfonate, tartrate, thiocyanate, toluenesulfonate (e.g., tosilate), dodecanoate, etc.

Some compounds of the invention may contain acidic fragments including, but not limited to carboxylic acid which may form salts with various organic or inorganic bases. Salt formed by typical base includes ammonium salt, alkali metal salt (such as sodium, lithium and potassium salts), alkaline earth metal salt (such as calcium and magnesium salts), and salt formed by organic bases (such as organic amines), such as benzathine, dicyclohexylamine, hydrabamine (salt formed with N,N-bis (dehydroabietyl) ethylenediamine), N-methyl-D-glucosamine, N-methyl-D-glucoamide, tert-butyllamine, and the salt formed with amino acids such as arginine, lysine, etc. Basic nitrogen-containing groups can form quaternary ammonium salts with halides, such as small molecular alkyl halides (such as chlorides, bromides and iodides of methyl, ethyl, propyl and butyl), dialkyl sulfate (such as dimethyl, diethyl, dibutyl, and dipentyl sulfates), long chain halides (such as chlorides, bromides and iodides of decyl, dodecyl, tetradecyl, and tetradecyl), aralkyl halides (such as bromides of benzyl and phenyl), etc.

The prodrug and solvate of the compound in the present invention are also included within the scope of the present invention. The term "prodrug" herein refers to a compound, which produces a compound, salt, or solvate in the present invention resulting from the chemical transformation of a metabolic or chemical process when used in the treatment of an associated disease. The compounds of the invention include solvates such as hydrates.

Compound, salt or solvate in the present invention, may be present in tautomeric forms such as amide and imine ether. All of these tautomers are part of the present invention.

Stereisomers of all compounds (e.g., those asymmetric carbon atoms that may be present due to various substitutions), including their enantiomeric forms and non-enantiomed forms, all belong to the protection scope of the present invention. The independent stereoisomer in the present invention may not coexist with other isomers (e.g., as a pure or substantially pure optical isomer with special activity), or may be a mixture (e.g., racemate), or a mixture formed with all other stereoisomers or a part thereof. The chiral center of the present invention has two configurations of S or R, which is defined by International Union of Pure and Applied Chemistry (IUPAC) in 1974. The racemization form can be solved by physical methods, such as fractional crystallization, or separation crystallization by derivation into diastereomers, or separation by chiral column chromatography. Individual optical isomer can be obtained from racemate by appropriate methods, including but not limited to conventional methods, such as recrystallization after salting with optically active acids.

Weight content of compound in the present invention obtained by preparation, separation and purification in turn is equal to or greater than 90%, such as equal to or greater than 95%, equal to or greater than 99% ("very pure" compound), which is listed in the description of the text. In addition, the "very pure" compound of the present invention is also part of the present invention.

All configuration isomers of the compound of the present invention are within the scope, whether in mixture, pure or very pure form. The definition of the compound of the present invention comprises cis (Z) and trans (E) olefin isomers, and cis and trans isomers of carbocycle and heterocycle.

In the entire specification, the groups and substituents can be selected to provide stable fragments and compounds.

Specific functional groups and chemical term definitions are described in detail below. For the purposes of the present invention, the chemical elements are consistent with Periodic Table of the Elements, CAS version, *Handbook of Chemistry and Physics,* 75th Ed. The definition of a particular functional group is also described therein. In addition, the basic principles of Organic Chemistry as well as specific functional groups and reactivity are described in "Organic Chemistry", Thomas Sorrell, University Science Books, Sausalito: 1999, the entire content of which is incorporated herein by reference.

Some compounds of the present invention may exist in specific geometric or stereoisomer forms. The present invention covers all compounds, including their cis and trans isomers, R and S enantiomers, diastereomers, (D) type isomers, (L) type isomers, racemic mixtures and other mixtures. In addition, asymmetric carbon atom can represent substituent, such as alkyl. All isomers and mixtures thereof are included in the present invention.

According to the invention, mixtures of isomers may contain a variety ratios of isomers. For example, mixtures with only two isomers may have the following combinations: 50:50, 60:40, 70:30, 80:20, 90:10, 95:5, 96:4, 97:3, 98:2, 99:1, or 100:0, all ratios of the isomers are within the scope of the present invention. Similar ratios readily understood by those of ordinary skill in the art and ratios for mixtures of more complex isomers are also within the scope of the present invention.

The invention also includes isotope labeled compounds, which are equivalent to the original compounds disclosed herein. However, in practice, it usually occurs when one or more atoms are replaced by atoms with a different atomic weight or mass number. Examples of compound isotopes that may be listed in the present invention include hydrogen, carbon, nitrogen, oxygen, phosphorus, sulfur, fluorine and chlorine isotopes, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$. Compound, or enantiomer, diastereomer, isomer, or pharmaceutically acceptable salt or solvate, the above compound containing isotopes or other isotope atoms are all within the scope of the invention. Some isotope-labeled compounds in the present invention, such as the radioactive isotopes of $^{3}H$ and $^{14}C$, are also included and are useful in experiments on the tissue distribution of drugs and substrates. Tritium ($^{3}H$) and Carbon-14 ($^{14}C$), which are relatively easy to prepare and detect, are the preferred choice. In addition, heavier isotope substitutions such as deuterium, i.e. $^{2}H$, have advantages in certain therapies due to their good metabolic stability, such as increased half-life or reduced dosage in vivo, and thus may be preferred in certain situations. Isotope-labeled compounds can be prepared by conventional methods through replacing non-isotopic reagents with readily available isotope-labeled reagents using the disclosed scheme shown in the Example.

If the synthesis of a specific enantiomer of the compound of the invention is to be designed, it can be prepared by asymmetric synthesis, or derivatized with chiral auxiliary reagent, separating the resulting diastereomeric mixture and removing the chiral auxiliary reagent to obtain a pure enantiomer. In addition, if a molecule contains a basic functional group, such as an amino acid, or an acidic functional group, such as a carboxyl group, a diastereomer salt can be formed with a suitable optically active acids or bases, and it can be separated by conventional means, such as crystallization or chromatography, to obtain a pure enantiomer.

As described herein, the compound in the present invention may be substituted with any number of substituents or functional groups to extend its scope. In general, whether the term "substituted" appears before or after the term "optional", the general formula that includes substituents in the compound of the present invention means the substitution of a specified structural substituent for a hydrogen radical. When multiple locations in a particular structure are replaced by multiple specific substituents, each location of the substituents can be the same or different. The term "substituted" as used herein includes all substitution that allows organic compounds to be substituted. Broadly speaking, the allowable substituents include non-cyclic, cyclic, branched, non-branched, carbocyclic and heterocyclic, aromatic ring and non-aromatic organic compounds. In the present invention, such as heteroatomic nitrogen, its valence state may be supplemented by a hydrogen substituent or by any permitted organic compound described above. Furthermore, the invention does not unintentionally limit the substituted organic compounds in any way. The present invention considers that a combination of substituents and variable groups is good for the treatment of diseases in the form of stable compounds. The term "stable" herein refers to a stable compound which is sufficient for maintaining the integrity of the compound structure within a sufficiently long time, preferably being effective in a sufficiently long time, which is hereby used for the above purposes.

The metabolites of the compounds of the present application and their pharmaceutically acceptable salts, and prodrugs that can be converted into the compounds of the present application and their pharmaceutically acceptable salts thereof in vivo, are also included in the claims.

Preparation Method

Methods for preparing compounds of formula I' are described in the following schemes and examples. Raw materials and intermediates are purchased from commercial sources, prepared by known steps, or otherwise described. In some cases, the sequence of steps to perform the reaction scheme may be changed to facilitate the reaction or avoid unwanted side reaction products.

The preparation method of the compound of formula I' of the present invention is more specifically described below, but these specific methods do not constitute any limitation of the invention. The compound of the invention may also optionally be conveniently prepared by combining the various synthetic methods described in this specification or known in the art, such a combination may be easily performed by a skilled person in the art to which the invention belongs.

Generally, in the preparation process, each reaction is usually carried out under the protection of inert gas and in an appropriate solvent at 0 to 90° C., and the reaction time is usually 2-24 hours.

Preferably, the preparation process is as follows:

Method 1:

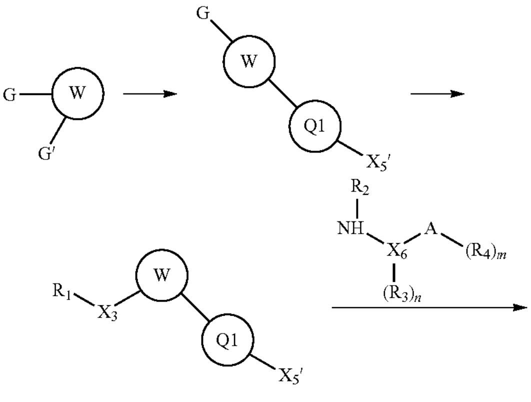

-continued

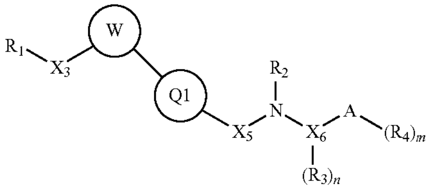

Step 1:

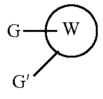

is reacted with

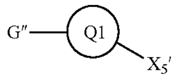

in a solvent (such as DMF/$H_2O$, dioxane, toluene), under basic condition (such as potassium carbonate, sodium carbonate, etc.) and in the presence of catalyst and ligand (such as $Pd(PPh)_3)_4$) to obtain

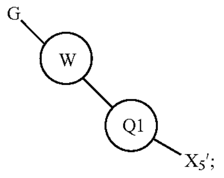

Step 2:

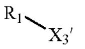

is reacted with

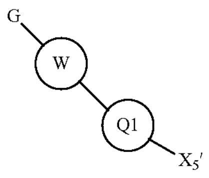

in an inert solvent (such as DMF, dioxane, ethylene glycol dimethyl ether, etc.), under basic condition (such as diisopropylethylamine, potassium acetate, DBU, etc.) or in the presence of catalyst and ligand (such as $Pd(PPh)_3)_4$, $Pd_2(dba)_3$\t-BuXphos, etc.) to obtain

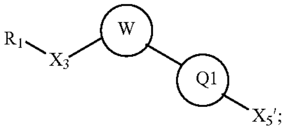

Step 3:

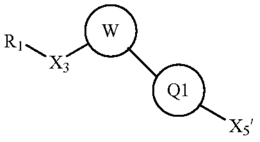

is reacted with

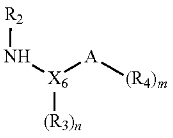

in an inert solvent (such as DMF) and in the presence of condensing agent (such as DMAP, HATU, PyBOP, etc.) to obtain formula I'.

Method 2

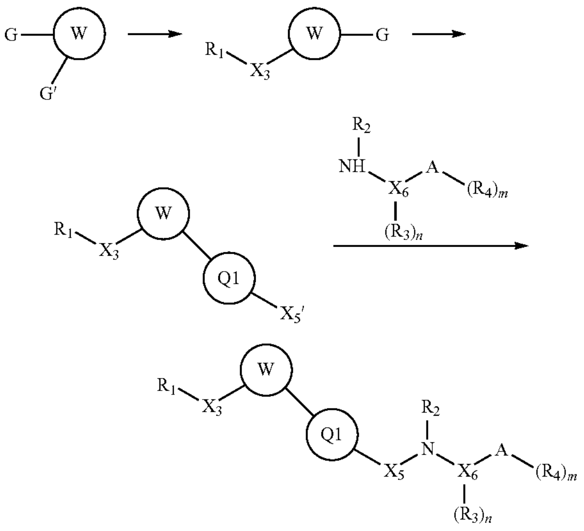

Step 1:

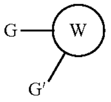

is reacted with

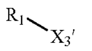

in an inert solvent (such as DMF, dioxane, ethylene glycol dimethyl ether, etc.) under basic condition (such as diisopropylethylamine, potassium acetate, DBU, etc.) or in the presence of catalyst and ligand (such as $Pd(PPh)_3)_4$, $Pd_2(dba)_3$\t-BuXphos etc.) to obtain

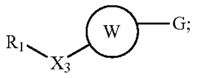

Step 2:

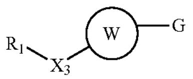

is reacted with

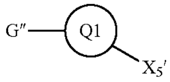

in an inert solvent (such as $DMF/H_2O$), under basic condition (e.g. $K_2CO_3$) and in the presence of catalyst and ligand (such as $Pd(PPh)_3)_4$) to obtain

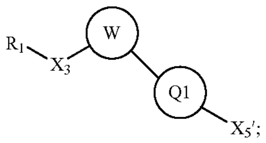

Step 3:

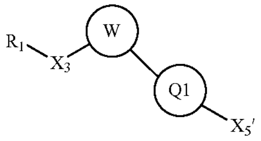

is reacted with

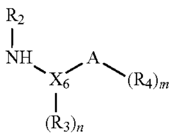

in an inert solvent (such as DMF) and in the presence of condensing agent (such as DMAP, HATU, PyBOP, etc.), to obtain formula I'.

In the above each formula, G and G' are independently halogen (e.g. F, Cl or Br);

G" is borate ester group (e.g.

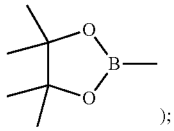

);

$X_3$' is selected from OH, —$NHR_8$, —$CHR_9R_{10}$,

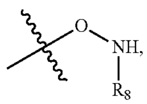

,

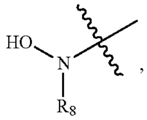

, or

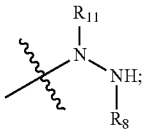

$X_5$' is selected from —C(O)—OH, —S(O)—OH, —$S(O)_2$ —OH,

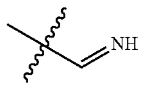

or

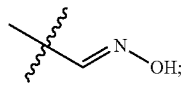

$R_1$, $X_3$, W, Q1, $X_5$, $X_6$, $R_2$, $R_3$, $R_4$, A, Q2, m and n are defined as above.

Unless otherwise specified, the above starting materials can be purchased commercially or synthesized according to the reported literature.

Pharmaceutical Composition and Method of Administration

The pharmaceutical compositions of the present invention are used to prevent and/or treat the following diseases: inflammation, cancer, cardiovascular disease, infection, immunological disease, metabolic disease.

The compounds of formula I' may be used in combination with other drugs known to treat or improve similar conditions. When administered in combination, the original administration method and dosage for the drug can remain unchanged, while compound of formula I' may be administered simultaneously or subsequently. Pharmaceutical composition containing one or more known drugs and the compound of formula I' may be preferred when the compound of formula I' is administered simultaneously in combination with one or more other drugs. The drug combination also includes administering the compound of formula I' and other one or more known drugs at overlapping time. When the compound of formula I' is combined with other one or more drugs, the dosage of the compound of formula I' or known drug may be lower than that of their individual use.

The drug or active ingredients that can be used in pharmaceutical use with the compounds of the formula I' include but are not limited to PD-1 inhibitor (such as nivolumab, pembrolizumab, JS-001, SHR-120, BGB-A317, IBI-308, GLS-010, GB-226, STW204, HX008, HLX10, BAT 1306, AK105, LZM 009 or the biological analogue thereof, etc.), PD-L1 inhibitor (such as durvalunab, atezolizumab, CS1001, KN035, HLX20, SHR-1316, BGB-A333, JS003, CS1003, KL-A167, F 520, GR1405, MSB2311 or the biological analogue thereof, etc.), CD20 antibody (such as rituximab, obinutuzumab, ofatumumab, tositumomab, ibritumomab, etc.), CD47 antibody (such as Hu5F9-G4, CC-90002, TTI-621, TTI-622, OSE-172, SRF-231, AlX- 148, NI-1701, SHR-1603, IBI188, IMM01), ALK inhibitor (such as Ceritinib, Alectinib, Brigatinib, Lorlatinib, Ocatinib), PI3K inhibitor (such as Idelalisib, Dactolisib, Taselisib, Buparlisib, etc.), BTK inhibitor (such as Ibrutinib, Tirabrutinib, Acalabrutinib, etc.), EGFR inhibitor (such as Afatinib, Gefitinib, Erlotinib, Lapatinib, Dacomitinib, Icotinib, Canertinib, etc.), VEGFR inhibitor (such as Sorafenib, Pazopanib, Regorafenib, Cabozantinib, Sunitinib, Donafenib, etc.), HDAC inhibitor (such as Givinostat, Droxinostat, Entinostat, Dacinostat, Tacedinaline, etc.), CDK inhibitor (such as Palbociclib, Ribociclib, Abemaciclib, Lerociclib, etc.), MEK inhibitor (such as Selumetinib (AZD6244), Trametinib (GSK1120212), PD0325901, U0126, AS-703026, PD184352 (CI-1040), etc.), mTOR inhibitor (such as Vistusertib, etc.), SHP2 inhibitor (such as RMC-4630, JAB-3068, TNO 155, etc.), IGF-1R inhibitor (such as Ceritinib, Okatinib, linsitinib, BMS-754807, GSK1838705A, etc.) or combinations thereof.

The dosage forms of the pharmaceutical composition of the present invention include (but are not limited to) injection, tablet, capsule, aerosol, suppository, pellicle, pill, liniment for external use, controlled release or sustained-release or nano formulation.

The pharmaceutical composition of the present invention comprises a compound of the present invention or a pharmaceutically acceptable salt and a pharmaceutically acceptable excipient or carrier with safe and effective amount, wherein "safe and effective amount" refers to the amount of compound is sufficient to significantly improve the condition, not to produce severe side effects. Typically, the pharmaceutical composition contains 1-2000 mg of the compound of the present invention/dosage, and preferrably contains 10-1000 mg of the compound of the present invention/dosage. Preferably, "one dosage" is a capsule or a pill.

"Pharmaceutically acceptable carrier" refers to one or more compatible solid or liquid filler or gel substances, which are suitable for human use, and must be sufficiently pure and of sufficiently low toxicity. "Compatible" herein refers to ability of each component of a composition can be mixed with the compound of the present invention and can be mixed with each other without appreciably reducing the efficacy of the compound. Examples of pharmaceutically acceptable carrier include cellulose and derivatives thereof (such as sodium carboxymethylcellulose, sodium ethylcellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerol, mannitol, sorbitol, etc.), emulsifier (such as Tween®), wetting agent (such as lauryl sodium sulfate), colorant, flavoring, stabilizer, antioxidant, preservative, pyrogen-free water, etc.

There is no special limitation of administration mode for the compound or pharmaceutical compositions of the present invention, and the representative administration mode includes (but is not limited to): oral, intratumorally, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, such as starch, lactose, sucrose, glucose, mannitol and silicic acid; (b) binders, such as hydroxymethyl cellulose, alginate, gelatin, polyvinylpyrrolidone, sucrose and arabic gum; (c) humectant, such as, glycerol; (d) disintegrating agent, such as agar, calcium carbonate, potato starch or tapioca starch, alginic acid, certain composite silicates, and sodium carbonate; (e) dissolution-retarding agents, such as paraffin; (f) absorption accelerators, such as quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, lauryl sodium sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, such as ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

The treatment method of the present invention can be administered alone or in combination with other treatment means or therapeutic drugs. When the pharmaceutical compositions are used, a safe and effective amount of compound of the present invention is administrated to a mammal (such as human) in need thereof, wherein the dose of administration is a pharmaceutically effective dose. For a person weighed 60 kg, the daily dose is usually 1-2000 mg, preferably 50-1000 mg. Of course, the particular dose should also depend on various factors, such as the route of administration, patient healthy status, which are well within the skills of an experienced physician.

The present invention also provides a preparation method of pharmaceutical composition comprising the step of mixing a pharmaceutically acceptable carrier with the compound of formula I' or crystal form, pharmacically acceptable salt, hydrate or solvate thereof of the present invention, thus forming the pharmaceutical composition.

The invention also provides a treatment method comprising the step of administering the compound of formula I', or its crystalline form, pharmaceutically acceptable salt, hydrate or solvate thereof, or the pharmaceutical composition of the invention to a subject in need thereof to inhibit RET.

The invention has the following main advantages:

(1) The compound of the invention has excellent inhibition ability to RET kinase;

(2) The compound of the invention has lower toxic and side effects.

(3) The compound of the invention has better pharmacodynamic and pharmacokinetic properties.

EXAMPLE

The technical solution of the present invention will be further described below, but the protection scope of the present invention is not limited thereto.

Example 1

The compound synthesized in the present invention:

C1

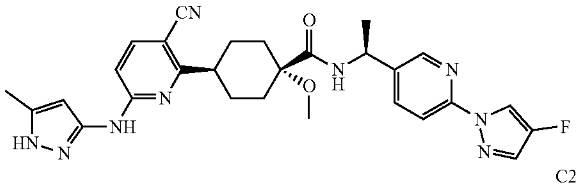

C2

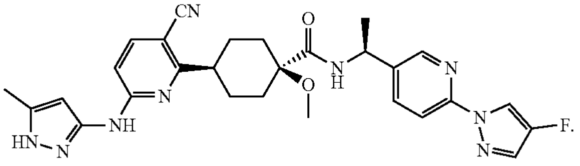

The experimental process was as follows:

1. Synthesis of Intermediate C1-7

The synthetic route was as follows:

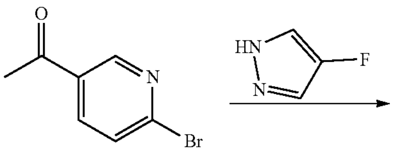

C1-8

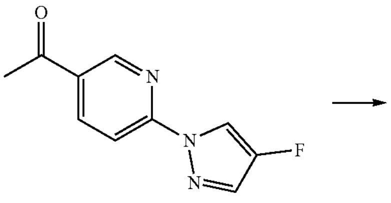

C1-9

-continued

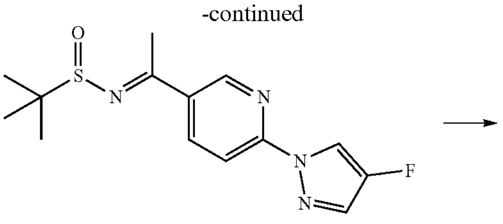

C1-10

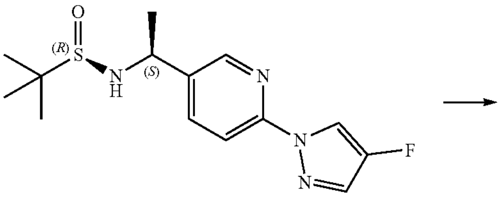

C1-11

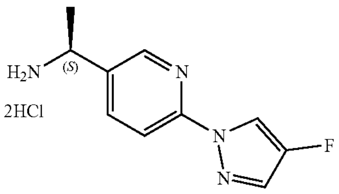

C1-7

1. Synthesis of C1-9

C1-8 (6.98 g, 34.9 mmol), 4-fluoro-1H-pyrazole (3.3 g, 35 mmol), potassium carbonate (11.1 g, 73.6 mmol) and DMF (30 mL) were added into a 100 mL single-neck flask to react at 100° C. for 15 h. Then it was cooled to room temperature, poured into water, filtered and dried to obtain 5.93 g of compound C1-9. Nuclear magnetic analysis data of compound C1-9: $^1$H NMR (400 MHz, $CDCl_3$): δ 8.96-8.95 (d, J=1.8 Hz, 1H), 8.47-8.45 (dd, 1H), 8.37-8.34 (dd, 1H), 8.05-8.03 (dd, 1H), 7.66-7.65 (d, J=3.96, 1H), 2.65 (s, 3H).

2. Synthesis of C1-10

C1-9 (4.2 g, 0.02 mol), R-tert-butyl sulfinamide (2.48 g, 0.02 mol), tetraethyl titanate (9.34 g, 0.041 mol) and THF (50 mL) were added into a 100 mL three-neck flask to react at 75° C. for 15 h. Then it was cooled to room temperature, poured into water, filtered. The filter cake was washed with ethyl acetate, and the organic phases were combined, dried, concentrated, and purified by column chromatography to obtain 5.35 g of compound C1-10.

Nuclear magnetic analysis data of compound C1-10: $^1$H NMR (400 MHz, $CDCl_3$): δ 8.96-8.95 (d, J=1.8 Hz, 1H), 8.47-8.45 (dd, 1H), 8.37-8.34 (dd, 1H), 8.05-8.03 (dd, 1H), 7.66-7.65 (d, J=3.96, 1H), 2.65 (s, 3H).

3. Synthesis of C1-11

C1-10 (3.5 g) and THF (50 mL) were added into a 100 mL three-neck flask, cooled to −70° 1, lithium tri-sec-butylborohydride in THF (1M, 34.1 mL) was added dropwise, and stirred at this temperature for half an hour, then naturally raised to room temperature. TLC showed the reaction was completed. 5 mL methanol was added to quench the reaction, then water was added, filtered, and the filter cake was washed with ethyl acetate. Organic phases were combined, dried, concentrated, and purified by column chromatography to obtain 3.1 g of compound C1-11. Nuclear magnetic analysis data of compound C1-11: $^1$H NMR (400 MHz, $CDCl_3$): δ 8.40-8.39 (d, J=4.6 Hz, 1H), 8.36-8.35 (d, J=2.08 Hz, 1H), 7.94-7.91 (d, J=8.48 Hz, 1H), 7.79-7.76 (m, 1H), 7.59-7.58 (d, J=4.28, 1H), 4.68-4.63 (m, 1H), 3.37-3.36 (m, 1H), 1.59-1.57 (d, J=6.72, 3H), 1.21 (s, 9H).

4. Synthesis of C1-7

C1-11 (3.1 g) was added into a 100 mL three-neck flask, then methanol (10 mL) and 1,4-dioxane (10 mL) were added to dissolve under stirring. Then HCl/1,4-dioxane (4M, 25 mL) was added, stirred at room temperature for 2 h. The reaction solution was concentrated to obtain a crude product, and the crude product was slurried in ether to obtain 2.27 g of compound C1-7.

Nuclear magnetic analysis data of compound C1-7: $^1H$ NMR (400 MHz, DMSO-$D_6$): δ 8.79 (br, 3H), 8.74-8.72 (m, 1H), 8.64-8.63 (d, J=2.08 Hz, 1H), 8.23-8.20 (m, 1H), 7.97-7.95 (m, 2H), 4.52-4.52 (m, 1H), 1.60-1.58 (d, J=6.84 Hz, 3H).

II. Synthesis of Intermediate C1-3

The synthetic route was as follows:

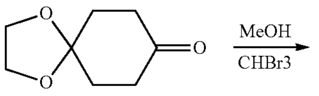

C1-12

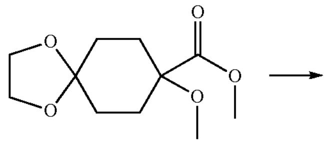

C1-13

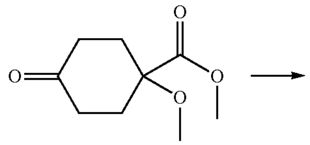

C1-14

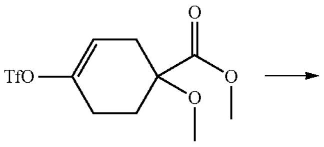

C1-15

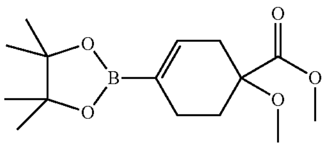

C1-3

1. Synthesis of Compound C1-13

Bromoform (125 mL) and C1-12 (128 mmol, 20 g) were added into a 250 mL three-neck flask, and stirred to dissolve, then cooled to 0° C., and KOH (1 mol, 57.4 g) in methanol (300 mL) was added dropwise slowly. After addition, the temperature was raised to room temperature and stirred for 16 h. TLC showed the reaction was completed. The reaction solution was concentrated, diluted with water (50 mL), extracted with ethyl acetate three times. Organic phase was washed with saturated brine, dried, and concentrated under reduced pressure to obtain 25 g of C1-13, which was directly used in the next step.

2. Synthesis of Compound C1-14

C1-13 (86 mmol, 20 g) and methanol (200 mL) were added into a 500 mL single-neck flask, then concentrated hydrochloric acid (100 mL) was added under stirring at room temperature, and stirred at room temperature for 16 h. TLC showed that the reaction was completed. The reaction solution was concentrated, and saturated $NaHCO_3$ aqueous solution was added for adjusting pH to 6-7, extracted with ethyl acetate for three times. Organic phase was washed with saturated brine, dried, concentrated under reduced pressure to obtain crude product, and purified by column chromatography (developing agent: ethyl acetate/petroleum ether=1:30-1:5) to obtain 10 g of C1-14.

3. Synthesis of Compound C1-15

50 mL anhydrous toluene and anhydrous pyridine (4.5 mL, 53 mmol) were added into a 250 mL three-neck flask and cooled to −10° C. Trifluoromethylsulfonic anhydride (10.8 mL, 60 mmol) in anhydrous toluene (60 mL) was slowly added dropwise under the protection of nitrogen. After addition, the temperature was raised to room temperature slowly, and C1-14 (9 g, 48 mmol) in anhydrous toluene (30 mL) was added. The reaction solution was raised to 40° C. and stirred for 16 h. TLC showed that the reaction was completed, diluted with 10 mL water, extracted with ethyl acetate for three times. Organic phase was washed with saturated brine, dried, concentrated under reduced pressure to obtain crude product, and it was purified by column chromatography (developing agent: ethyl acetate/petroleum ether=1:40-1:20) to obtain 9 g of C1-15.

4. Synthesis of Compound C1-3

C1-15 (9 g, 28 mmol), bis(pinacolato)diboron (8.7 g, 34 mmol), dppf (1.5 g, 3 mmol), palladium acetate (350 mg, 1.5 mmol), potassium acetate (8.25 g, 88 mmol) and dioxane (120 mL) were added sequentially into a 250 mL three-neck flask under the protection of nitrogen, replaced with nitrogen for three times, then the reaction solution was stirred at 95° C. for 16 hours. TLC showed the reaction was completed, filtered and concentrated under reduced pressure, then diluted with 20 mL water, extracted with ethyl acetate for three times. Organic phase was washed with saturated brine, dried, concentrated under reduced pressure to obtain crude product, and it was purified by column chromatography (developing agent: ethyl acetate/petroleum ether=1:20-1:10) to obtain product C1-3 (yellowish solid, 8 g).

3. Synthesis of Compounds C1 and C2

The synthetic route was as follows:

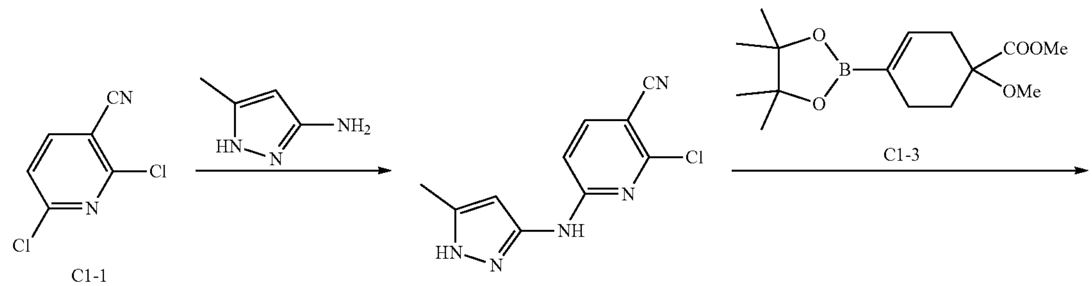

C1-3

C1-1

C1-2

-continued

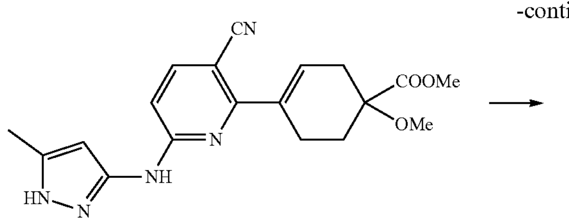

C1-4

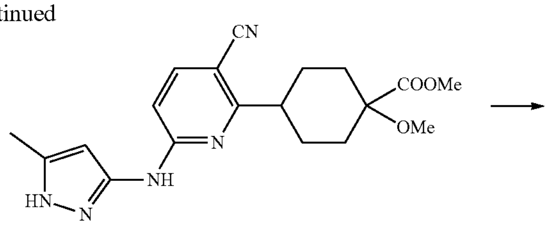

C1-5

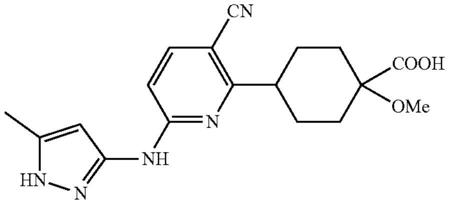

C1-6

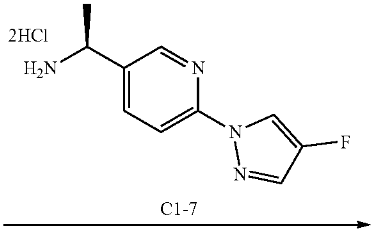

C1-7

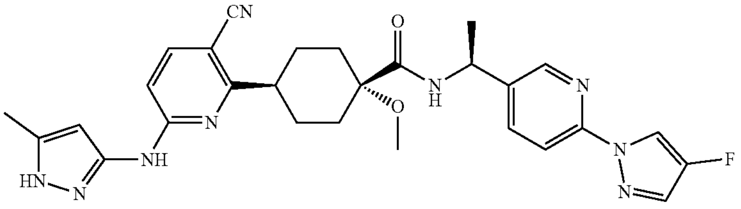

C1 and

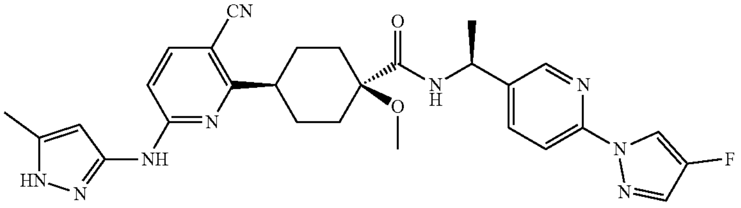

C2

1. Synthesis of C1-2

C1-1 (3.46 g, 20 mmol), 3-amino-5-methylpyrazole (2.14 g, 22 mmol), DMF (50 mL) and diisopropylethylamine (3.88 g, 30 mmol) were added into a 250 mL single-neck flask to react at 90° C. overnight. LC-MS showed that the reaction was completed, the reaction solution was poured into 200 mL water under stirring, and solid was precipitated, then filtered. The filter cake was washed with water, dried, slurried with methanol (100 mL), filtered, and repeated the operation for 3-5 times to obtain 2.82 g. [M+H]: 234.1.

2. Synthesis of C1-4

C1-2 (2.1 g, 9 mmol), C1-3 (2.66 g, 9 mmol), $Pd(PPh_3)_4$ (1.04 g, 0.9 mmol), $K_2CO_3$ (1.86 g, 13.5 mmol) and DMF/$H_2O$ (30 mL/12 mL) were added into a 250 mL single-neck flask to react at 110° C. overnight under the protection of $N_2$. LC-MS showed that the reaction was completed. The reaction solution was poured into water (300 mL) under stirring, extracted with ethyl acetate for three times, washed with saturated brine, dried over anhydrous sodium sulfate, evaporated, and purified by column chromatography using DCM:MeOH=50:1-10:1 to obtain 1.87 g. [M+H]: 368.2.

3. Synthesis of C1-5

C1-4 (720 mg, 1.96 mmol), $Pd(OH)_2/C$ (10%, 300 mg) and EtOH (100 mL) were added into a 250 mL single-neck flask to react at 80° C. overnight under $H_2$ atmosphere. LC-MS showed that the reaction was completed, filtered, evaporated, and purified by column chromatography with DCM:MeOH=100: 1-50:1 to obtain 502 mg of white solid. [M+H]: 370.3.

4. Synthesis of C1-6

C1-5 (240 mg, 0.65 mmol), LiOH·$H_2O$ (55 mg, 1.3 mmol) and MeOH/$H_2O$ (5 mL/1 mL) were added into a 25 mL single-neck flask to react at 50° C. overnight. LC-MS showed that the reaction was completed, and 241 mg of crude product was obtained by concentration. [M+H]: 356.2.

5. Synthesis of C1 and C2

C1-6 (249 mg, 0.69 mmol), C1-7 (212 mg, 0.76 mmol), and DMF (2 mL) were added into a 25 mL single-neck flask, then DMAP (337 mg, 2.76 mmol) and HATU (393 mg, 1.04 mmol) were added to react at 25° C. for 1 h. LC-MS showed that the reaction was completed. The reaction solution was poured into water (20 mL), extracted with ethyl acetate for three times, washed with saturated brine, dried over anhydrous sodium sulfate, evaporated, and purified by column chromatography using DCM:MeOH=100: 1-30:1 to obtain crude products C2 (12 mg, purity: 96.7%). [M+H]: 544.3; C1 (11 mg; purity: 97.6%), [M+H]: 544.3.

C1 and C2 were separated by waters high performance liquid chromatography under the following conditions:

Instrument: waters

Column: innovalODS-2/C18 (30×100 mm, 5 μm)

Mobile phase: Phase A: water (containing 0.1% trifluoroacetic acid)

Phase B: methanol

Flow rate: 15.0 ml/min, detection wavelength: 254 nm

Solvent: methanol-water (1:1)

Injection concentration: about 15 mg/ml

Injection volume: 2 ml

Peak time: 14.7 min

Gradient Program:

| t/min | Phase B | Phase A |
|---|---|---|
| 0 | 40 | 60 |
| 5 | 70 | 30 |
| 15 | 70 | 30 |
| 18 | 90 | 10 |
| 20 | 90 | 10 |
| 21 | 40 | 60 |
| 25 | 40 | 60 |

Example 2

The compound synthesized in the present invention:

C3

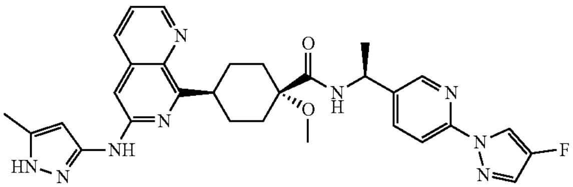

C4

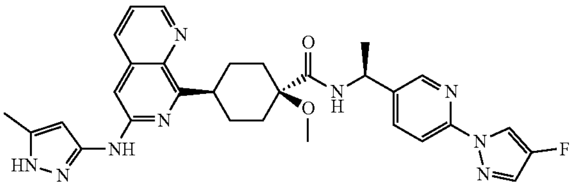

The synthetic route and experimental process were as follows:

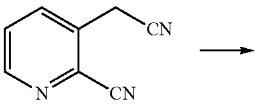

C3-1

-continued

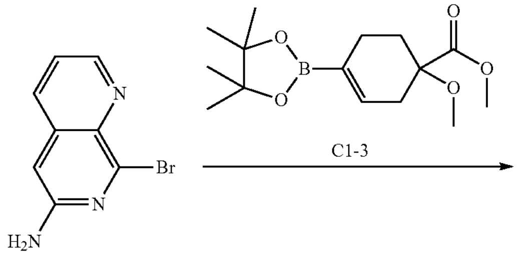

C1-3

C3-2

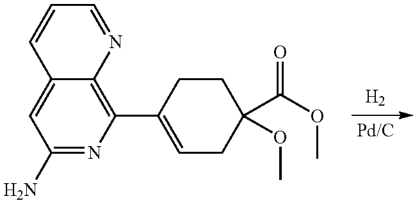

C3-4

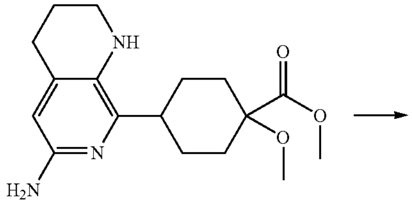

C3-5

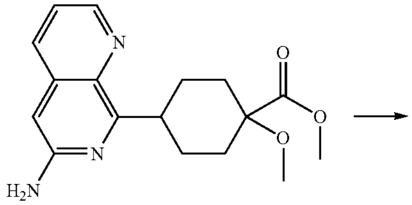

C3-6

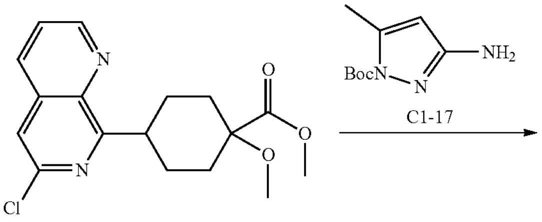

C1-17

C3-16

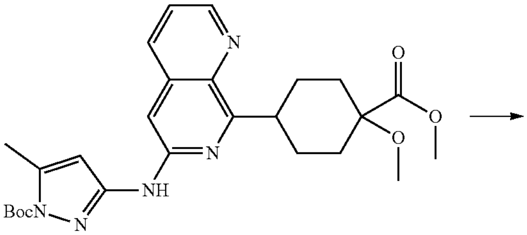

C3-18

-continued

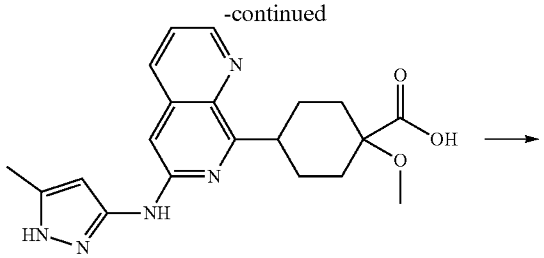

C3-19

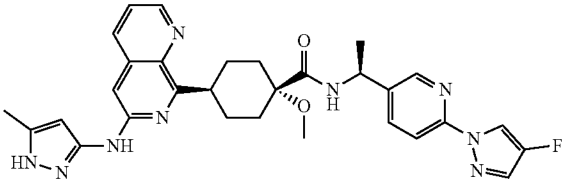

C3

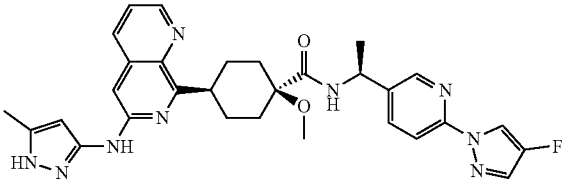

C4

1. Synthesis of C3-2

31 mL hydrobromic acid in acetic acid was added into a 100 mL single-neck flask, and 5 g of compound C3-1 was added into the solution in batches under stirring at a temperature not exceeding 30° C. After addition, it was reacted at room temperature for 2 h. Then it was cooled to 0° C., 30 mL ethyl acetate was added, then filtered, and the filter cake was washed with ethyl acetate. The filter cake was added into methanol (50 mL), stirred, filtered, and filter cake was washed with methanol (20 mL). The filter cake was added into water and stirred, sodium carbonate was added to adjust pH to 9, filtered. The filter cake was washed with water and dried to obtain 4.7 g of compound C3-2.

Nuclear magnetic analysis data of compound C3-2: $^1H$ NMR (400 MHz, DMSO): δ 8.61-8.60 (dd, 1H), 8.04-8.02 (dd, 1H), 7.51-7.48 (dd, 1H), 6.61 (s, 1H), 6.49 (br, 2H).

2. Synthesis of C3-4

C3-2 (3 g, 0.013 mol), C1-3 (4.56 g, 0.0154 mol), tricyclohexyl phosphine (0.36 g, 0.0013 mol), potassium carbonate (2.7 g, 0.0195 mol), palladium acetate (146 mg, 0.65 mmol), dioxane (60 mL) and water (7 mL) were added into a 250 mL three-neck flask and stirred at 100° C. for 15 h. Then it was cooled, filtered, concentrated, and water was added to the residue, extracted with dichloromethane, dried, and concentrated. The residue was added with ether, stirred, filtered, and the filter cake was dried to obtain 3 g of compound C3-4.

Nuclear magnetic analysis data of compound C3-4: $^1H$ NMR (400 MHz, DMSO): δ 8.52-8.51 (dd, 1H), 7.95-7.92 (dd, 1H), 7.39-7.36 (dd, 1H), 6.54-6.53 (m, 1H), 6.49 (s, H), 6.03 (br, 2H), 3.73 (s, 3H), 3.21 (s, 3H), 2.75-2.67 (m, 3H), 2.5-2.45 (m, 1H), 2.18-2.12 (m, 1H), 2.04-2.00 (m, 1H).

3. Synthesis of C3-5

6 g compound C3-4 was added into a 500 mL single-neck flask, then palladium hydroxide on carbon (2 g) and ethyl acetate (200 mL) were added to react at 60° C. for 3 days under hydrogen atmosphere, then it was filtered. The filtrate was concentrated to obtain a crude product, and purified by column chromatography to obtain 2.5 g of compound C3-5, which was directly used for the next reaction.

4. Synthesis of C3-6

Compound C3-5 (2.5 g) was added to a single-neck flask, then 5% palladium on carbon (2 g) and toluene (90 mL) were added, heated and reacted under reflux in air for 4 days, then it was filtered. The filtrate was concentrated and purified by column chromatography to obtain 2.3 g of compound C3-6.

Nuclear magnetic analysis data of compound C3-6: $^1H$ NMR (400 MHz, $CDCl_3$): δ 8.65-8.63 (dd, 1H), 7.82-7.79 (dd, 1H), 7.35-7.32 (dd, 1H), 6.50-6.49 (dd, 1H), 4.57-4.50 (m, 2H), 4.20-4.10 (m, 1H), 3.83-3.78 (m, 3H), 3.34-3.30 (m, 3H), 2.75-2.67 (m, 3H), 2.56-2.52 (m, 1H), 2.20-2.17 (m, 1H), 2.13-1.97 (m, 3H), 1.93-1.70 (m, 3H).

5. Synthesis of C3-16

1.24 g of compound C3-6 was dissolved in concentrated hydrochloric acid (30 mL), and kept the temperature at −5° C.-5° C. Sodium nitrite (1.36 g) was dissolved in water (8 mL) and then added dropwise to the above reaction, kept the temperature and stirred for 1 h. A mixture of cuprous chloride (1.96 g) and hydrochloric acid (8 mL) was added dropwise to the reaction, kept the temperature and stirred for 1 h, then stirred at room temperature for 1 h. The reaction solution was slowly added into ammonia water, kept alkaline, extracted with dichloromethane, and concentrated to obtain crude product. The crude product was added into toluene (80 mL) and phosphorus oxychloride (4.25 mL), raised to 100° C. and stirred for 3 hours. Then it was concentrated. The residue was added into an aqueous solution of sodium bicarbonate, extracted with dichloromethane, dried, concentrated and purified by column chromatography to obtain 0.55 g of compound C3-16.

Nuclear magnetic analysis data of compound C3-16: $^1H$ NMR (400 MHz, CDCl3): δ 8.98-8.96 (dd, 1H), 8.06-8.03 (dd, 1H), 7.59-7.53 (m, 2H), 4.24-4.14 (m, 1H), 3.84-3.79 (m, 3H), 3.33-3.30 (m, 3H), 2.58-2.55 (m, 1H), 2.24-1.85 (m, 6H), 1.78-1.70 (m, 1H).

6. Synthesis of C3-18

Compound C3-16 (487 mg), compound C1-17 (430 mg), tris(dibenzylideneacetone)dipalladium(133 mg), 2-di-tert-butyl phosphono-2',4',6'-triisopropylbiphenyl (123 mg), DBU (443 mg) and ethylene glycol dimethyl ether (7.5 mL) were added into a 50 mL single-neck flask to react at 60° C. for 15 hours under the protection of argon. The reaction solution was concentrated and purified by column chromatography to obtain 626 mg of compound C3-18.

Nuclear magnetic analysis data of compound C3-18: 1H NMR (400 MHz, CDCl3): δ 8.73-8.72 (dd, 1H), 8.00-7.96 (m, 1H), 7.71-7.65 (d, 1H), 7.43-7.40 (m, 1H), 7.12-7.08 (d, 1H), 6.19-6.18 (d, 1H), 4.25-4.17 (m, 1H), 3.84-3.79 (d, 3H), 3.35-3.30 (d, 3H), 2.57-2.53 (m, 4H), 2.22-2.18 (m, 1H), 2.11-1.99 (m, 3H), 1.93-1.83 (m, 2H), 1.79-1.72 (m, 1H), 1.68 (s, 9H).

7. Synthesis of C3-19

The compound C3-18 (576 mg), $LiOH{\cdot}H_2O$ (153 mg) in tetrahydrofuran/methanol/water (17:1:1, 21 mL) were added into a 50 mL single-neck flask, and stirred at 60° C. for 15 hours. LC-MS showed that the raw material was not completely reacted, and $LiOH{\cdot}H_2O$ (50 mg) was added and continued stirring for 15 hours. Then methyl tert-butyl ether and water were added, water phase was evaporated to obtain crude C3-19 which was directly used for the next reaction.

8. Synthesis of C3 and C4

Compound C3-19 (387 mg), compound C1-7 (279 mg), diisopropylethylamine (1 g) and DMF (6 mL) were added into a 50 mL single-neck flask, then HATU (570 mg) was added under stirring, stirred at room temperature for 1 hour, adding water, extracted with dichloromethane for three times. Organic phase was washed with water, dried, concentrated and purified by column chromatography to obtain crude product, and separated to obtain compounds C3 and C4.

C3 and C4 were separated by waters high performance liquid chromatography under the following conditions:

Instrument: waters

Column: innovalODS-2/C18 (30×100 mm, 5 μm)

Mobile phase: Phase A: water (containing 0.1% trifluoroacetic acid)

Phase B: methanol

Flow rate: 15.0 ml/min, detection wavelength: 254 nm

Solvent: methanol-water (1:1)

Injection concentration: about 15 mg/ml

Injection volume: 2 ml

Peak time: 15.8 min/17.8 min

Gradient Program:

| t/min | Phase B | Phase A |
|---|---|---|
| 0 | 62 | 38 |
| 17 | 62 | 38 |
| 19 | 90 | 10 |
| 22 | 90 | 10 |
| 23 | 62 | 38 |
| 27 | 62 | 38 |

Nuclear magnetic analysis data of compound C4: 1H NMR (400 MHz, CDCl3): δ 8.70-8.68 (dd, 1H), 8.39-8.38 (m, 2H), 7.93-7.90 (d, 2H), 7.90-7.76 (dd, 1H), 7.59-7.58 (d, 1H), 7.40-7.37 (dd, 1H), 7.32 (s, 1H), 6.86-6.84 (d, 1H), 6.01 (s, 1H), 5.24-5.16 (m, 1H), 4.25-4.20 (m, 1H), 3.31 (s, 3H), 2.34 (s, 3H), 2.22-1.96 (m, 6H), 1.91-1.86 (m, 2H), 1.59-1.57 (d, 3H).

Example 3

The compound synthesized in the present invention:

C5

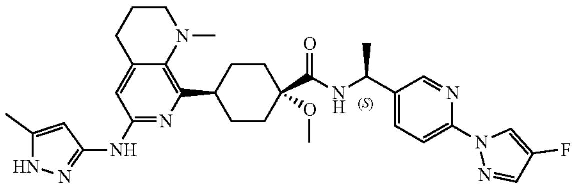

C6

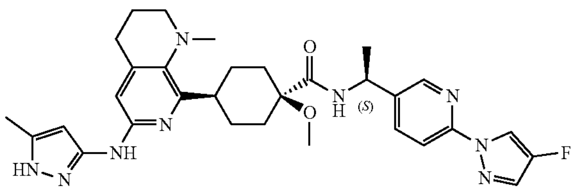

The synthetic route and experimental process were as follows:

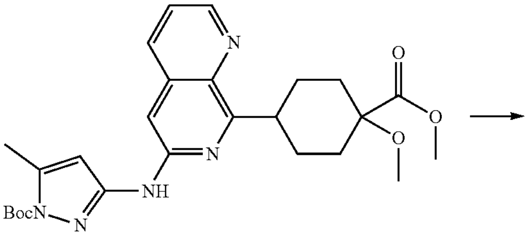

C3-18

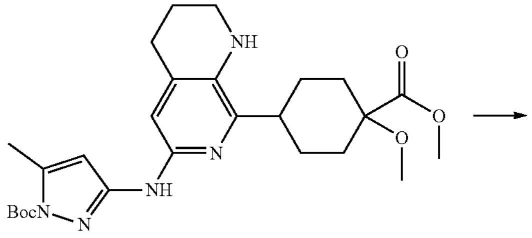

C5-1

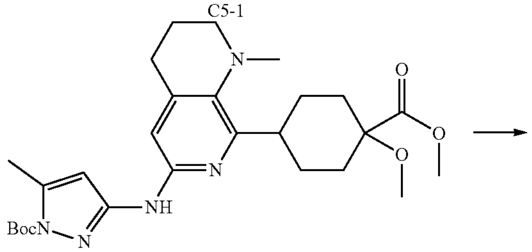

C5-2

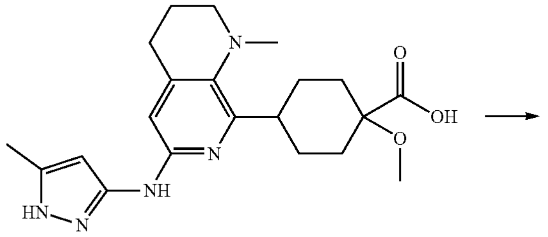

C5-3

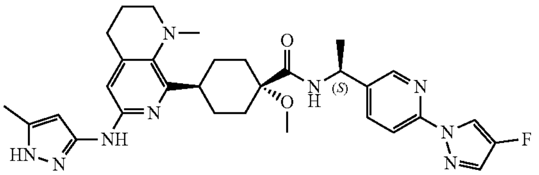

C5 and

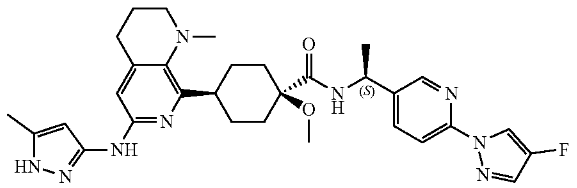

C6

1. Synthesis of C5-1

Compound C3-18 (0.91 g), palladium hydroxide on carbon (600 mg), ethyl acetate (20 mL) and methanol (20 mL) were added into a 250 mL single-neck flask, and stirred at room temperature for 48 h under $H_2$ atmosphere. TLC showed that the reaction was completed. It was filtered and concentrated to obtain crude product which was directly used for the next step.

2. Synthesis of C5-2

Compound C5-1 (0.87 g), formaldehyde solution (37%, 565 mg), acetic acid (418 mg) and tetrahydrofuran (16 mL) were added into a 50 mL single-neck flask. After stirring for 10 minutes, sodium triacetoxyborohydride (1.84 g) was added and stirred overnight at room temperature. TLC showed that the reaction was completed. Adding water, extracted with ethyl acetate, dried and concentrated, and purified by column chromatography to obtain 0.84 g of C5-2.

Nuclear magnetic analysis data of compound C5-2: 1H NMR (400 MHz, CDCl3): δ 6.90-6.89 (d, 1H), 6.67-6.64 (d, 1H), 6.57-6.49 (d, 1H), 3.83-3.78 (d, 3H), 3.56-3.28 (d, 3H), 3.17-3.05 (m, 4H), 2.76-2.72 (m, 2H), 2.65-2.64 (d, 3H), 2.59-2.52 (d, 3H), 2.50-2.48 (m, 1H), 2.16-2.07 (m, 2H), 1.91-1.75 (m, 6H), 1.61-1.59 (m, 2H).

3. Synthesis of C5-3

Compound C5-2 (0.8 g), lithium hydroxide monohydrate (261 mg) and THF/MeOH/$H_2O$ (15:1:1, 26 mL) were added into a 50 mL single-neck flask to react at 60° C. for 14 h.

Concentrated, water was removed by toluene to obtain crude product C5-3, which was directly used for the next step.

4. Synthesis of C5 and C6

Crude product compound C5-3 (399 mg), compound C1-7 (279 mg), diisopropylethylamine (1 g) and DMF (6 mL) were added into a 50 mL single-neck flask, then HATU (570 mg) was added under stirring, stirred at room temperature overnight, adding water, extracted with ethyl acetate for three times. Organic phase was washed with water, dried, concentrated and purified by column chromatography to obtain crude product, then separated to obtain compounds C5 and C6.

Nuclear magnetic analysis data of compound C6: 1H NMR (400 MHz, CDCl3): δ 8.38-8.37 (m, 2H), 7.91-7.90 (d, 1H), 7.78-7.75 (dd, 1H), 7.58-7.57 (d, 1H), 6.89-6.87 (d, 1H), 6.32 (br, 1H), 5.20-5.13 (m, 1H), 3.34 (s, 3H), 3.20-3.18 (m, 1H), 3.05-3.03 (m, 2H), 2.75-2.71 (m, 2H), 2.64 (s, 3H), 2.30 (s, 3H), 2.05-1.81 (m, 8H), 1.62-1.56 (m, 8H).

Example 4

The compound synthesized in the present invention:

C7

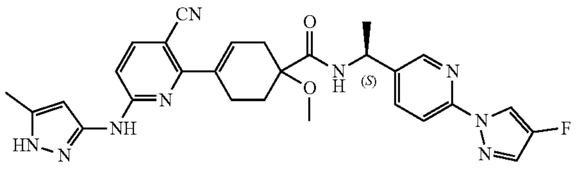

The synthetic route and experimental process were as follows:

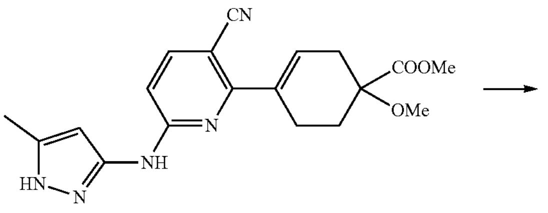

C1-4

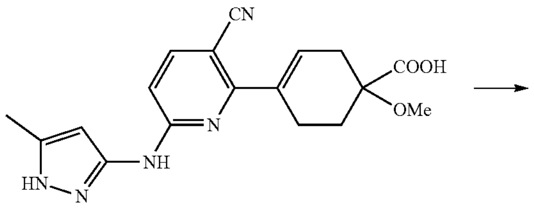

C7-1

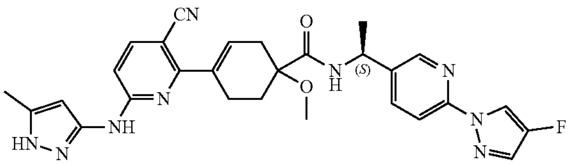

C7

1. Synthesis of C7-1

C1-4 (186 mg, 0.51 mmol), LiOH·$H_2O$ (43 mg, 1 mmol) and MeOH/$H_2O$ (5 mL/1 mL) were added into a 50 mL single-neck flask to react at 50° C. overnight. LC-MS showed that the reaction was completed, and 100 mg of crude product was obtained by concentration.

2. Synthesis of C7

C7-1 (83 mg, 0.24 mmol), DMF (2 mL) and HATU (134 mg, 0.35 mmol) were added into a 50 mL single-neck flask, then diisopropylethylamine (243 mg, 1.88 mmol) and C1-7 (72 mg, 0.26 mmol) were added under stirring at room temperature to react at 50° C. LC-MS showed that the reaction was completed. The reaction solution was poured into 20 mL water, extracted with ethyl acetate for three times, washed with saturated brine, dried over anhydrous sodium sulfate, evaporated, and separated to obtain C7 (17 mg, purity: 89.9%), [M+H]: 542.3.

Nuclear magnetic analysis data of compound C7: 1H NMR (400 MHz, DMSO) δ 11.99 (s, 1H), 9.91 (s, 1H), 8.66 (dd, J=22.0, 5.9 Hz, 2H), 8.45 (s, 1H), 8.01 (t, J=5.9 Hz, 1H), 7.88 (ddd, J=18.7, 12.7, 6.6 Hz, 3H), 7.18 (s, 1H), 6.30 (s, 1H), 6.14 (s, 1H), 5.10 (s, 1H), 3.16 (s, 3H), 2.76-2.55 (m, 2H), 2.33 (s, 1H), 2.19 (d, J=11.9 Hz, 3H), 2.14-1.65 (m, 3H), 1.49 (d, J=6.7 Hz, 3H).

Example 5

The compound synthesized in the present invention:

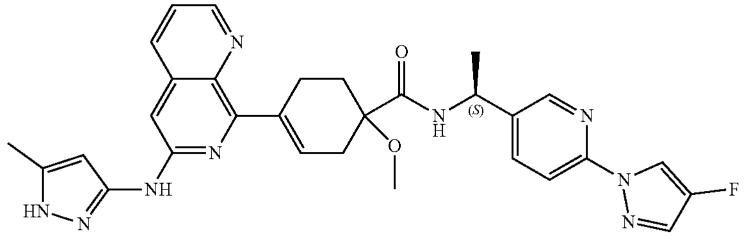

C8

The synthetic route and experimental process were as follows

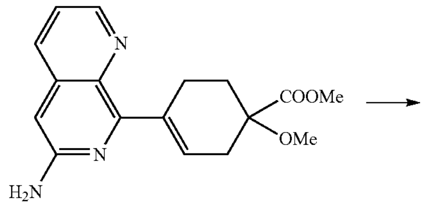

C3-4

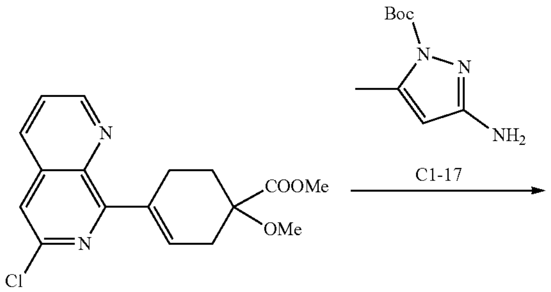

C8-1

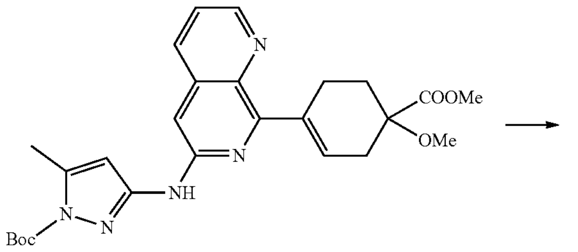

C8-2

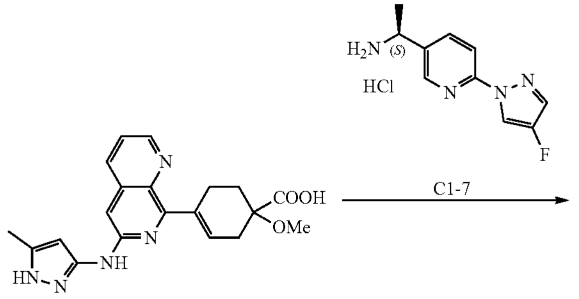

C8-3

-continued

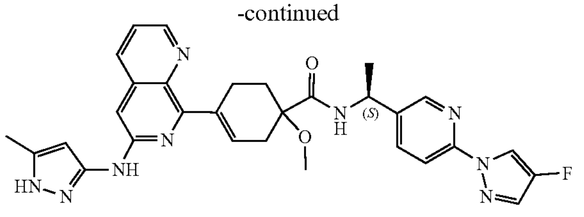

C8

1. Synthesis of C8-1

C3-4 (4.0 g, 12.8 mmol) and concentrated hydrochloric acid (60 mL) were added into a 250 mL single-neck flask, the temperature was reduced to −10° C. under ice salt bath, and $NaNO_2$ (4.4 g, 63.9 mmol) aqueous solution was slowly added. Stirred for 30 min under temperature of below 0° C., CuCl (6.3 g, 63.9 mmol) suspended in concentrated hydrochloric acids was added dropwise, then transferred to room temperature to react for 1 h. LC-MS showed that the reaction was completed. The reaction solution was slowly poured into ammonia water, extracted with DCM for 3 times. Organic phase was washed with saturated brine, dried over anhydrous sodium sulfate, evaporated, and purified by column chromatography to obtain 2.3 g product.

2. Synthesis of C8-2

C8-1 (487 mg, 1.5 mmol), C1-17 (433 mg, 2.2), $Pd_2(dba)_3$ (137 mg, 0.15 mmol), t-BuXPhos (127 mg, 0.3 mmol), DBU (456 mg, 3 mmol) and $(CH_3OCH_2)_2$ (8 mL) were added into a 50 mL single-neck flask to react at 60° C. overnight under $N_2$ atmosphere. LC-MS showed that the reaction was completed, concentrated, and purified by column chromatography to obtain 525 mg of crude product.

3. Synthesis of C8-3

C8-2 (475 mg, 0.963 mmol), $LiOH \cdot H_2O$ (121 mg, 2.89 mmol), THF/MeOH/$H_2O$ (7 mL/7 mL/4 mL) were added to a 50 mL single-neck flask to react at 60° C. overnight. LC-MS showed that the reaction was completed, and 481 mg of crude product was obtained by concentration.

4. Synthesis of C8

C8-3 (390 mg, 1 mmol), C1-7 (280 mg, 1 mmol), DMF (6 mL) and diisopropylethylamine (1.03 g, 8 mmol) were added into a 50 mL single-neck flask, then HATU (570 mg, 1.5 mmol) was added under stirring at room temperature, and reacted at 25° C. for 1 h. LC-MS showed that the reaction was completed. The reaction solution was poured into water (60 mL), extracted with ethyl acetate for three times, washed with saturated brine, dried over anhydrous sodium sulfate, evaporated, and purified by column chromatography to obtain C8 (291 mg, purity: 95.3%), [M+H]: 568.3.

Nuclear magnetic analysis data of compound C8: 1H NMR (400 MHz, DMSO) δ 11.77 (s, 1H), 9.16 (d, J=3.9 Hz, 1H), 8.70 (ddd, J=4.5, 1.7, 0.8 Hz, 1H), 8.66-8.55 (m, 2H), 8.47 (t, J=2.5 Hz, 1H), 8.09 (d, J=8.5 Hz, 1H), 8.03 (ddd, J=8.0, 5.5, 2.3 Hz, 1H), 7.91 (ddd, J=13.5, 6.4, 2.8 Hz, 2H), 7.74 (s, 1H), 7.47 (ddd, J=8.4, 4.0, 2.3 Hz, 1H), 6.66 (s, 1H), 5.86 (d, J=5.6 Hz, 1H), 5.19-5.04 (m, 1H), 3.19 (d, J=3.3 Hz, 3H), 2.84-2.52 (m, 4H), 2.21 (d, J=3.8 Hz, 3H), 2.19-1.90 (m, 2H), 1.51 (dd, J=7.0, 2.2 Hz, 3H).
Example 6
The compound synthesized in the present invention:
C9
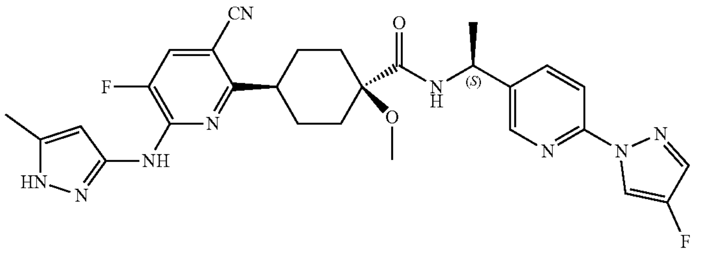
C10
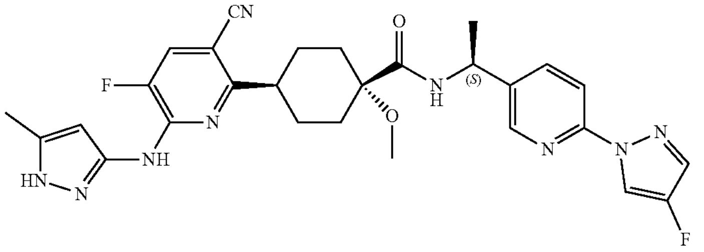
C11
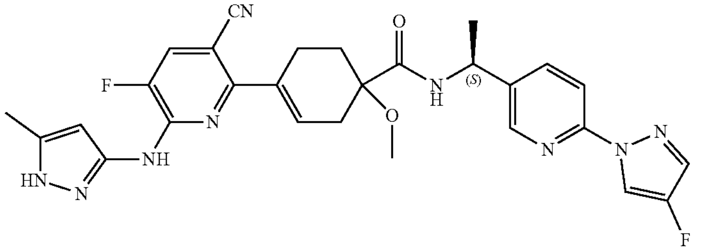
The synthetic route and experimental process were as follows
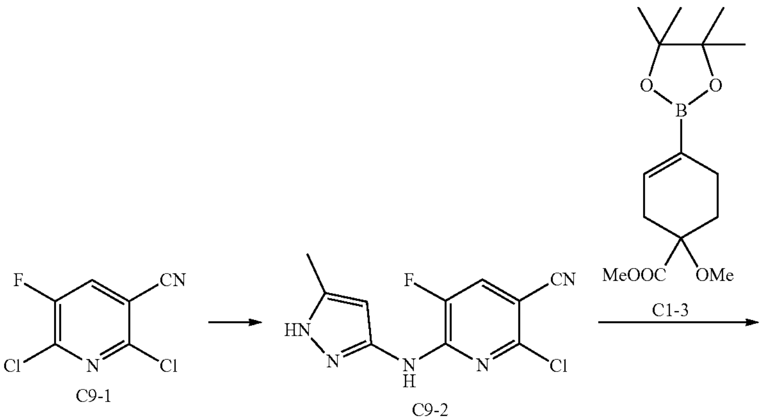
C1-3
C9-1
C9-2

-continued
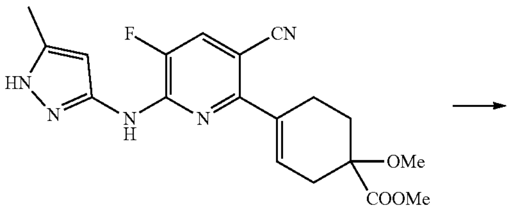
C9-3
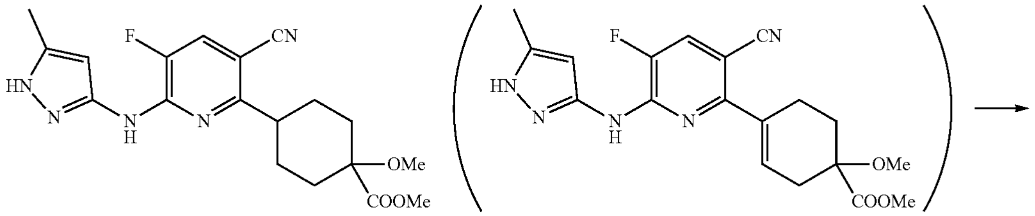
C9-4 C9-3
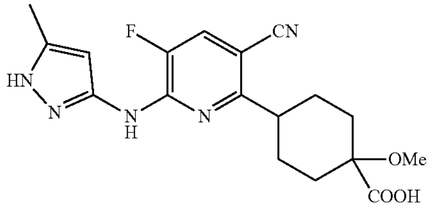
C9-5
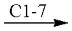
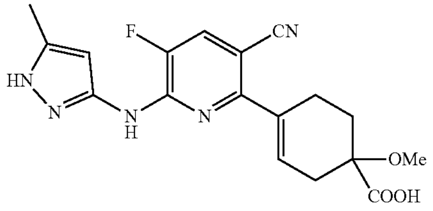
C9-6
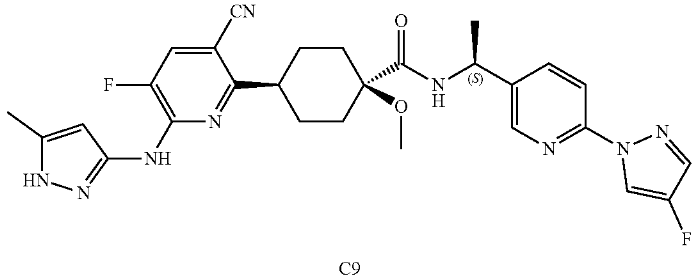
C9
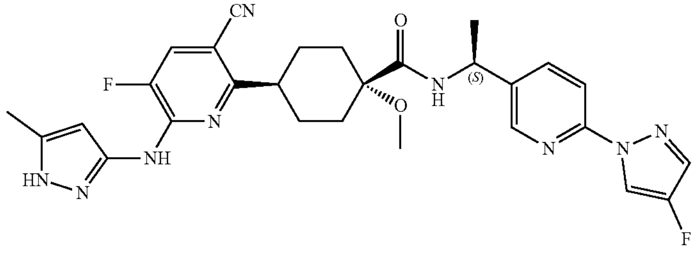
C10

-continued

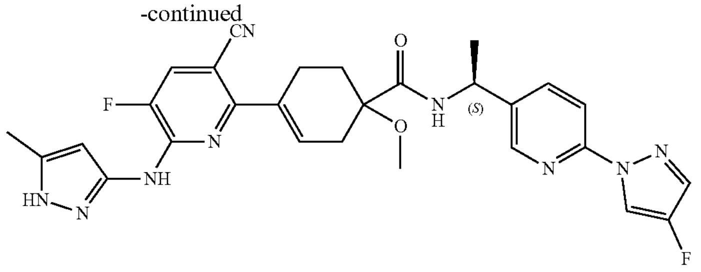

C11

1. Synthesis of C9-2

3-amino-5-methylpyrazole (427 mg, 4.4 mmol), C9-1 (764 mg, 4 mmol), DMSO (8 mL) and diisopropylethylamine (581 mg, 4.5 mmol) were added into a 250 mL single-neck flask to react at 90° C. for 4 h. LC-MS showed that the reaction was completed, the reaction solution was poured into water (100 mL) under stirring, and solid was precipitated, then filtered. The filter cake was washed with water, and dried to obtain 1.14 g of product.

2. Synthesis of C9-3

C9-2 (796 mg, 3.16 mmol), C1-3 (935 mg, 3.16 mmol), $Pd(PPh_3)_4$ (365 mg, 0.32 mmol), $K_2CO_3$ (654 mg, 4.74 mmol) and dioxane/$H_2O$ (9 mL/1.5 mL) were added into a 50 mL single-neck flask to react at 100° C. overnight under the protection of $N_2$. LC-MS showed that the reaction was completed. The reaction solution was poured into water (100 mL) under stirring, extracted with ethyl acetate for three times. Organic phase was washed with saturated brine, dried over anhydrous sodium sulfate, concentrated, and purified by column chromatography to obtain 775 mg of product.

3. Synthesis of C9-4

C12-3 (700 mg, 1.8 mmol), $Pd(OH)_2/C$ (10%, 350 mg) and MeOH (15 mL) were added into a 50 mL single-neck flask to react at 50° C. overnight under $H_2$ (60 psi) atmosphere. LC-MS showed that most of the raw materials were finished, then filtered, concentrated and purified by column chromatography to obtain the mixture of C9-3 and C9-4 (242 mg) which was directly used for the next reaction.

4. Synthesis of C9-5 and C9-6

A mixture of C9-3 and C9-4 (230 mg, 0.59 mmol), $LiOH{\cdot}H_2O$ (100 mg, 2.4 mmol) and MeOH/$H_2O$ (3 mL/1.5 mL) were added into a 50 mL single-neck flask to react at 50° C. overnight. LC-MS showed that the reaction was completed, and concentrated to obtain 250 mg of crude product which was directly used for the next reaction.

5. Synthesis of Compounds C9, C10 and C11

A mixture of C9-5 and C9-6 (114 mg, 0.3 mmol), C1-7 (66 mg, 0.24 mmol), and DMF (3 mL) were added into a 50 mL single-neck flask, then diisopropylethylamine (397 mg, 3 mmol), PyBop (234 mg, 0.45 mmol), and HOBT (84 mg, 0.4 mmol) were added under stirring at room temperature, then reacted at room temperature for 30 min. LC-MS showed that the reaction was completed. The reaction solution was poured into water (30 mL), and extracted with ethyl acetate for three times. Organic phase was washed with saturated brine, dried over anhydrous sodium sulfate, concentrated to obtain crude product which was separated to obtain compound C11 (10 mg, purity: 96.7%), [M+H]: 560.2; compound C10 (19 mg, purity: 97.5%), [M+H]: 562.3; compound C9 (17 mg, purity: 97.1%), [M+H]: 562.3.

Example 7

The compound synthesized in the present invention:

C12

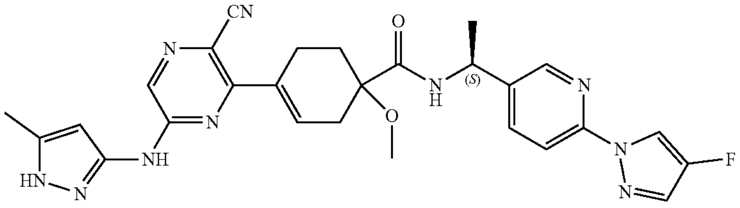

C13

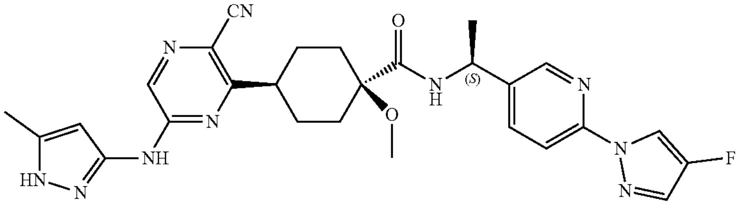

The synthetic route and experimental process were as follows:
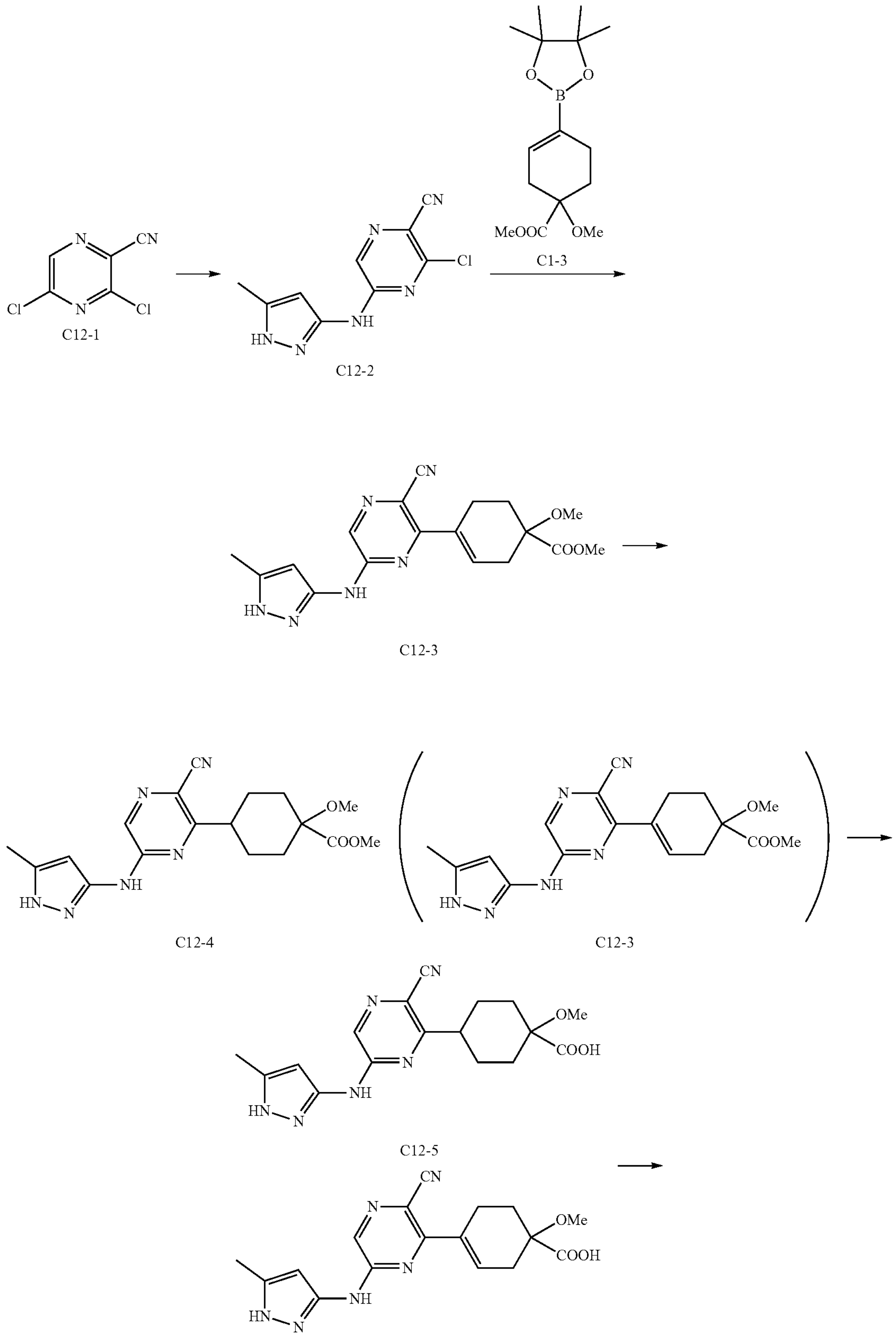
C12-1
C12-2
C1-3
C12-3
C12-4
C12-3
C12-5
C12-6

-continued

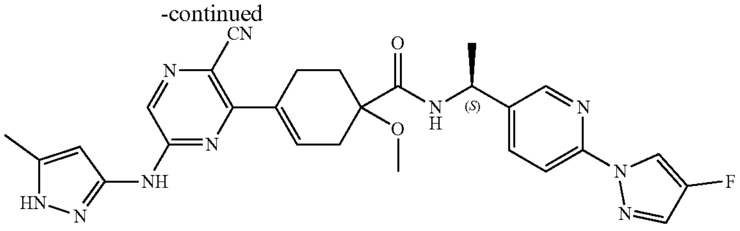

C12 and

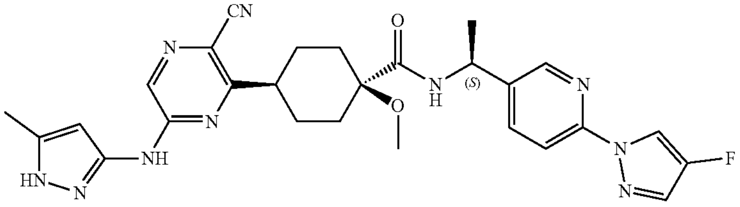

C13

1. Synthesis of C12-2

3-amino-5-methylpyrazole (426 mg, 4.4 mmol), C12-1 (696 mg, 4 mmol), DM (4 mL) and diisopropylethylamine (1.032 g, 8 mmol) were added into a 250 mL single-neck flask to react at 90° C. for 5 h. LC-MS showed that the reaction was completed, the reaction solution was poured into water (40 mL) under stirring, and solid was precipitated, then filtered. The filter cake was washed with water, and dried to obtain 910 mg of product.

2. Synthesis of C12-3

C12-2 (585 mg, 2.5 mmol), C1-3 (814 mg, 2.75 mmol), $Pd(PPh_3)_4$ (289 mg, 0.25 mmol), $K_2CO_3$ (690 mg, 5 mmol) and dioxane/$H_2O$ (30 mL/4 mL) were added into a 50 mL single-neck flask to react at 100° C. overnight under the protection of $N_2$. LC-MS showed that the reaction was completed. The reaction solution was poured into water (100 mL) under stirring, extracted with ethyl acetate for three times. Organic phase was washed with saturated brine, dried over anhydrous sodium sulfate, concentrated, and purified by column chromatography to obtain 747 mg of product.

3. Synthesis of C12-4

C12-3 (747 mg, 2 mmol), $Pd(OH)_2/C$ (10%, 700 mg) and EtOH (100 mL) were added into a 150 mL single-neck flask to react at 80° C. overnight under $H_2$ atmosphere. LC-MS showed that most of the raw materials were finished, then filtered, concentrated and purified by column chromatography to obtain 291 mg mixture of C12-3 and C12-4 which was directly used for the next reaction.

4. Synthesis of C12-5 and C12-6

A mixture of C12-3 and C12-4 (291 mg, 0.79 mmol), $LiOH{\cdot}H_2O$ (132 mg, 3.15 mmol) and MeOH/$H_2O$ (15 mL/3 mL) were added into a 50 mL single-neck flask to react at 50° C. overnight. LC-MS showed that the reaction was completed, and concentrated to obtain 393 mg of crude product which was directly used for the next reaction.

5. Synthesis of C12 and C13

A mixture of C12-5 and C12-6 (197 mg, 0.55 mmol), C1-7 (122 mg, 0.44 mmol), and DMF (10 mL) were added into a 50 mL single-neck flask, then diisopropylethylamine (705 mg, 5.5 mmol), PyBop (426 mg, 0.81 mmol), and HOBT (150 mg, 1.08 mmol) were added under stirring at room temperature, and then reacted at room temperature for 30 min. LC-MS showed that the reaction was completed. The reaction solution was poured into water (100 mL), and extracted with ethyl acetate for three times. Organic phase was washed with saturated brine, dried over anhydrous sodium sulfate, concentrated, and purified by column chromatography to obtain C13 (26 mg, purity: 96.5%), C12 (13 mg, purity: 97.5%).

Example 8

The compound synthesized in the present invention

C14

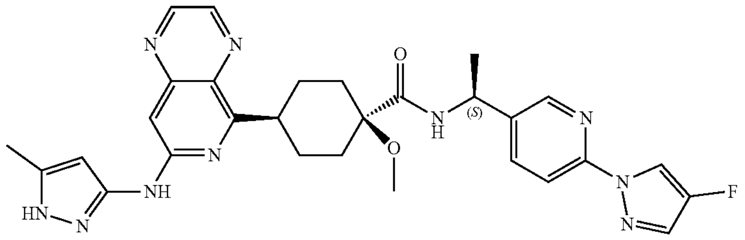

The synthetic route and experimental process were as follows:

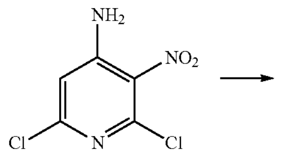

C14-1

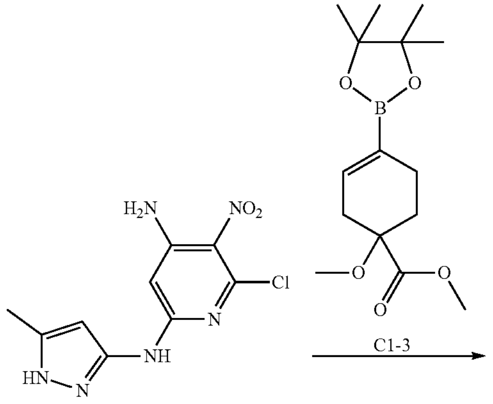

C14-2

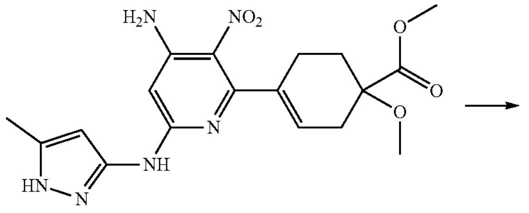

C14-3

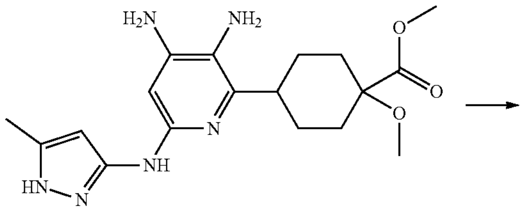

C14-4

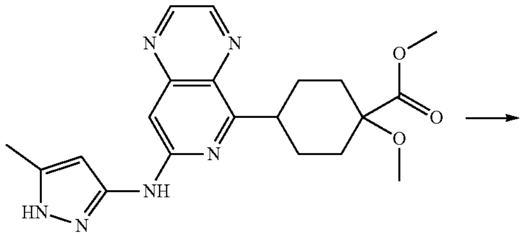

C14-5

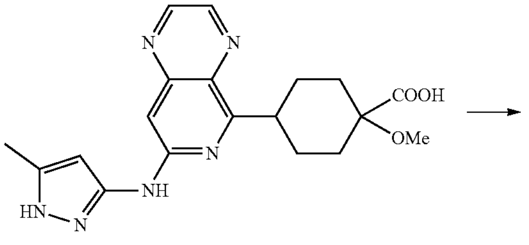

C14-6

-continued

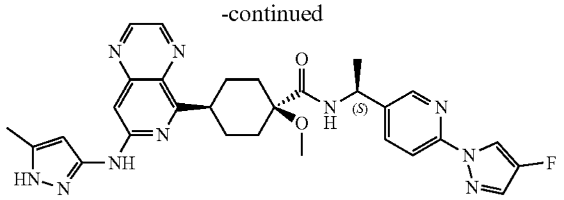

C14

1. Synthesis of C14-2

3-amino-5-methylpyrazole (540 mg, 5.5 mmol), C14-1 (1.04 g, 5 mmol), DMSO (10 mL) and diisopropylethylamine (1.29 g, 10 mmol) were added into a 250 mL single-neck flask, and reacted at 90° C. for 5 h. LC-MS showed that the reaction was completed, the reaction solution was poured into water (40 mL) under stirring, and solid was precipitated, then filtered. The filter cake was washed with water, and dried to obtain 1.2 g of product.

2. Synthesis of C14-3

C14-2 (774 mg, 2.88 mmol), C1-3 (1.7 g, 5.75 mmol), $Pd(PPh_3)_4$ (999 mg, 0.864 mmol), $K_2CO_3$ (1.19 g, 8.64 mmol) and dioxane/$H_2O$ (40 mL/10 mL) were added into a 100 mL single-neck flask to react at 90° C. overnight under the protection of $N_2$. LC-MS showed that the reaction was completed. The reaction solution was poured into water (100 mL) under stirring, extracted with ethyl acetate for three times. Organic phase was washed with saturated brine, dried over anhydrous sodium sulfate, concentrated, and purified by column chromatography to obtain 1.16 g of product.

3. Synthesis of C14-4

C14-3 (302 mg, 0.74 mmol), $Pd(OH)_2/C$ (10%, 30 mg) and MeOH (20 mL) were added into a 50 mL single-neck flask to react at 50° C. under $H_2$ atmosphere. LC-MS showed that the reaction was completed, filtered, concentrated, and purified by column chromatography to obtain 90 mg of product.

4. Synthesis of C14-5

C14-4 (374 mg, 1 mmol), glyoxal (174 mg, 1.2 mmol) and ethanol (10 mL) were added into a 50 mL single-neck flask to react at room temperature overnight. LC-MS showed that the reaction was completed, concentrated, and purified by column chromatography to obtain 94 mg of crude product.

5. Synthesis of C14-6

C14-5 (94 mg, 0.24 mmol), $LiOH{\cdot}H_2O$ (20 mg, 0.48 mmol) and MeOH/$H_2O$ (2 mL/0.5 mL) were added into a 50 mL single-neck flask to react at 50° C. for 48 h. LC-MS showed that the reaction was completed, and concentrated to obtain 106 mg of crude product which was directly used for the next reaction.

6. Synthesis of C14

Crude product C14-6 (106 mg, 0.17 mmol), C1-7 (52 mg, 1.97 mmol), DMF (1 ml), and diisopropylethylamine (176 mg, 1.36 mmol) were added into a 50 mL single-neck flask, stirred for 10 min at room temperature, and PyBop (133 mg, 0.26 mmol) was added to react at room temperature for 30 min. LC-MS showed that the reaction was completed. The reaction solution was poured into water (100 mL), and extracted with ethyl acetate for three times. Organic phase was washed with saturated brine, dried over anhydrous sodium sulfate, concentrated, and purified by column chromatography to obtain crude product which was separated to obtain C14 (37 mg, purity: 98%).

Example 9

The compound synthesized in the present invention:

C15

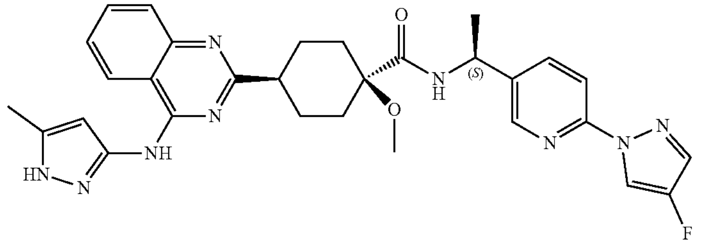

The synthetic route and experimental process were as follows:

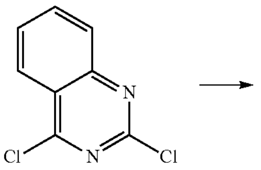

C15-1

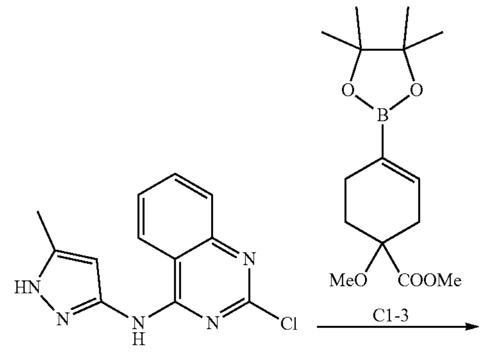

C15-2

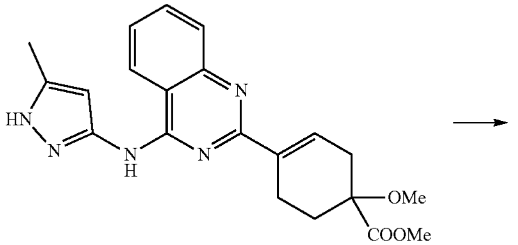

C15-3

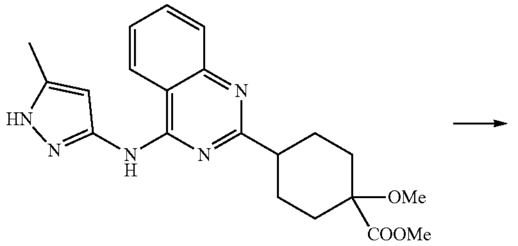

C15-4

-continued

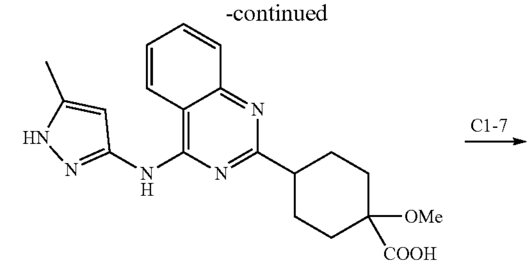

C15-5

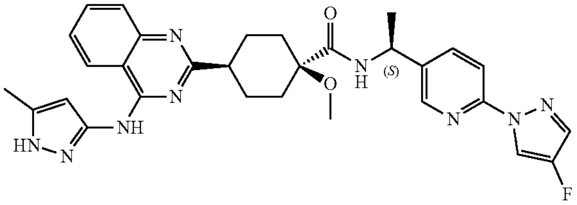

C15

1. Synthesis of C15-2

C15-1 (1 g), triethylamine (1.45 mL), ethanol (20 mL) and tetrahydrofuran (5 mL) were added into a 100 mL single-neck flask and 3-amino-5-methylpyrazole (530 mg) was added in batches under stirring, and reacted overnight at room temperature under stirring. TLC showed the reaction was completed, concentrated. The residue was added into water, stirred for 15 minutes, filtered. The filter cake was washed with ether, and dried to obtain compound C18-2.

2. Synthesis of C15-3

C15-2 (973 mg, 3.75 mmol), C1-3 (1.66 g, 5.62 mmol), $Pd(PPh_3)_4$ (2.17 g, 1.875 mmol), $Cs_2CO_3$ (3.67 g, 11.25 mmol) and dioxane/$H_2O$ (15 mL/3 mL) were added into a 100 mL single-neck flask to react at 110° C. overnight under the protection of $N_2$. LC-MS showed that the reaction was completed. The reaction solution was poured into water (100 mL) under stirring, extracted with ethyl acetate for three times. Organic phase was washed with saturated brine, dried over anhydrous sodium sulfate, concentrated, and purified by column chromatography to obtain 895 mg of product.

3. Synthesis of C15-4

C15-3 (875 mg, 2.23 mmol), $Pd(OH)_2/C$ (10%, 170 mg) and MeOH (50 mL) were added into a 50 mL single-neck flask to react at 50° C. under $H_2$ atmosphere. LC-MS showed that the reaction was completed, filtered, concentrated to obtain 724 mg of crude product.

4. Synthesis of C15-5

C15-4 (675 mg, 1.7 mmol), $LiOH \cdot H_2O$ (145 mg, 3.4 mmol) and $MeOH/H_2O$ (5 mL/1 mL) were added into a 50 mL single-neck flask to react at 50° C. overnight. LC-MS showed that the reaction was completed, and concentrated to obtain 210 mg of crude product which was directly used for the next reaction.

5. Synthesis of C15

C15-5 (148 mg, 0.39 mmol), C1-7 (119 mg, 0.43 mmol), DMF (2 mL), and diisopropylethylamine (401 mg, 3.1 mmol) were added into a 50 mL single-neck flask, stirred for 10 min at room temperature, and PyBop (304 mg, 0.58 mmol) was added to react at room temperature for 30 min. LC-MS showed that the reaction was completed. The reaction solution was poured into water (30 mL), and extracted with ethyl acetate for three times. Organic phase was washed with saturated brine, dried over anhydrous sodium sulfate, concentrated, and purified by column chromatography to obtain C15 (10 mg, purity: 91%).

Example 10

The compound synthesized in the present invention:

C16

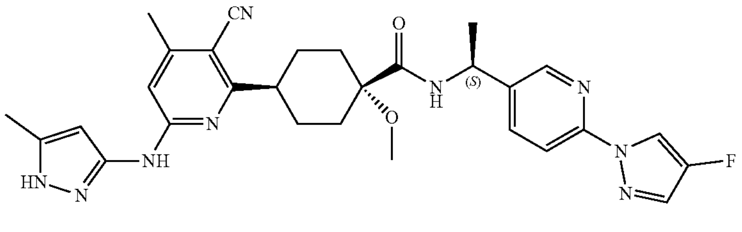

C17

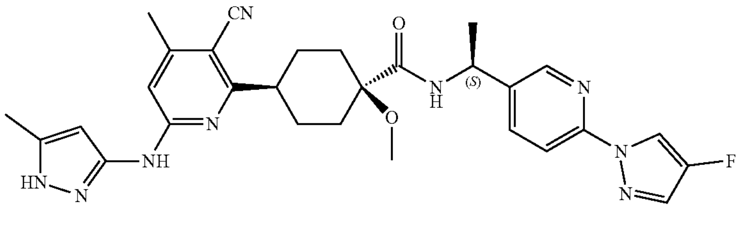

The synthetic route and experimental process were as follows:

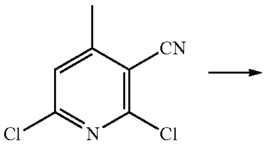

C16-1

C16-2

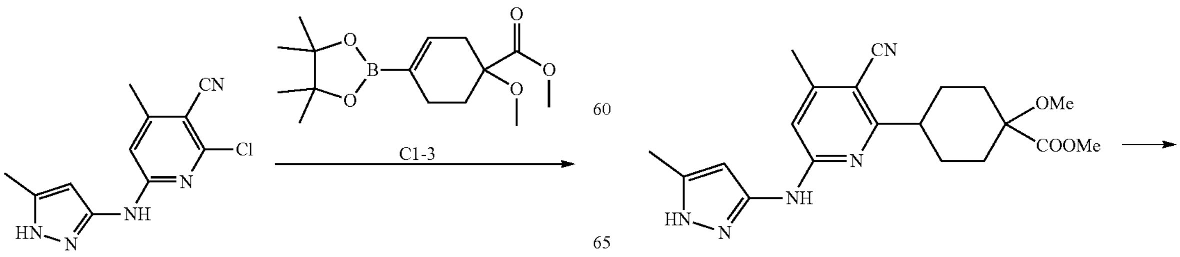

C16-4

-continued

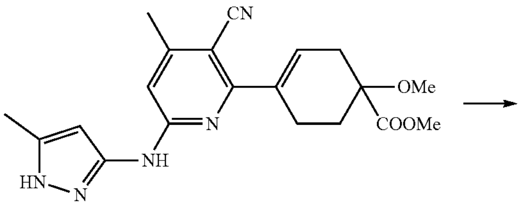

C16-3

-continued

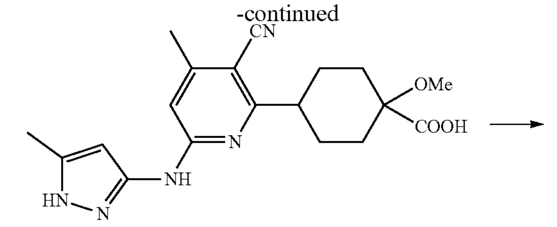

C16-5

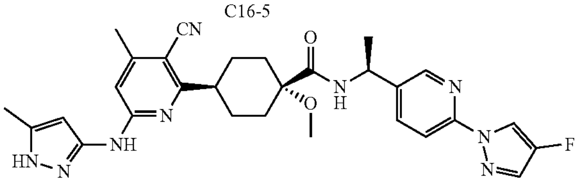

C16 and

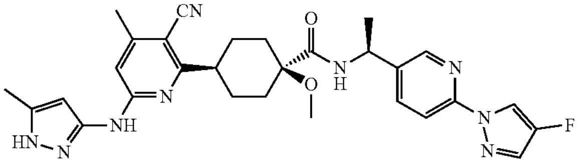

C17

1. Synthesis of C16-2

C16-1 (20 mmol, 3.8 g), 3-amino-5-methylpyrazole (24 mmol, 2.4 g), diisopropylethylamine (40 mmol, 5.2 g) and DMSO (30 mL) were added to a 50 mL reaction flask to react at 90° C. for 16 h under argon protection. TLC showed that the reaction was completed. Water and ethyl acetate were added, the aqueous phase was extracted with ethyl acetate. The organic phases were combined, washed with saturated saline, dried and concentrated, and recrystallized by tetrahydrofuran/tert-butyl methyl ether to obtain 3 g of product.

2. Synthesis of C16-3

C16-2 (1 g, 4 mmol), C1-3 (1.3 g, 4.4 mmol), $Pd(PPh_3)_4$ (400 mg, 0.4 mmol), potassium carbonate (1 g, 6 mmol), dioxane (12 mL) and water (3 mL) were added into a 100 mL three-neck flask under the protection of nitrogen, replaced with nitrogen for three times, then the reaction solution was stirred at 100° C. for 16 hours. TLC and LC-MS showed the reaction was completed, filtered and concentrated under reduced pressure, then diluted with water (20 mL), extracted with ethyl acetate for three times. Organic phase was washed with saturated brine, dried, concentrated under reduced pressure to obtain crude product, and purified by silica gel column chromatography (developing agent: dichloromethane/methanol=30:1) to obtain 700 mg of product.

3. Synthesis of C16-4

C16-3 (690 mg, 1.6 mmol) and ethanol (10 mL) were added into a 50 mL single-neck flask, and then 10% $Pd(OH)_2/C$ (300 mg) was carefully added, the reaction vessel was replaced by hydrogen for three times, and then reacted at 50° C. for 100 h under the protection of hydrogen. LC-MS detection showed the reaction was completed, filtered by the diatomite slowly, the filter cake was washed with methanol, and the filtrate was concentrated to obtain 650 mg of product.

4. Synthesis of C16-5

C16-4 (540 mg, 1.1 mmol), methanol (3 mL), THF (3 mL), $H_2O$ (2 mL) and LiOH (140 mg, 3.5 mmol) were added into a 50 mL single-neck flask, and the reaction solution was stirred at 65° C. for 16 h. LC-MS detection showed the reaction was completed, it was concentrated under reduced pressure, diluted with water (1 mL), extracted with ether, water phase was adjusted to pH=4-5 with 2M HCl, concentrated and dried to obtain 500 mg of product which was directly used for the next step.

5. Synthesis of C16 and C17

C16-5 (307 mg, 0.83 mmol), HATU (253 mg, 1 mmol), diisopropylethylamine (0.7 mL, 5 mmol) and DMF (6 mL) were added into a 10 mL reaction tube and stirred at room temperature for 10 min, then C1-7 (242 mg, 1 mmol) was added and stirred at room temperature for 3 h. TLC and LC-MS showed that the reaction was completed, diluted with water (3 mL), extracted with ethyl acetate for 3 times. Organic phase was washed with saturated brine, dried, concentrated under reduced pressure to obtain crude product, purified by column chromatography (DCM/MeOH=10/1) to obtain cis-trans isomers, and then isomers C16 (14 mg) and C17 (6 mg) was obtained by preparation-separation.

C16 (LC: T=16. 17 min; purity: 97.21%)

Nuclear magnetic analysis data of compound C16: 1H NMR (400 MHz, Chloroform-d) δ 8.40 (d, J=2.4 Hz, 1H), 8.36 (d, J=4.5 Hz, 1H), 7.89 (d, J=8.5 Hz, 1H), 7.78 (dd, J=8.5, 2.4 Hz, 1H), 7.56 (d, J=4.4 Hz, 1H), 7.35 (d, J=2.7 Hz, 1H), 6.99 (d, J=2.9 Hz, 1H), 6.91 (s, 1H), 6.74 (d, J=7.9 Hz, 1H), 5.26-5.16 (m, 1H), 3.75 (m, 1H), 3.24 (m, 3H), 3.15 (m, 1H), 2.42 (s, 3H), 2.30 (s, 3H), 1.98-1.62 (m, 8H), 1.54 (d, J=7.0 Hz, 3H).

C17 (LC: T=22. 57 min; purity: 97.47%)

Nuclear magnetic analysis data of compound C17: 1H NMR (400 MHz, Chloroform-d) δ 8.49-8.28 (m, 1H), 7.92 (d, J=8.5 Hz, 0H), 7.77 (dd, J=8.5, 2.4 Hz, 1H), 7.58 (d, J=4.3 Hz, 0H), 6.90-6.64 (m, 1H), 6.12 (s, 1H), 5.19 (p, J=7.3 Hz, 1H), 3.78-3.67 (m, 1H), 3.28 (s, 3H), 3.14 (m, 1H), 2.43 (s, 3H), 2.32 (s, 3H), 1.94-1.70 (m, 8H), 1.57 (d, J=7.0 Hz, 2H).

Example 11

The compound synthesized in the present invention:

C18

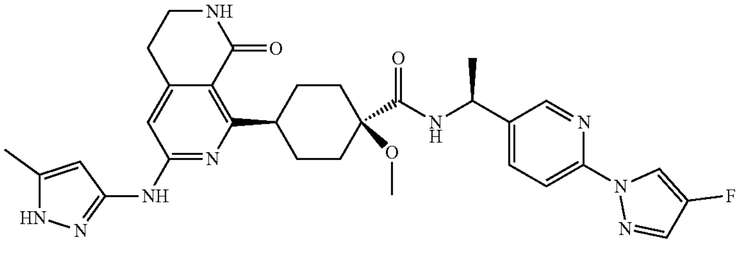

-continued
C19
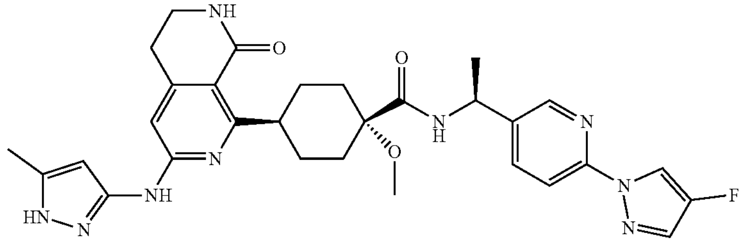
The synthetic route and experimental process were as follows:
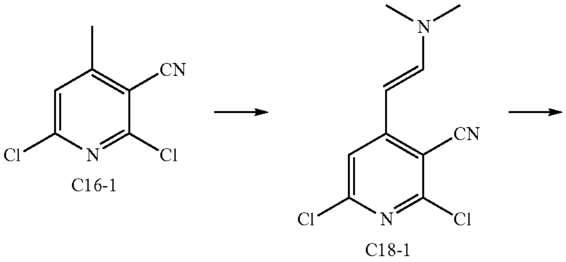
C16-1
C18-1
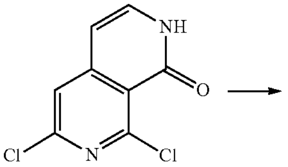
C18-2
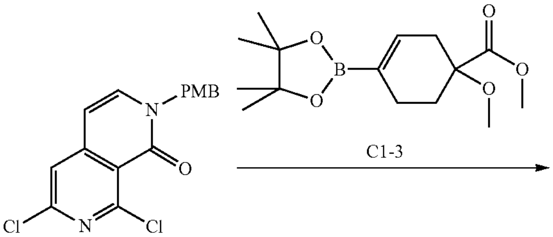
C1-3
C18-3
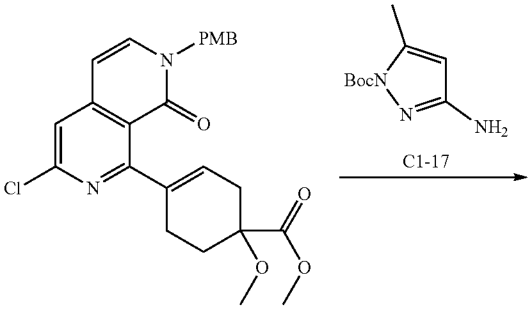
C1-17
C18-4
-continued
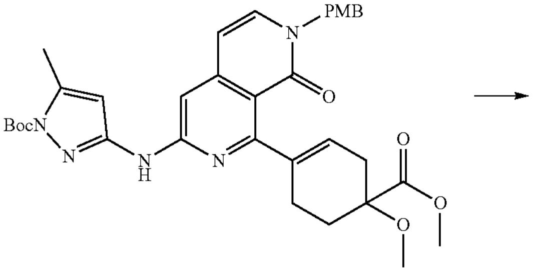
C18-5
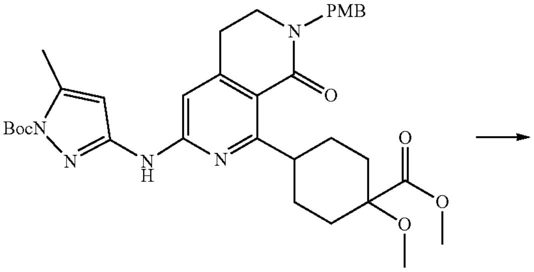
C18-6
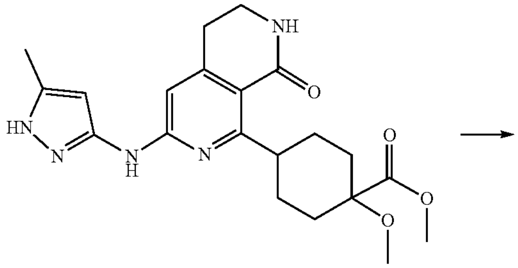
C18-7
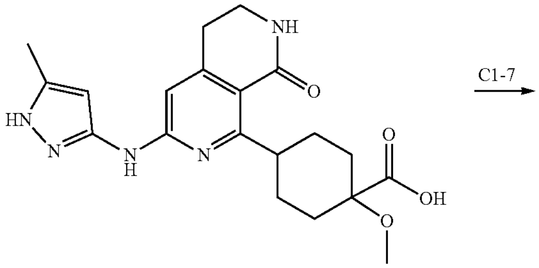
C1-7
C18-8

-continued

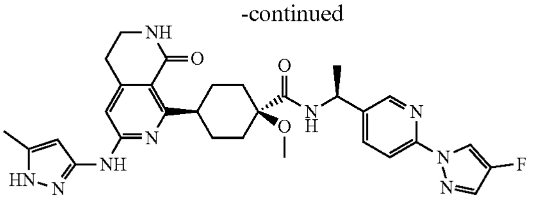

C18 and

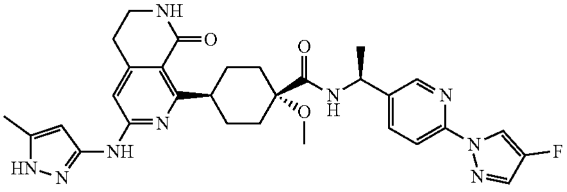

C19

1. Synthesis of C18-1

C16-1 (25 g, 133 mmol), N,N-dimethylformamide dimethylacetal (24 g, 200 mmol) and isopropanol (300 mL) were added sequentially into a 1 L three-neck flask under the protection of nitrogen, the reaction solution was stirred at 65° C. for 16 h. TLC and LC-MS showed that the reaction was completed. Cooled to room temperature, filtered, and the filter cake was washed with a small amount of ethyl acetate. It was concentrated under reduced pressure after filtration to obtain 30 g of product.

2. Synthesis of C18-2

C18-1 (25 g, 91 mmol) and concentrated hydrochloric acid (100 mL) were added into a 250 mL three-neck flask, the reaction solution was stirred at 45° C. for 16 h, and then cooled to room temperature. Ice water was added in the reaction, filtered, and the filter cake was washed with ice water and tert-butyl methyl ether to obtain crude product, which was purified by silica gel column chromatography (developing agent: dichloromethane/methanol/ammonia water=50:10:1) to obtain 10 g product.

3. Synthesis of C18-3

C18-2 (2.4 g, 12 mmol) and DMA (15 mL) were added into a 50 mL three-neck flask, and NaH (0.576 g, 14.4 mmol) was added in batches under ice bath. The reaction solution was stirred at 0° C. to room temperature for 30 minutes, then p-methoxybenzyl chloride (1.8 g, 15 mmol) was added, and the reaction solution was stirred at room temperature for 16 h. Water (5 mL) was added slowly under ice bath, extracted with ethyl acetate for three times. The DMA in organic phase was washed off with saturated saline, and the organic phase was dried, concentrated under reduced pressure to obtain crude product which was purified by silica gel column chromatography (developing agent: ethyl acetate/petroleum ether=1:10-1:1) to obtain 2.5 g of product.

4. Synthesis of C18-4

Starting materials C18-3 (1.8 g, 5.4 mmol), C1-3 (1.5 g, 5 mmol), $Pd(PPh_3)_4$ (600 mg, 0.54 mmol), potassium carbonate (1.8 g, 13 mmol), dioxane (20 mL) and water (4 mL) were added into a 100 mL three-neck flask under the protection of nitrogen, replaced with nitrogen for three times, then the reaction solution was stirred at 90° C. for 16 h. TLC and LC-MS showed the reaction was completed, and concentrated under reduced pressure after filtration, then diluted with water (20 mL), extracted with ethyl acetate for three times. Organic phase was washed with saturated brine, dried, concentrated under reduced pressure to obtain crude product which purified by silica gel column chromatography (developing agent: ethyl acetate/petroleum ether=1:10-1:3) to obtain 1.5 g of product.

5. Synthesis of C18-5

C18-4 (1.1 g, 2.4 mmol), C1-17 (700 mg, 3.6 mmol), $Pd_2(dba)_3$ (210 mg, 0.24 mmol), DBU (727 mg, 4.8 mmol), t-BuXphos (210 mg, 0.25 mmol) and ethylene glycol dimethyl ether (10 mL) were added into a 50 mL three-neck flask under nitrogen protection, and replaced with nitrogen for three times, and the reaction solution was stirred at 60° C. for 16 h. TLC showed that the reaction was completed, and concentrated under reduced pressure after filtration, diluted with water (5 mL), extracted with ethyl acetate for three times. Organic phase was washed with saturated brine, dried, concentrated under reduced pressure to obtain crude product which was purified by silica gel column chromatography (developing agent: ethyl acetate/petroleum ether=1:10-1:3) to obtain 900 mg of product.

6. Synthesis of C18-6

C18-5 (500 mg, 0.8 mmol) and ethanol (10 mL) were added into a 50 mL single-neck flask, and then 10% Pd $(OH)_2/C$ (300 mg) was carefully added, the reaction vessel was replaced by hydrogen for three times, and then reacted at 65° C. for 100 h under the protection of hydrogen. LC-MS detection showed the reaction was completed, filtered by the diatomite slowly, the filter cake was washed with methanol, and the filtrate was concentrated to obtain 500 mg of crude product.

7. Synthesis of C18-7

C18-6 (400 mg, 0.58 mmol) and trifluoroacetic acid (10 mL) were successively added into a 50 mL single-neck flask, and the reaction solution was stirred at 80° C. for 16 h. LC-MS detection showed the reaction was completed, concentrated under reduced pressure and dried to obtain the trifluoroacetate of the product which was directly used for the next step.

8. Synthesis of C18-8

C18-7 (410 mg, 0.55 mmol), methanol (3 mL), THF (3 mL), $H_2O$ (2 mL) and LiOH (230 mg, 5.5 mmol) were added into a 50 mL single-neck flask, and the reaction solution was stirred at 65° C. for 16 h. LC-MS detection showed the reaction was completed, it was concentrated under reduced pressure, diluted with water (5 mL), extracted with ether, water phase was adjusted to pH=4-5 with 2M HCl, concentrated and dried to obtain 400 mg of crude product which was directly used for the next step.

9. Synthesis of C18 and C19

C18-8 (400 mg, 1.0 mmol), HATU (760 mg, 2 mmol), diisopropylethylamine (650 mg, 5 mmol) and DMF (5 mL) were added into a 10 mL reaction tube and stirred at room temperature for 10 min, then C1-7 (320 mg, 1.2 mmol) was added and stirred at room temperature for 16 h. TLC and LC-MS showed that the reaction was completed, diluted with water (3 mL), extracted with ethyl acetate for three times. Organic phase was washed with saturated saline, dried, concentrated under reduced pressure to obtain crude product, purified by column chromatography (DCM/MeOH=20/1) to obtain 190 mg of cis-trans isomers, and then 100 mg of compound C18 and 23 mg of compound C19 were obtained by preparation and separation.

Compound C18 (LC: T=30. 51 min; purity: 98.18%)

Nuclear magnetic analysis data of compound C18: 1H NMR (400 MHz, Chloroform-d) δ 8.41 (s, 1H), 8.35 (d, J=4.6 Hz, 1H), 7.88 (d, J=8.6 Hz, 1H), 7.82-7.64 (m, 1H), 7.56 (d, J=4.4 Hz, 1H), 7.35 (d, J=2.7 Hz, 1H), 7.09 (td, J=9.1, 8.3, 2.5 Hz, 1H), 6.75 (d, J=11.8 Hz, 1H), 6.09 (s, 1H), 5.07-4.75 (m, 1H), 4.13 (s, 1H), 3.49 (s, 2H), 3.23 (s, 3H), 2.85 (d, J=7.7 Hz, 2H), 2.68-2.46 (m, 1H), 2.30 (s, 3H), 2.04 (m, 4H), 1.86 (m, 4H), 1.56 (d, J=7.0 Hz, 3H).
Compound C19 (LC: T=32. 26 min; purity: 94.58%)
Nuclear magnetic analysis data of compound C19: 1H NMR (400 MHz, Chloroform-d) δ 8.38 (t, J=4.3 Hz, 2H), 7.90 (d, J=8.5 Hz, 1H), 7.76 (dd, J=8.5, 2.3 Hz, 1H), 7.58 (d, J=4.3 Hz, 1H), 6.87 (d, J=8.4 Hz, 1H), 6.65 (s, 1H), 6.08 (s, 1H), 5.17 (q, J=7.3 Hz, 1H), 4.15 (m, 1H), 3.41 (m, 2H), 3.30 (s, 3H), 2.84 (m, 2H), 2.31 (s, 3H), 1.98-1.68 (m, 8H), 1.55 (d, J=7.0 Hz, 3H).
Example 12
The compound synthesized in the present invention:
C20
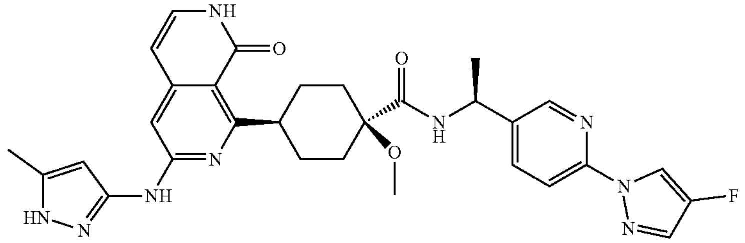
C21
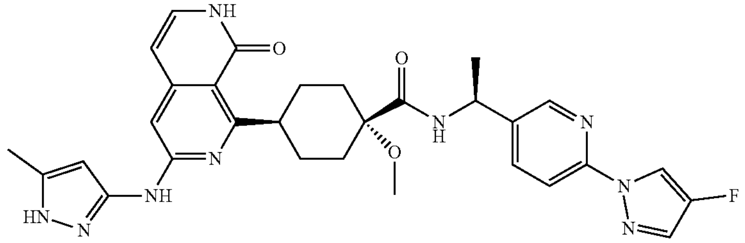
The synthetic route and experimental process were as follows:
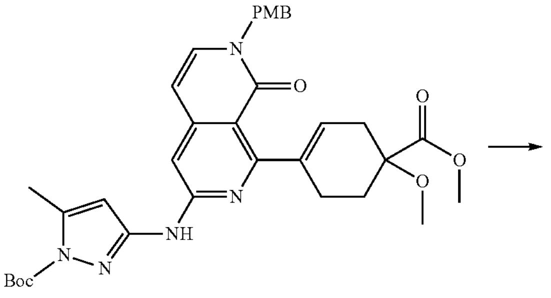
C18-5
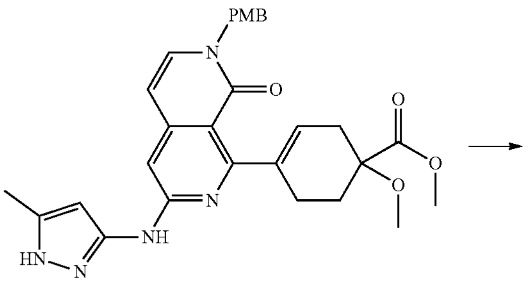
C20-1
-continued
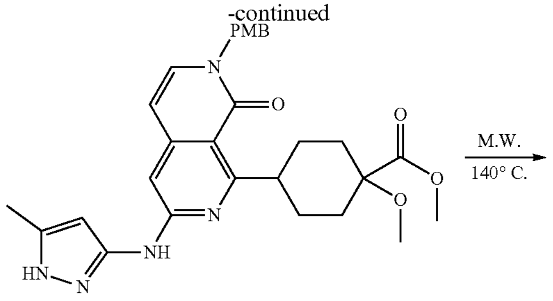
C20-2
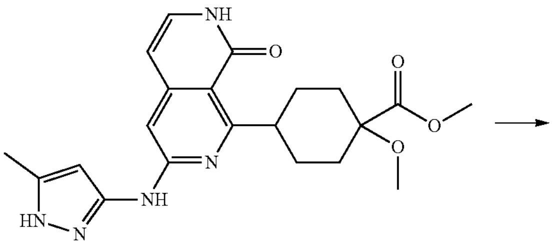
C20-3

-continued

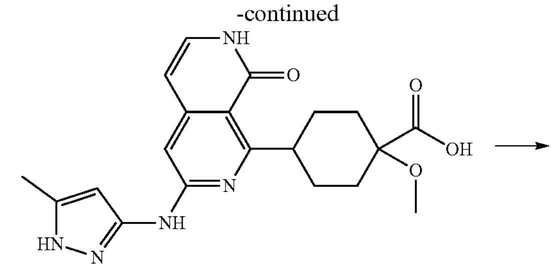

C20-4

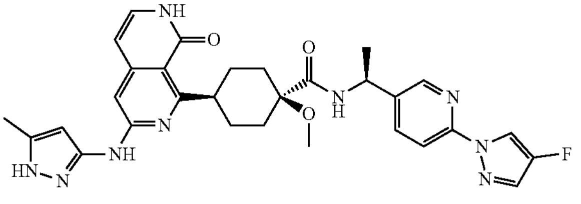

C20 and

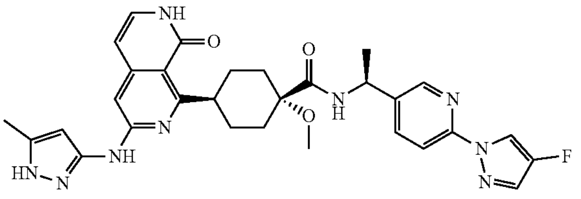

C21

1. Synthesis of C20-1

C18-5 (630 mg, 1 mmol) and trifluoroacetic acid (10 mL) were successively added into a 50 mL single-neck flask, and the reaction solution was stirred at 20° C. for 16 h. LC-MS detection showed the reaction was completed, trifluoroacetic acid was removed by concentration under reduced pressure, then dichloromethane (20 mL) was added. Organic phase was washed with saturated sodium carbonate (5 mL), separated, and concentrated to obtain 420 mg of crude product which was directly used for the next step.

2. Synthesis of C20-2

C20-2 (400 mg, 0.8 mmol) and methanol (10 mL) were added into a 50 mL single-neck flask, and 10% $Pd(OH)_2/C$ (100 mg) was carefully added under nitrogen atmosphere, the reaction vessel was replaced three times under hydrogen, then reacted at 50° C. for 16 h under the protection of hydrogen. Then it was cooled to room temperature, filtered through diatomite slowly, the filter cake was washed with methanol, and the filtrate was concentrated to obtain 400 mg of product.

3. Synthesis of C20-3

C20-2 (400 mg, 0.8 mmol) and trifluoroacetic acid (3 mL) were successively added into microwave tube to react at 140° C. for 15 minutes under microwave. LC-MS detection showed the reaction was completed, concentrated under reduced pressure and dried to obtain 300 mg trifluoroacetate of the product which was directly used for the next step.

4. Synthesis of C20-4

C20-3 (300 mg, 0.58 mmol), methanol (3 mL), THF (3 mL), $H_2O$ (2 mL) and $LiOH{\cdot}H_2O$ (170 mg, 4 mmol) were successively added into a 50 mL single-neck flask. The reaction solution was stirred at 65° C. for 16 h. LC-MS detection showed the reaction was completed, it was concentrated under reduced pressure, diluted with water (1 mL), impurities were extracted with ether, water phase was adjusted to pH=4-5 with 2M HCl, concentrated and dried to obtain 310 mg of product which was directly used for the next step.

5. Synthesis of Compounds C20 and C21

Crude product C20-4 (200 mg, 0.5 mmol), HATU (380 mg, 1 mmol), diisopropylethylamine (330 mg, 2.5 mmol) and DMF (2 mL) were added into a 10 mL reaction tube and stirred at room temperature for 10 min, then C1-7 (160 mg, 0.6 mmol) was added and stirred at room temperature for 16 h. TLC and LC-MS showed that the reaction was completed, diluted with water (3 mL), extracted with ethyl acetate for three times. Organic phase was washed with saturated brine, dried, and concentrated under reduced pressure to obtain 180 mg of crude product. 13 mg of compound C20 and 8 mg of compound C21 were obtained by preparation and separation of the crude product.

Example 13

The compound synthesized in the present invention:

C22

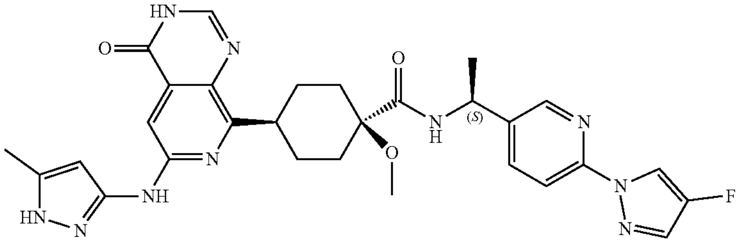

C23

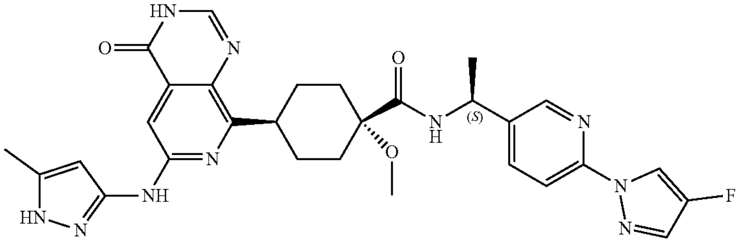

The synthetic route and experimental process were as follows:
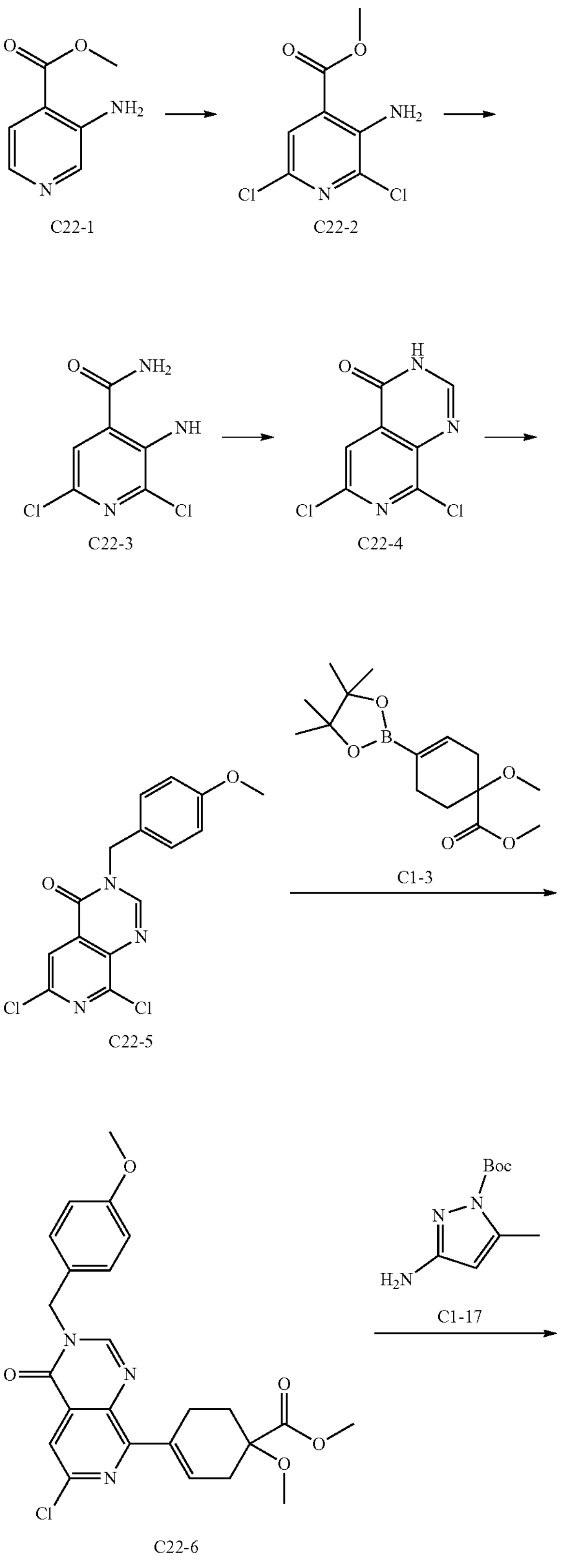
C22-1
C22-2
C22-3
C22-4
C22-5
C22-6
-continued
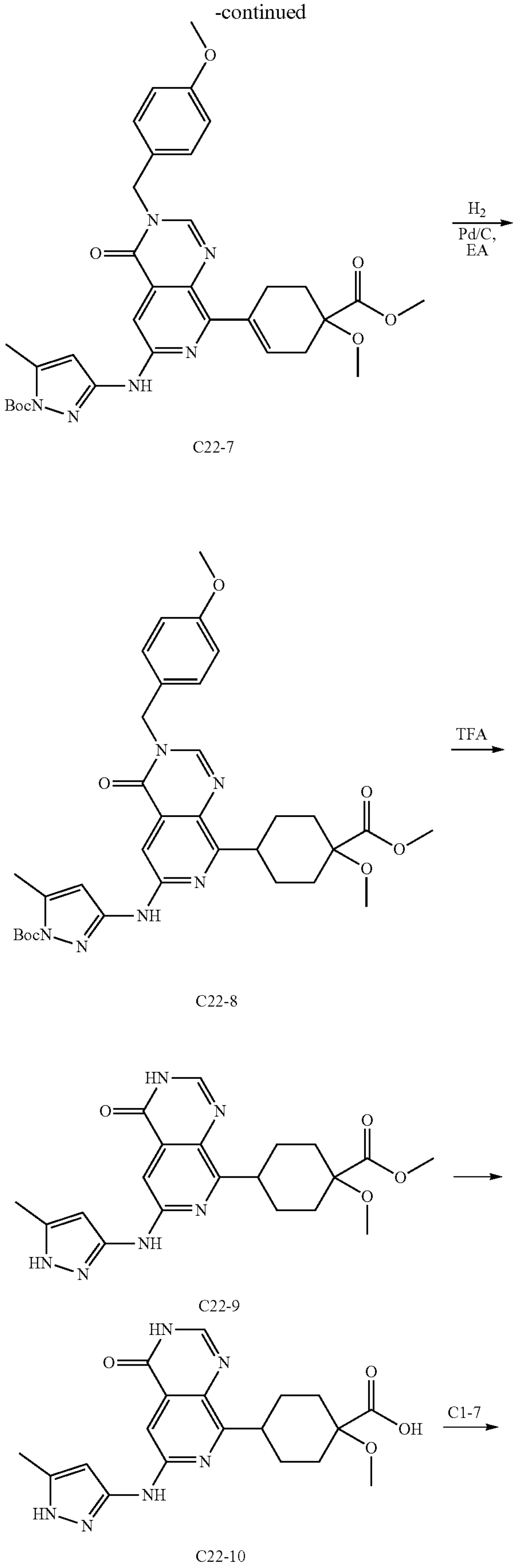
C22-7
C22-8
C22-9
C22-10

-continued

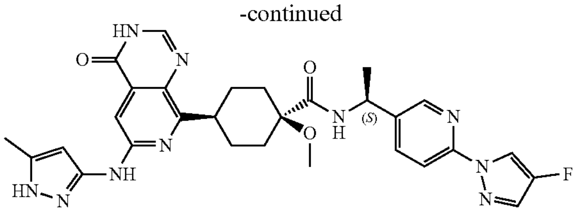

C22 and

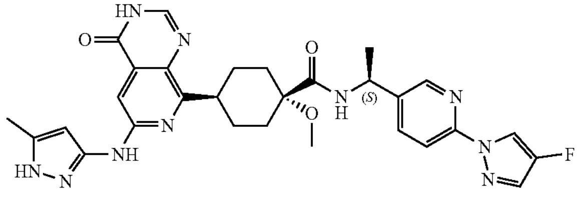

C23

1. Synthesis of C22-2

C22-1 (5.0 g, 30.1 mmol), NCS (9.3 g, 70.4 mmol) and DMF (100 mL) were added into a 250 mL single-neck flask to react at 25° C. for 15 h, then poured into water, extracted with ethyl acetate for three times. Organic phases were combined, dried, concentrated, and purified by column chromatography (petroleum ether: ethyl acetate=10:1) to obtain 7.12 g of compound C22-2 in a yield of 986, [M+H]: 221.1

Nuclear magnetic analysis data of compound C22-2: 1HNMR: (CDCl3, 400 Hz) δ7.65 (s, 1H), 6.17 (s, 1H), 3.93 (s, 3H).

2. Synthesis of C22-3

C22-2 (6.7 g, 30.1 mmol), ammonia-water (wt %: 20) (50 mL) and EtOH (30 mL) were added into a 100 mL small autoclave to react at 80° C. for e ah, cooled to room temperature, evaporated, saturated brine was added, extracted with ethyl acetate for three times. Organic phases were combined, dried, concentrated, and purified by column chromatography (PE: ethyl acetate=5:1) to obtain 4.25 g of compound C22-3 in a yield of 68%, [M+H]: 206.1

Nuclear magnetic analysis data of compound C22-3: 1HNMR: (MeOD, 400 Hz) δ7.52 (s, 1H)

3. Synthesis of C22-4

C22-3 (3.8 g, 18.5 mmol) and triethyl orthoformate (80 mL) were added into a 250 mL small autoclave to react at 160° C. for 7 h, then it was cooled to room temperature, evaporated, saturated brine was added, extracted with ethyl acetate for three times. Organic phases were combined, slurried by MTBE to obtain 2.5 g of compound C22-4 in a yield of 64%, [M+H]: 215.9

Nuclear magnetic analysis data of compound C22-4: 1HNMR: (DMSO-d6, 400 Hz) δ 8.25 (s, 1H), 7.92 (s, 1H)

4. Synthesis of C22-5

C22-4 (300 mg, 1.40 mmol) and DMA (1 mL) were added into a 50 mL single-neck flask, and replaced with nitrogen. Then sodium hydride (2.80 mmol) were added at 0° C. and replaced with nitrogen again. PMBCl (1.68 mmol) was added dropwise to react at 25° C. for 12 h, TLC detection showed the reaction was completed, the reaction solution was poured into water, extracted with ethyl acetate for three times. Organic phases were combined, dried, concentrated and purified by column chromatography (petroleum ether: ethyl acetate=10:1) to obtain 347 mg of compound C22-5 in a yield of 75%, [M+H]: 336.0

Nuclear magnetic analysis data of compound C22-5: 1HNMR: (CDCl3, 400 Hz) δ8.23 (s, 1H), 8.06 (s, 1H), 7.29 (d, J=8.8 Hz, 2H), 6.89 (d, J=8.4 Hz, 2H), 5.12 (s, 2H), 3.79 (s, 3H).

5. Synthesis of C22-6

C22-5 (347 mg, 1.04 mmol), 1,4-dioxane/$H_2O$ (1 mL/0.5 mL) were added into a 50 mL single-neck flask, then C1-3 (1.25 mmol), $K_2CO_3$ (2.08 mmol) and $Pd(PPh_3)_4$ (0.052 mmol) were added to react at 100° C. for 12 h. The reaction was monitored by TLC until it was completed, the reaction solution was concentrated, water (5 mL) was added, extracted with ethyl acetate for three times. Organic phases were combined, dried, concentrated and purified by column chromatography (petroleum ether: ethyl acetate=5:1) to obtain 366 mg of compound C22-6 in a yield of 75%, [M+H]: 470.0.

Nuclear magnetic analysis data of compound C22-6: 1HNMR: (CDCl3, 400 Hz) δ8.08 (s, 1H), 7.97 (s, 1H), 7.30 (d, J=8.8 Hz, 2H), 6.88 (d, J=8.8 Hz, 2H), 6.85 (t, J=2.4 Hz, 1H), 5.11 (s, 2H), 3.79 (s, 6H), 3.32 (s, 3H), 2.86 (d, J=2.0 Hz, 2H), 2.86-2.79 (m, 2H), 2.71-2.57 (m, 2H).

6. Synthesis of C22-7

C22-6 (1.01 g, 2.15 mmol) and 1,4-dioxane (10 mL) were added into a 50 mL single-neck flask, and C1-17 (2.58 mmol), AcOK (4.30 mmol), $Pd_2(dba)_3$ (0.11 mmol), t-Bux-phos (0.11 mmol) were added to react at 90° C. for 12 h under nitrogen protection. The reaction was monitored by TLC until it was completed, then the reaction solution was concentrated, water (5 mL) was added, extracted with ethyl acetate for three times. The organic phases were combined, dried, concentrated and purified by column chromatography (petroleum ether: ethyl acetate=5:1) to obtain 761 mg of compound C22-7 in a yield of 56%, [M+H]: 631.3.

Nuclear magnetic analysis data of compound C22-7: 1HNMR: (CDCl3, 400 Hz) δ7.89 (s, 1H), 7.77 (s, 1H), 7.31 (d, J=4.0 Hz, 2H), 7.28 (s, 1H), 6.86 (d, J=8.8 Hz, 2H), 6.72 (s, 1H), 6.41 (s, 1H), 5.09 (s, 2H), 3.80 (s, 6H), 3.34 (s, 3H), 2.86 (d, J=2.0 Hz, 2H), 2.81-2.60 (m, 2H), 2.54 (s, 3H), 2.44-2.14 (m, 2H), 1.67 (s, 9H).

7. Synthesis of C22-8

C22-7 (751 mg, 1.19 mmol) and ethyl acetate (10 mL) were added into a 50 mL single-neck flask, and Pd/C (0.12 mmol) was added under the protection of nitrogen, replaced with nitrogen again and reacted at room temperature for 12 h under the condition of hydrogen. The reaction was monitored by TLC until it was completed, then the reaction solution was filtered. Organic phases were combined, dried and concentrated to obtain 638 mg of compound C22-8 in a yield of 85%, [M+H]: 533.3.

8. Synthesis of C22-9

C22-8 (217 mg, 0.34 mmol) and trifluoroacetic acid (5 mL) were added into a 50 mL single-neck flask, and reacted at 90° C. for 18 h. The reaction was monitored by TLC until it was completed, and the reaction solution was concentrated to obtain 143 mg of compound C22-9 in a yield of 100%, [M+H]: 413.1.

9. Synthesis of C22-10

C22-9 (139 mg, 0.34 mmol), $LiOH{\cdot}H_2O$ (1.3 mmol) and $MeOH/H_2O$ (2 mL/0.4 mL) were added into a 25 mL single-neck flask, and reacted at 60° C. for 18 h. LC-MS showed that the reaction was completed, and the reaction solution was concentrated to obtain 229 mg of crude product [M+H]: 399.1.

10. Synthesis of C22 and C23

C22-10 (320 mg, 0.80 mmol), C1-7 (0.88 mmol), DMF (2 mL), triethylamine (1.60 mmol) and PyBOP (1.20 mmol) were added into a 25 mL single-neck flask to react at room temperature for 18 h. LC-MS showed that the reaction was completed. The reaction solution was poured into 10 mL water, and extracted with ethyl acetate for three times, washed with saturated brine, dried over anhydrous sodium sulfate, concentrated to obtain crude product which was prepared and separated to obtain 15 mg of compound C22, [M+H]: 587.3 and 8 mg of compound C23, [M+H]: 587.3.

Example 14

The compound synthesized in the present invention:

C24

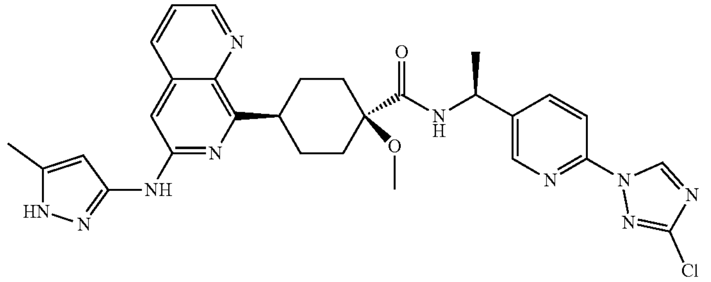

C25

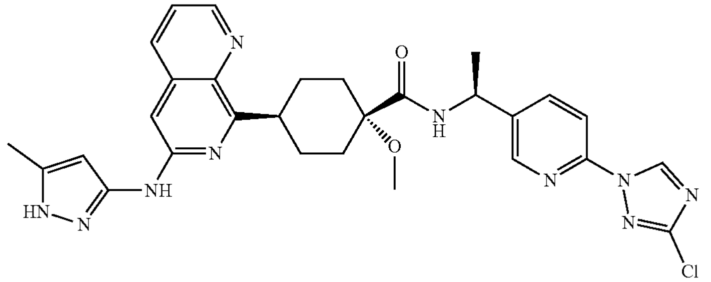

The synthetic route and experimental process were as follows:

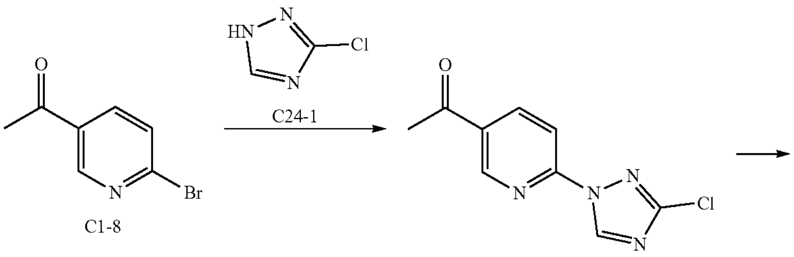

C1-8

C24-2

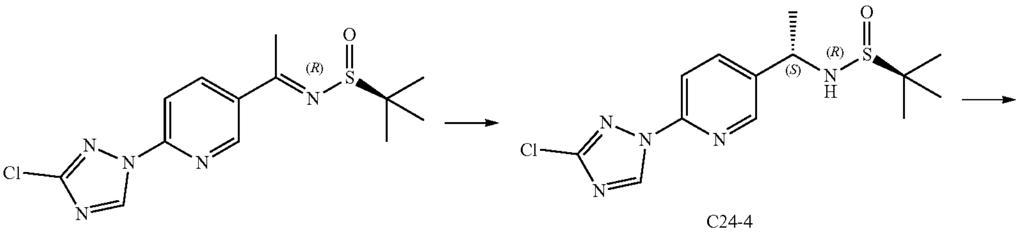

C24-3

C24-4

-continued

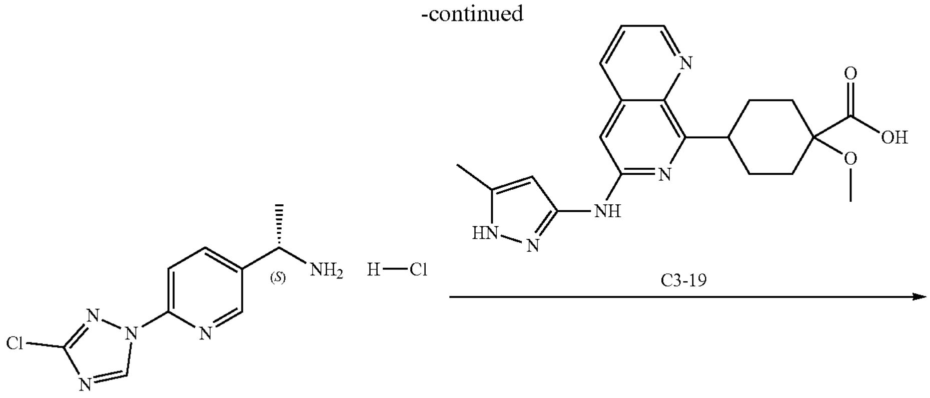

C24-5

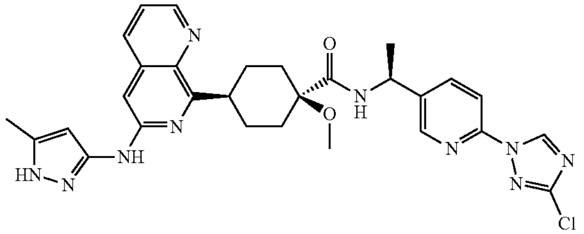

C24 and

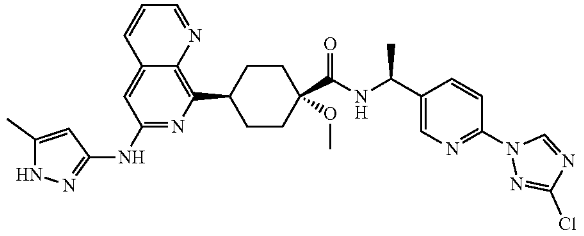

C25

1. Synthesis of C24-2

Compound C1-8 (1.0 g, 5.03 mmol) and compound C24-1 (0.62 g, 6.03 mmol) were dissolved in DMF (10 mL), then potassium carbonate (1.6 g, 11.57 mmol) was added, and the temperature was raised to 120° C. and stirred overnight. After the reaction was completed, the reaction solution was cooled to room temperature, the solvent DMF was removed by concentration under reduced pressure, and then diluted with ethyl acetate. Organic phase was washed with saturated brine, dried over anhydrous sodium sulfate, filtered, concentrated and purified by column chromatography to obtain 0.5 g of compound C24-2.

Nuclear magnetic analysis data of compound C24-2: 1H NMR (400 MHz, DMSO-d6) δ 9.57 (s, 1H), 9.09 (s, 1H), 8.57-8.55 (t, 1H), 7.97-7.95 (d, 1H, J=8.58 Hz), 2.68 (s, 3H).

2. Synthesis of C24-3

Compound C24-2 (397 mg, 1.79 mmol) and R-(+)-tert-butyl sulfinamide (260 mg, 2.15 mmol) were dissolved in dry tetrahydrofuran (20 mL), then tetraethyl titanate (898 mg, 3.94 mmol) was added, raised to 70° C. and stirred overnight under the protection of nitrogen. Cooled to room temperature after reaction was completed, 1 mL water was added, filtered under reduced pressure, and the filtrate was extracted with ethyl acetate. The organic phases were combined and washed with saturated brine, dried over anhydrous sodium sulfate, filtered, concentrated and purified by column chromatography to obtain 429 mg of compound C24-3.

Nuclear magnetic analysis data of compound C24-3: $^{1}H$ NMR (400 MHz, DMSO-$d_6$) δ 9.54 (s, 1H), 9.02-9.01 (d, 1H, J=1.93 Hz), 8.55-8.52 (dd, 1H, J=8.60 Hz, 2.68 Hz), 7.94-7.92 (d, 1H, J=8.35 Hz), 2.80 (s, 3H), 1.25 (s, 9H).

3. Synthesis of C24-4

Compound C24-3 (429 mg, 1.32 mmol) was dissolved in dry tetrahydrofuran (5 mL), cooled to −78° C., and 1M tri-sec-butyl lithium borohydride in tetrahydrofuran (3.96 ml, 3.96 mmol) was added dropwise under the protection of nitrogen, and stirred at −78° C. for 1 h. The reaction was monitored by TLC until it was completed, methanol was added dropwise to quench, raised to room temperature, and diluted with ethyl acetate. Organic phase was washed with saturated brine, dried over anhydrous sodium sulfate, filtered, concentrated and purified by column chromatography to obtain 362 mg of compound C24-4.

Nuclear magnetic analysis data of compound C24-4: $^{1}H$ NMR (400 MHz, DMSO-$d_6$) δ 9.50 (s, 1H), 8.59-8.58 (d, 1H, J=1.93 Hz), 8.13-8.11 (dd, 1H, J=8.65 Hz, 2.34 Hz), 7.88-7.85 (d, 1H, J=8.65 Hz), 5.69-5.68 (d, 1H, J=5.67 Hz), 4.68-4.61 (m, 1H), 1.58-1.57 (d, 3H, J=6.80 Hz), 1.17 (s, 9H).

4. Synthesis of C24-5

Compound C24-4 (362 mg, 1.11 mmol) was dissolved in a mixed solution of dioxane (1.4 mL) and anhydrous methanol (1.4 mL), then 4M hydrogen chloride in dioxane solution (2.8 ml) was added, and stirred at room temperature for 2 h. Then methyl tert-butyl ether was added, filtered and dried to obtain 258 mg of compound C24-5.

Nuclear magnetic analysis data of compound C24-5: $^1$H NMR (400 MHz, DMSO-$d_6$) δ 9.50 (s, 1H), 8.73-8.71 (m, 4H), 8.29-8.26 (dd, 1H, J=8.55 Hz, 2.39 Hz), 7.93-7.91 (d, 1H, J=8.30 Hz), 4.61 (br, 1H), 1.60-1.58 (d, 3H, J=7.14 Hz).

5. Synthesis of C24 and C25

Compound C24-5 (40 mg, 0.16 mmol) and compound C3-19 (60 mg, 0.16 mmol) were dissolved in DMF (1.2 ml), then DIPEA (160 mg, 1.24 mmol) was added and stirred at room temperature for 5 min, then HATU (88 mg, 0.23 mmol) was added, and stirred at room temperature for 1 h. The reaction solution was diluted with ethyl acetate. Organic phase was washed with saturated brine, dried over anhydrous sodium sulfate, concentrated, and purified by Prep-HPLC to obtain 31 mg of compound C24 and 27 mg of compound C25.

Nuclear magnetic analysis data of compound C24: $^1$H NMR (400 MHz, $CDCl_3$) δ 9.05 (s, 1H), 8.67-8.66 (d, 1H, J=3.99 Hz, 1.54 Hz), 8.44-8.43 (d, 1H, J=1.94 Hz), 7.91-7.89 (dd, 1H, J=8.45 Hz, 1.41 Hz), 7.86-7.79 (m, 2H), 7.38-7.35 (m, 2H), 7.06 (s, 1H), 6.93-6.91 (d, 1H, J=7.75 Hz), 5.88 (s, 1H), 5.22-5.18 (m, 1H), 4.24-4.18 (m, 1H), 3.31 (s, 3H), 2.32 (s, 3H), 2.18-2.10 (m, 2H), 2.07-1.94 (m, 5H), 1.91-1.86 (m, 2H), 1.59-1.57 (d, 3H, J=7.04 Hz).

Nuclear magnetic analysis data of compound C25: $^1$H NMR (400 MHz, $CDCl_3$) δ 8.99 (s, 1H), 8.59-8.58 (dd, 1H, J=3.88 Hz, 1.55 Hz), 8.43-8.42 (d, 1H, J=2.07 Hz), 7.85-7.79 (m, 1H), 7.74-7.72 (m, 1H), 7.30-7.27 (m, 3H), 6.75-6.73 (d, 1H, J=7.49 Hz), 5.79 (s, 1H), 5.19-5.14 (m, 1H), 4.19-4.14 (m, 1H), 3.21 (s, 3H), 2.34-2.30 (m, 1H), 2.24 (s, 1H), 2.22-2.11 (m, 3H), 1.98-1.92 (m, 3H), 1.78-1.71 (m, 2H), 1.53-1.51 (d, 3H, J=7.23 Hz).

Example 15

The compound synthesized in the present invention:

C26

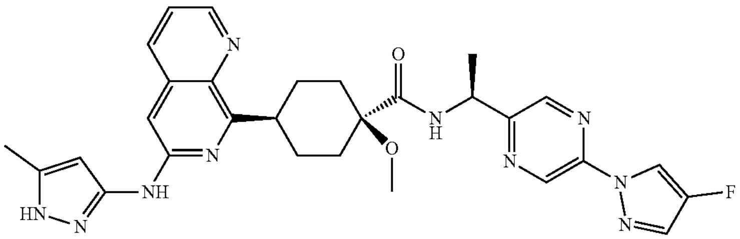

The synthetic route and experimental process were as follows:

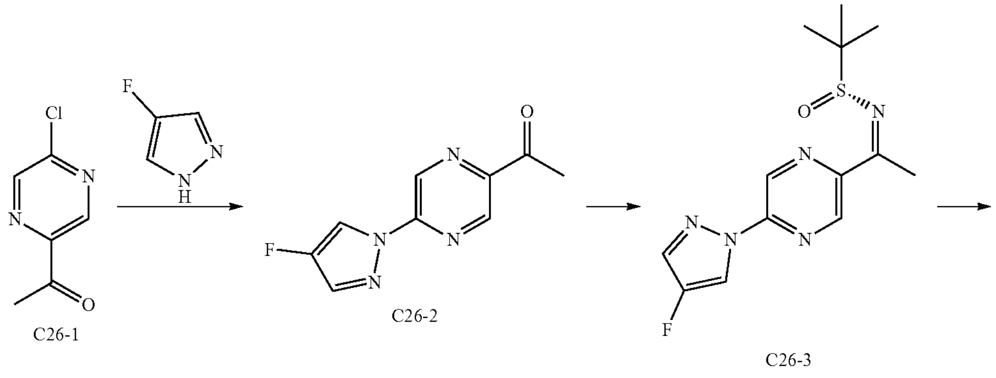

C26-1

C26-2

C26-3

-continued

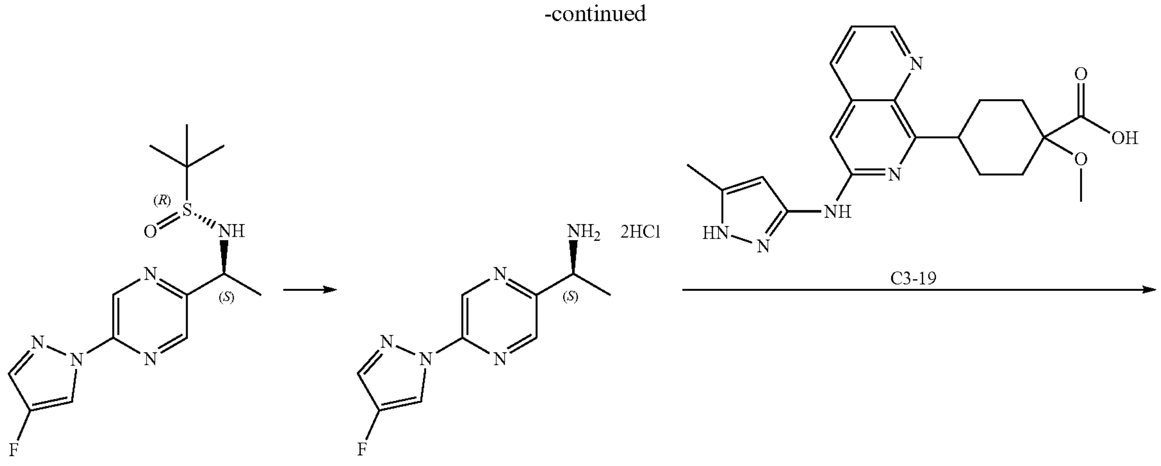

C26-4 C26-5

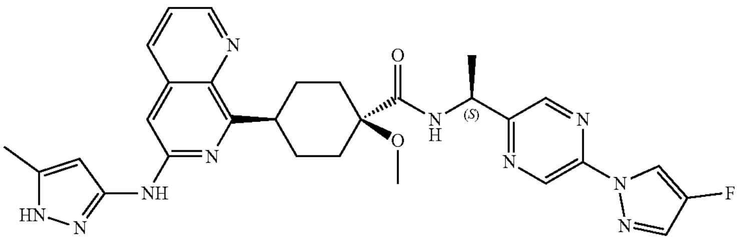

C26

1. Synthesis of C26-2

C26-1 (1.57 g, 10 mmol), 4-fluoro-1H pyrazole (860 mg, 10 mmol), N, N-dimethylformamide (10 mL) and potassium carbonate (2.76 g, 20 mmol) were added into a 50 mL single-neck flask to react at 100° C. for 8 h. LC-MS showed that the reaction was completed, the reaction solution was poured into water (200 mL) under stirring, and solid was precipitated, then filtered. The filter cake was washed with water, and dried to obtain 1.08 g solid. [M+1]: 207.03.

2. Synthesis of C26-3

C26-2 (870 mg, 4.2 mmol), R-tert-butyl sulfinamide (560 mg, 4.63 mmol), tetraethyl titanate (1.92 g, 8.4 mmol), and dry tetrahydrofuran (10 mL) were successively added into a 100 mL single-neck flask to react at 75° C. overnight. The reaction solution was cooled, diluted with water (30 mL), suction-filtered. The filtrate was extracted with ethyl acetate (20 mL) for three times. Organic phase was dried over anhydrous sodium sulfate, evaporated under reduced pressure, and purified by column chromatography to obtain 500 mg of product.

3. Synthesis of C26-4

C26-3 (100 mg, 0.32 mmol) and dry tetrahydrofuran (2 mL) were successively added into a 50 mL single-neck flask, cooled to −78° C., then tri-sec-butyl lithium borohydride (0.7 mL, 0.7 mmol, 1.0M) was added dropwise and reacted at −78° C. for 1 h. The reaction was quenched with methanol (1 mL) at −60° C., diluted with water (5 mL), extracted with ethyl acetate (5 mL) for three times. Organic phase was dried, evaporated under reduced pressure and purified by column chromatography to obtain 113 mg of product.

Nuclear magnetic analysis data of compound C26-4: 1H NMR (400 MHz, CDCl3) δ 9.23 (d, J=1.4 Hz, 1H), 8.36 (d, J=1.5 Hz, 1H), 8.33 (d, J=4.6 Hz, 1H), 7.66 (d, J=4.3 Hz, 1H), 4.77 (p, J=6.6 Hz, 1H), 3.74 (d, J=5.9 Hz, 1H), 1.67 (d, J=6.8 Hz, 3H), 1.22 (s, 9H).

4. Synthesis of C26-5

C26-4 (100 mg, 0.32 mmol), dichloromethane (3 mL), methanol (0.5 mL), HCl/dioxane (4M, 1.5 mL) were added into a 50 mL single-neck flask to react at room temperature for 3 h. LC-MS detection showed the reaction was completed, diluted with dichloromethane, filtered, the filter cake was washed with ethyl acetate. The filter cake was dried to obtain 67 mg of product. [M+1]: 208.06.

5. Synthesis of C26

C26-5 (47 mg, 0.17 mmol), C3-19 (65 mg, 0.17 mmol), N, N-dimethylformamide (1 mL), and N,N-diisopropylethylamine (175 mg, 1.36 mmol) were added into a 25 mL single-neck flask, stirred for 5 min at room temperature, and HATU (97 mg, 0.26 mmol) was added to react at room temperature for 30 min. LC-MS showed that the reaction was completed. The reaction solution was poured into 10 mL water, and prepared and separated to obtain C26 (37.6 mg, purity: 91%), [M+1]: 571.3.

Nuclear magnetic analysis data of compound C26: 1H NMR (400 MHz, DMSO-d6) δ 11.76 (d, J=5.3 Hz, 1H), 9.14 (dd, J=6.8, 3.1 Hz, 2H), 8.79-8.68 (m, 1H), 8.63 (tt, J=4.2, 2.0 Hz, 1H), 8.54 (d, J=5.3 Hz, 1H), 8.45 (t, J=6.4 Hz, 1H), 8.12-7.97 (m, 2H), 7.73-7.43 (m, 2H), 6.08-5.93 (m, 1H), 5.16 (q, J=7.1 Hz, 1H), 3.27-3.16 (m, 3H), 2.28-2.17 (m, 3H), 2.12-1.64 (m, 9H), 1.51 (d, J=6.8 Hz, 3H).

Example 16
The compound synthesized in the present invention:
C27
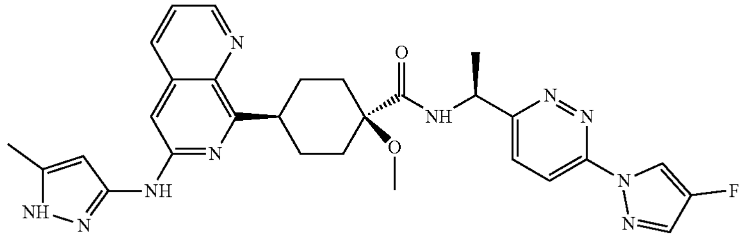
C28
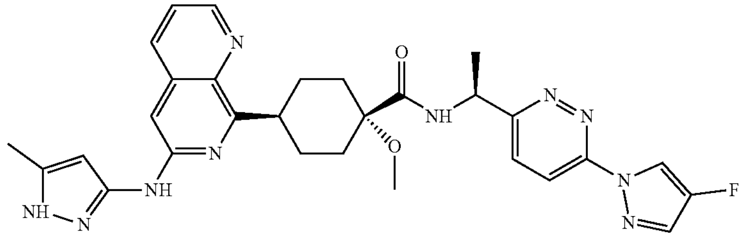
The synthetic route and experimental process were as follows:
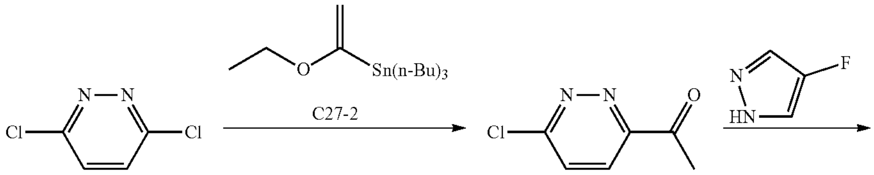
C27-1 C27-3
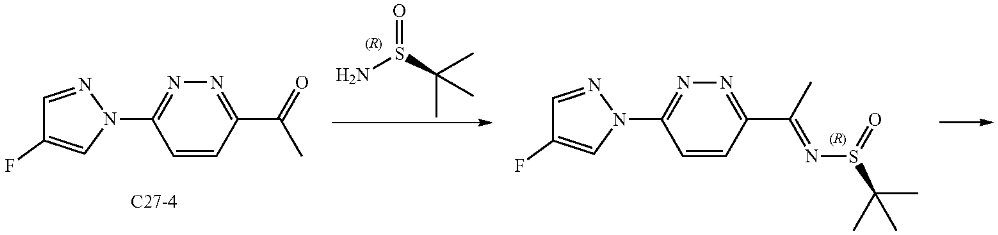
C27-4 C27-5
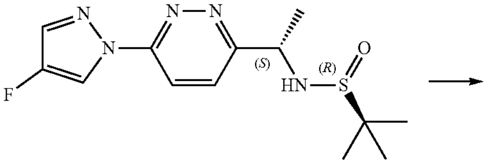
C27-6

-continued

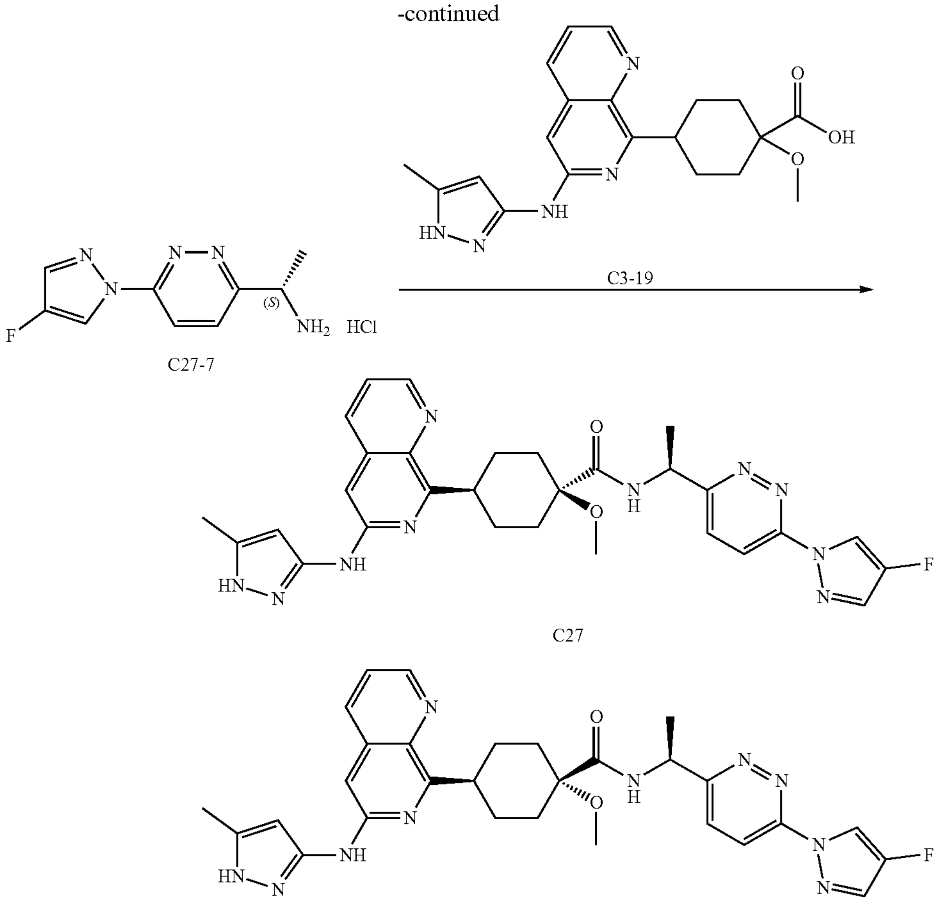

C27-7

C27

C28

1. Synthesis of C27-3

Compound C27-1 (1.49 g, 10 mmol) and $Pd(PPh_3)_4$ (115 mg, 0.1 mmol) were dissolved in toluene (50 mL), then compound C27-2 (4.33 g, 12 mmol) was added, and the temperature was raised to 120° C. and stirred for 5 h. Cooled to room temperature after the reaction was completed, 1M HCl (20 mL) was added, raised to 60° C. and stirred for 1 h, concentrated, water was added, and diluted with ethyl acetate. Organic phase was washed with saturated brine, dried over anhydrous sodium sulfate, filtered, concentrated and purified by column chromatography to obtain 1.2 g of compound C27-3.

Nuclear magnetic analysis data of compound C27-3: 1H NMR (400 MHz, CDCl3) δ 8.12-8.10 (d, 1H, J=9.04 Hz), 7.69-7.67 (d, 1H, J=9.04 Hz), 2.88 (s, J=3H).

2. Synthesis of C27-4

Compound C27-3 (500 mg, 3.2 mmol) and 4-fluoro-1H pyrazole (303 mg, 3.5 mmol) were dissolved in DMF (10 mL), then potassium carbonate (1020 mg, 7.4 mmol) was added, and the temperature was raised to 100° C. and stirred overnight. Cooled to room temperature after the reaction was completed, concentrated, extracted with ethyl acetate after adding water. The organic phases were combined and washed with saturated brine, dried over anhydrous sodium sulfate, filtered, concentrated and purified by column chromatography to obtain 440 mg of compound C27-4.

Nuclear magnetic analysis data of compound C27-4: 1H NMR (400 MHz, DMSO-d6) δ 9.08-9.07 (dd, 1H, J=4.60 Hz, 0.62 Hz), 8.36-8.34 (d, 1H, J=9.04 Hz), 8.31-8.28 (d, 1H, J=9.04 Hz), 8.20-8.18 (dd, 1H, J=4.10 Hz, 0.75 Hz), 2.79 (s, 3H).

3. Synthesis of C27-5

Compound C27-4 (350 mg, 1.7 mmol) and R-tert-butyl sulfinamide (247 mg, 2.0 mmol) were dissolved in dry tetrahydrofuran (40 mL), then tetraethyl titanate (775 mg, 3.4 mmol) was added under the protection of nitrogen, and raised to 80° C. and stirred overnight. 1 mL water was added, filtered, the filter cake was washed with ethyl acetate. The filtrate was concentrated and purified by column chromatography to obtain 342 mg of compound C27-5.

Nuclear magnetic analysis data of compound C27-5: 1H NMR (400 MHz, CDCl3) δ 8.66-8.65 (d, 1H J=4.53 Hz), 8.35-8.33 (d, 1H, J=9.04 Hz), 8.24-8.22 (d, 1H, J=9.04 Hz), 7.73-7.72 (d, 1H, J=4.21 Hz), 3.02 (s, 3H), 1.35 (s, 9H).

4. Synthesis of C27-6

Compound C27-5 (292 mg, 0.94 mmol) was dissolved in dry tetrahydrofuran (3 mL), cooled to −78° C., then tri-sec-butyl lithium borohydride (2.83 mL, 2.83 mmol, 2 1.0M) was added dropwise and reacted at −78° C. for 1 h. The reaction was quenched with methanol (3 mL) at −60° C., diluted with water, extracted with ethyl acetate. Organic phase was dried, evaporated under reduced pressure and purified by column chromatography to obtain 200 mg of product.

Nuclear magnetic analysis data of compound C27-6: 1H NMR (400 MHz, CDCl3) δ 8.55-8.54 (dd, 1H J=4.61 Hz, 0.55 Hz), 8.12-8.09 (d, 1H, J=9.04 Hz), 7.62-7.60 (m, 2H), 4.88-4.85 (m, 1H), 1.66-1.64 (d, 3H, J=6.95 Hz), 1.16 (s, 9H).

5. Synthesis of C27-7

Compound C27-6 (200 mg, 0.71 mmol) was dissolved in dioxane (1.8 mL) and methanol (1.8 mL), and 4M hydrochloric acid/dioxane (1.8 mL, 7.2 mmol) was added to react for 3 h at room temperature. LC-MS detection showed the reaction was completed, diluted with ethyl acetate and filtered. The filter cake was washed with ethyl acetate and dried to obtain 47 mg of product.

Nuclear magnetic analysis data of compound C27-7: 1H NMR (400 MHz, DMSO-d6) δ 8.98-8.97 (dd, 1H, J=4.54 Hz, 0.62 Hz), 8.81 (br, 3H), 8.34-8.32 (d, 1H, J=9.25 Hz), 8.14-8.10 (m, 2H), 4.83-4.77 (m, 1H), 1.62-1.60 (d, 3H, J=7.66 Hz).

6. Synthesis of C27 and C28

Compound C27-7 (30 mg, 0.12 mmol) and compound C3-19 (48 mg, 0.12 mmol) were dissolved in 1 mL DMF, then diisopropylethylamine (0.3 mL, 0.96 mmol) was added and stirred at room temperature for 5 min, then HATU (71 mg, 0.18 mmol) was added, and stirred at room temperature for 1 h. The reaction solution was diluted with ethyl acetate. Organic phase was washed with saturated brine, dried over anhydrous sodium sulfate, concentrated, and purified by Prep-HPLC to obtain 20 mg of compound C27 and 10 mg of compound C28.

Nuclear magnetic analysis data of compound C27: 1H NMR (400 MHz, CDCl3) δ 8.58-8.56 (dd, 1H, J=4.06 Hz, 1.72 Hz), 8.53-8.52 (d, 1H, J=4.84 Hz), 8.09-8.07 (d, 1H, J=9.37 Hz), 7.86-7.84 (d, 1H, J=8.12 Hz), 7.81-7.88 (dd, 1H, J=8.74 Hz, 1.56 Hz), 7.61-7.57 (m, 2H), 7.33 (br, 1H), 7.28-7.25 (m, 1H), 7.22 (s, 1H), 5.89 (br, 1H), 5.34-5.28 (m, 1H), 4.13-4.09 (m, 1H), 3.27 (s, 3H), 2.27 (s, 3H), 2.15-1.76 (m, 8H), 1.62-1.59 (d, 3H, J=6.87 Hz).

Nuclear magnetic analysis data of compound C28: 1H NMR (400 MHz, CDCl3) δ 8.59-8.58 (dd, 1H, J=4.06 Hz, 1.72 Hz), 8.52-8.50 (dd, 1H, J=4.53 Hz, 0.70 Hz), 8.08-8.06 (d, 1H, J=9.07 Hz), 7.83-7.80 (dd, 1H, J=8.27 Hz, 1.56 Hz), 7.61-7.58 (d, 1H, J=9.21 Hz), 7.58-7.57 (d, 1H, J=4.53 Hz), 7.48 (br, 1H), 7.44-7.42 (d, 1H, J=8.43 Hz) 7.29-7.26 (m, 1H), 7.23 (s, 1H), 5.83 (br, 1H), 5.38-5.31 (m, 1H), 4.22-4.15 (m, 1H), 3.22 (s, 3H), 2.27 (s, 3H), 2.35-1.70 (m, 8H), 1.61-1.59 (d, 3H, J=7.49 Hz).

Example 17

The compound synthesized in the present invention:

C29

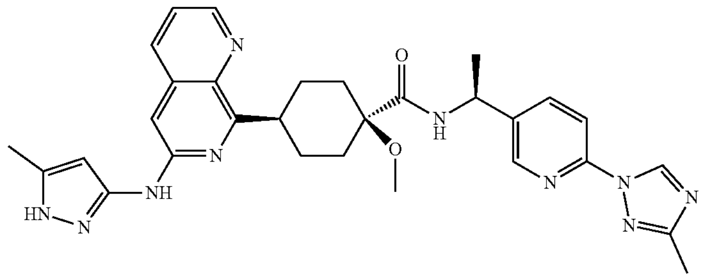

C30

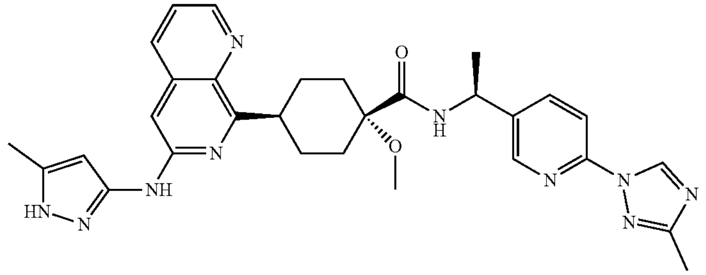

The synthetic route and experimental process were as follows:

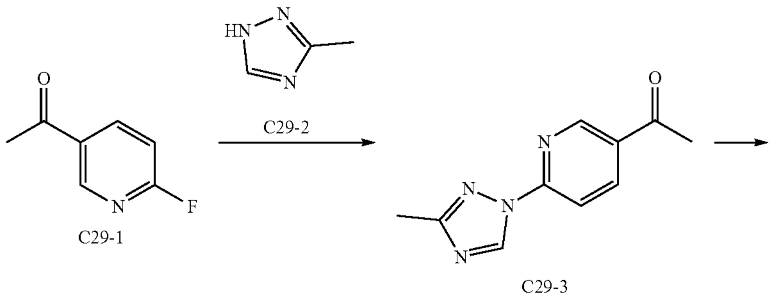

C29-2

C29-1

C29-3

-continued

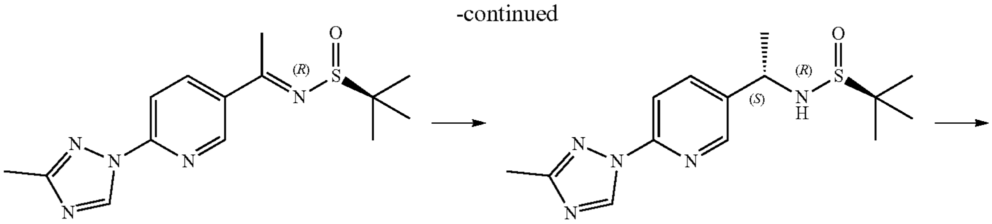

C29-4 C29-5

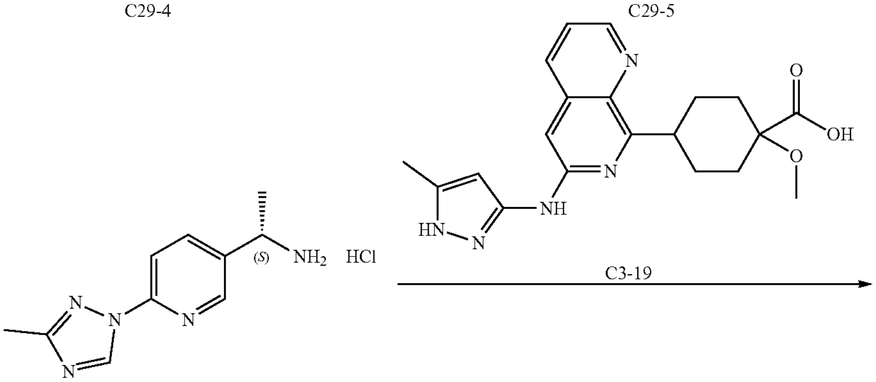

C29-6

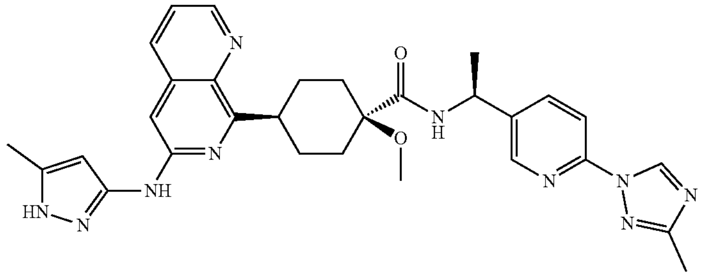

C29 and

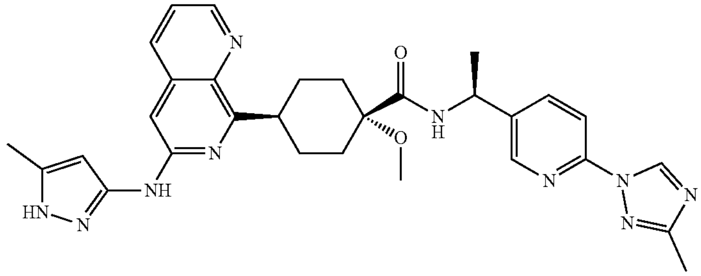

C30

1. Synthesis of C29-3

Compound C29-1 (500 mg, 3.6 mmol) and compound C29-2 (420 mg, 5 mmol) were dissolved in DMF (10 mL), then potassium carbonate (1150 mg, 8.3 mmol) was added, and the temperature was raised to 100° C. and stirred overnight. Cooled to room temperature after reaction was completed, concentrated, extracted with ethyl acetate after adding water. The organic phases were combined and washed with saturated bine, dried over anhydrous sodium sulfate, filtered, concentrated and purified by column chromatography to obtain 565 mg of compound C29-3.

Nuclear magnetic analysis data of compound C29-3: 1H NMR (400 MHz, DMSO-d6) δ 9.34 (s, 1H), 9.06-9.05 (d, 1H, J=2.03 Hz), 8.53-8.0 (dd, 1H, J=8.59 Hz, 2.34 Hz), 7.93-7.91 (dd, 1H, J=8.62 Hz, 0.9H z), 2.66 (s, 3H), 2.41 (s, 3H).

2. Synthesis of C29-4

Compound C29-3 (565 mg, 2.8 mmol) and R-tert-butyl sulfinamide (406 mg, 3.4 mmol) were dissolved in 50 mL dry tetrahydrofuran, then tetraethyl titanate (1275 mg, 5.6 mmol) was added under the protection of nitrogen, and raised to 80° C. and stirred overnight, 2 mL water was added, filtered, and the filter cake was washed with ethyl acetate. The filtrate was concentrated and purified by column chromatography to obtain 852 mg of compound C29-4.

Nuclear magnetic analysis data of compound C29-4: 1H NMR (400 MHz, CDCl3) δ 9.01 (s, 1H), 8.85-8.84 (d, 1H, J=2.03 Hz), 8.27-8.24 (dd, 1H, J=8.82 Hz, 2.67 Hz), 7.82-7.80 (d, 1H, J=4.21 Hz), 2.74 (s, 3H), 2.43 (s, 3H), 1.27 (s, 9H).

3. Synthesis of C29-5

Compound C29-4 (752 mg, 2.47 mmol) was dissolved in dry tetrahydrofuran (8 mL), cooled to −78° C., then tri-sec-butyl lithium borohydride (7.4 mL, 7.4 mmol, 1.0M) was added dropwise and reacted at −78° C. for 1 h. The reaction was quenched with methanol (8 mL) at −60° C., diluted with water, extracted with ethyl acetate. Organic phase was dried, evaporated under reduced pressure and purified by column chromatography to obtain 578 mg of product.

Nuclear magnetic analysis data of compound C29-5: 1H NMR (400 MHz, CDCl3) δ 8.96 (s, 1H), 8.33 (s, 1H), 7.79-7.72 (m, 2H), 4.62-4.58 (m, 1H), 2.42 (s, 3H), 1.53-1.51 (d, 3H, J=7.77 Hz), 1.14 (s, 9H).

4. Synthesis of C29-6

Compound C29-5 (200 mg, 0.65 mmol) was dissolved in DCM (1.6 mL) and methanol (0.5 mL), and 4M hydrochloric acid/dioxane (1.6 mL, 6.5 mmol) was added to react for 3 h at room temperature. LC-MS detection showed the reaction was completed, diluted with ethyl acetate and filtered. The filter cake was washed with ethyl acetate and dried to obtain 129 mg of product.

Nuclear magnetic analysis data of compound C29-6: 1H NMR (400 MHz, MeOD-d4) δ 10.48 (s, 1H), 8.73 (s, 1H), 8.36-8.33 (dd, 1H, J=8.58 Hz, 2.27 Hz), 8.06-8.04 (d, 1H, J=8.58 Hz), 4.72-4.68 (m, 1H), 2.63 (s, 3H), 1.71-1.69 (d, 3H, J=6.76 Hz).

5. Synthesis of C29 and C30

Compound C29-6 (100 mg, 0.42 mmol) and compound C3-19 (162 mg, 0.42 mmol) were dissolved in DMF (3 mL), then diisopropylethylamine (0.55 mL, 3.3 mmol) was added and stirred at room temperature for 5 min, then HATU (238.5 mg, 0.63 mmol) was added, and stirred at room temperature for 1 h. The reaction solution was diluted with ethyl acetate. Organic phase was washed with saturated brine, dried over anhydrous sodium sulfate, concentrated, and purified by Prep-HPLC to obtain 9 mg of compound C29 and 5 mg of compound C30.

Nuclear magnetic analysis data of compound C29: 1H NMR (400 MHz, CDCl3) δ 8.95 (s, 1H), 8.61-8.59 (dd, 1H, J=4.26 Hz, 1.72 Hz), 8.36 (br, 1H), 7.84-7.82 (dd, 1H, J=8.88 Hz, 1.86 Hz), 7.75-7.73 (m, 2H), 7.31-7.27 (m, 2H), 7.06 (br, 1H), 6.84-6.82 (d, 1H, J=8.52 Hz), 5.83 (br, 1H), 5.17-5.10 (m, 1H), 4.17-4.11 (m, 1H), 3.24 (s, 3H), 2.43 (s, 3H), 2.25 (s, 3H), 2.15-1.79 (m, 8H), 1.52-1.50 (d, 3H, J=7.46 Hz).

Nuclear magnetic analysis data of compound C30: 1H NMR (400 MHz, CDCl3) δ 8.95 (s, 1H), 8.58-8.57 (dd, 1H, J=4.26 Hz, 1.72 Hz), 8.40-8.39 (d, 1H, J=2.13 Hz), 7.83-7.70 (m, 3H), 7.37 (br, 1H), 7.29-7.26 (m, 2H), 6.74-6.72 (d, 1H, J=7.81 Hz), 5.80 (br, 1H), 5.22-5.14 (m, 1H), 4.20-4.13 (m, 1H), 3.20 (s, 3H), 2.41 (s, 3H), 2.33-2.25 (m, 2H), 2.23 (s, 3H), 2.16-2.13 (m, 2H), 1.95-1.90 (m, 2H), 1.78-1.70 (m, 2H), 1.52-1.50 (d, 3H, J=6.75 Hz).

Example 18

The compound synthesized in the present invention:

C31

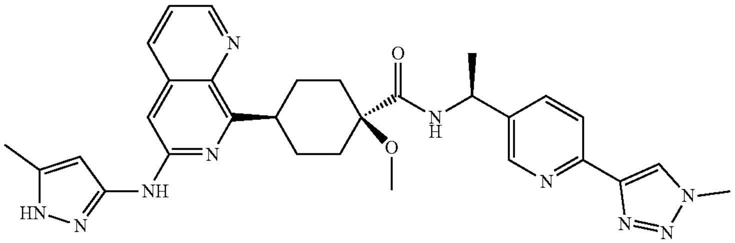

The synthetic route and experimental process were as follows:

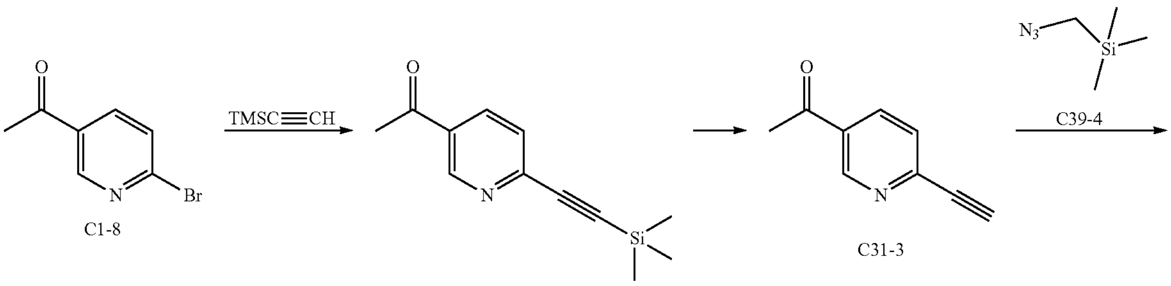

C1-8 C31-2 C31-3

-continued

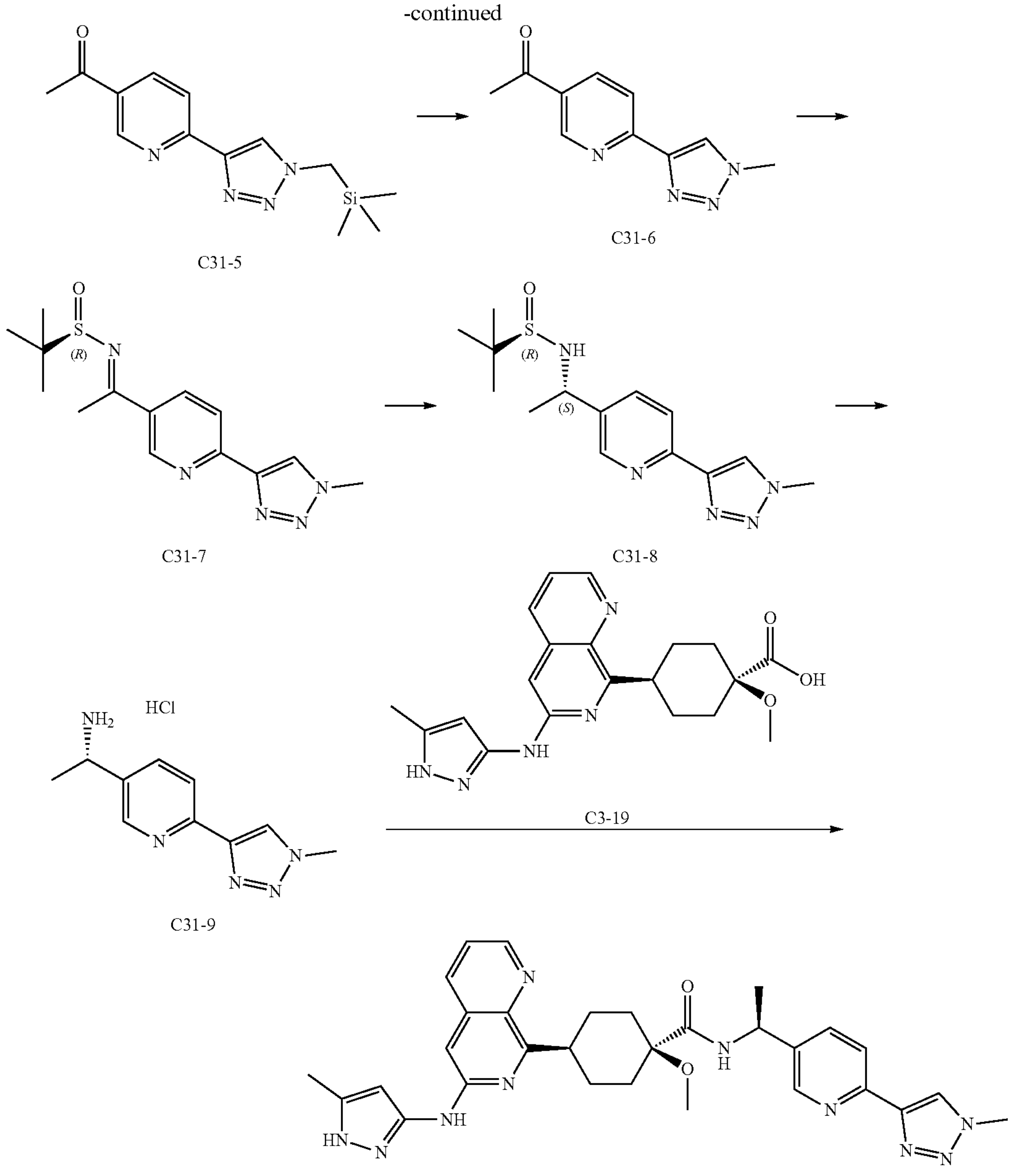

C31-5

C31-6

C31-7

C31-8

C31-9

C3-19

C31

1. Synthesis of C31-2

Compound C31-8 (2.0 g, 10 mmol) and trimethylsilylacetylene (1.7 mL, 12 mmol) were dissolved in dry THF (20 mL) and triethylamine (20 mL), then CuI (190 mg, 1 mmol) and palladium tetratriphenylphosphine (580 mg, 0.5 mmol) were successively added, and raised to 30° C. and stirred overnight. After the reaction was completed, the reaction solution was cooled to room temperature, concentrated under reduced pressure, and then diluted with ethyl acetate. Organic phase was washed with saturated brine, dried over anhydrous sodium sulfate, filtered, concentrated and purified by column chromatography to obtain 2.1 g of compound C31-2.

Nuclear magnetic analysis data of compound C31-2: $^1H$ NMR (400 MHz, DMSO-$d_6$) δ □9.10-9.09 (d, 1H, J=1.54 Hz), 8.19-8.17 (dd, 1H, J=8.29 Hz, 2.14 Hz), 7.56-7.53 (dd, 1H, J=8.12 Hz, 0.55 Hz), 2.63 (s, 3H), 0.28 (s, 9H).

2. Synthesis of C31-3

Compound C31-2 (1.0 g, 4.61 mmol) was dissolved in 20 mL anhydrous methanol, then anhydrous potassium carbonate (1.27 g, 9.21 mmol) was added, and the reaction solution was stirred at room temperature for 1 h. After the reaction was completed, diluted with ethyl acetate, and then potassium carbonate was filtered out. The filtrate was washed with saturated brine, dried with anhydrous sodium sulfate, concentrated under reduced pressure, and purified by column chromatography to obtain 605 mg of compound C31-3.

Nuclear magnetic analysis data of compound C31-3: $^1H$ NMR (400 MHz, DMSO-$d_6$) δ □9.13 (s, 1H), 8.23-8.20 (dd, 1H, J=7.79 Hz, 1.56 Hz), 7.60-7.58 (d, 1H, J=8.18 Hz), 3.34 (s, 1H), 2.65 (s, 3H).

3. Synthesis of C31-5

CuI (63 mg, 0.33 mmol) was suspended in a mixture of DMF (2 mL) and diisopropylethylamine (3 mL), then compound C31-3 (237 mg, 1.64 mmol) and compound C31-4 (422 mg, 3.27 mmol) were successively added. The reaction solution was stirred overnight at room temperature. After the reaction was completed, diluted with ethyl acetate. Organic phase was washed with saturated brine, dried over anhydrous sodium sulfate, concentrated under reduced pressure, and purified by column chromatography to obtain 313 mg of compound C31-5.

Nuclear magnetic analysis data of compound C31-5: $^1$H NMR (400 MHz, DMSO-$d_6$) δ 9.11-9.10 (d, 1H, J=1.08 Hz), 8.31-8.25 (m, 2H), 8.08 (s, 1H), 3.99 (s, 2H), 2.64 (s, 3H), 0.18 (s, 9H).

4. Synthesis of C31-6

Compound C31-5 (625 mg, 2.28 mmol) was dissolved in tetrahydrofuran (150 ml), then 1M tetrabutylammonium fluoride in tetrahydrofuran (2.74 ml, 2.74 mmol) was added dropwise under ice water bath, and stirred for 1 h under ice water bath. After the reaction was completed, it was washed with saturated brine and extracted with ethyl acetate. The organic phases were combined and washed with saturated brine, dried over anhydrous sodium sulfate, concentrated under reduced pressure and purified by column chromatography to obtain 363 mg of compound C31-6.

Nuclear magnetic analysis data of compound C31-6: $^1$H NMR (400 MHz, DMSO-$d_6$) δ 9.13-9.12 (d, 1H, J=0.89 Hz), 8.33-8.27 (m, 2H), 8.21 (s, 1H), 4.20 (s, 2H), 2.66 (s, 3H).

5. Synthesis of C31-7

Compound C31-6 (490 mg, 2.43 mmol) and R-tert-butyl sulfinamide (309 mg, 3.64 mmol) were dissolved in dry tetrahydrofuran (20 mL), then tetraethyl titanate (2.22 g, 9.72 mmol) was added, and raised to 80° C. and stirred overnight under the protection of nitrogen. After the reaction was completed, it was cooled to room temperature, 2 mL water was added, and filtered under reduced pressure. The filtrate was extracted with ethyl acetate. The organic phases were combined and washed with saturated brine, dried over anhydrous sodium sulfate, filtered, concentrated and purified by column chromatography to obtain 575 mg of compound C31-7.

Nuclear magnetic analysis data of compound C31-7: $^1$H NMR (400 MHz, DMSO-$d_6$) δ 9.06 (s, 1H), 8.23-8.22 (d, 2H, J=1.47 Hz), 8.16 (s, 1H), 4.18 (s, 3H), 2.80 (s, 3H), 1.33 (s, 9H).

6. Synthesis of C31-8

Compound C31-7 (575 mg, 1.89 mmol) was dissolved in dry tetrahydrofuran (30 mL), cooled to −78° C., and 1M L-selectride in tetrahydrofuran (5.7 mL, 5.66 mmol) was added dropwise under the protection of nitrogen, and stirred at −78° C. for 1 h. The reaction was monitored by TLC until it was completed, methanol was added dropwise to quench, then raised to room temperature, and diluted with ethyl acetate. Organic phase was washed with saturated brine, dried over anhydrous sodium sulfate, filtered, concentrated and purified by column chromatography to obtain 558 mg of compound C31-8.

Nuclear magnetic analysis data of compound C31-8: $^1$H NMR (400 MHz, DMSO-$d_6$) δ 8.48 (s, 1H), 8.09-8.04 (m, 2H), 7.69-7.66 (dd, 1H, J=8.12 Hz, 1.48 Hz), 4.60-4.57 (q, 1H), 4.10 (s, 3H), 1.53 (s, 3H), 1.15 (s, 9H).

7. Synthesis of C31-9

Compound C31-8 (498 mg, 1.62 mmol) was dissolved in a mixed solution of dioxane (3 mL) and anhydrous methanol (3 mL), then 4M hydrogen chloride in dioxane solution (4.1 mL) was added, and stirred at room temperature for 2 h. Then methyl tert-butyl ether was added, filtered and dried to obtain 295 mg of compound C31-9.

8. Synthesis of C31

Compound C31-9 (10 mg, 0.04 mmol) and compound C3-19 (16 mg, 0.04 mmol) were dissolved in DMF (0.5 ml), then diisopropylethylaamine (44 mg, 0.34 mmol) was added and stirred at room temperature for 5 min, then HATU (24 mg, 0.06 mmol) was added, and stirred at room temperature for 1 h. The reaction solution was diluted with ethyl acetate. Organic phase was washed with saturated brine, dried over anhydrous sodium sulfate, concentrated, and purified by Prep-HPLC to obtain 4 mg of compound C31. MS [M+H] 567.4.

Comparative Example 1

C32

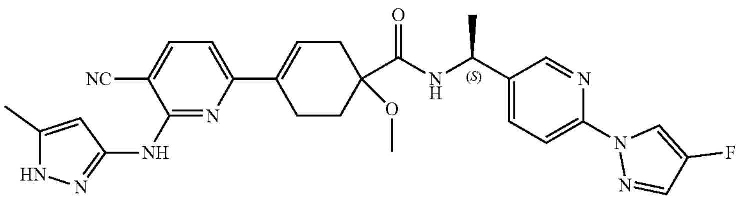

The synthetic route and experimental process were as follows:

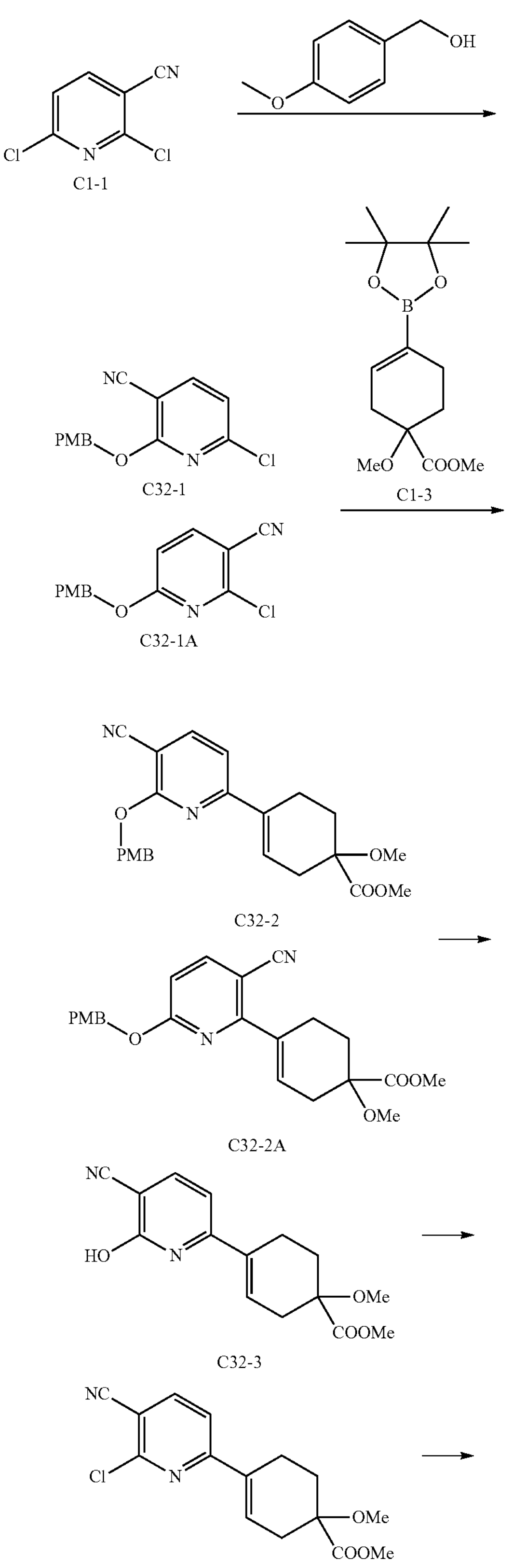

C1-1

C32-1

C1-3

C32-1A

C32-2

C32-2A

C32-3

C-32-4

-continued

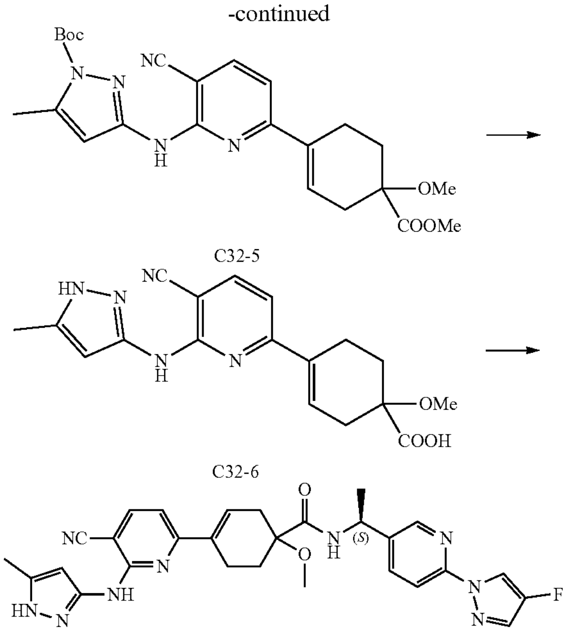

C32-5

C32-6

C32

1. Synthesis of C32-1 and C32-1A

C1-1 (6.92 g, 40 mmol), p-methoxybenzyl alcohol (6.07 g, 44 mmol), and THF (100 mL) were added in a 250 mL single-neck flask and NaH (2.4 g, 60 mmol) was added in batches at 0° C., and then reacted at room temperature for 4 h. LC-MS showed that the reaction was completed. The reaction solution was poured into water (200 mL) under stirring, extracted with ethyl acetate for three times, washed with saturated brine, dried over anhydrous sodium sulfate, concentrated, and purified by column chromatography to obtain 10.7 g (a mixture of C32-1 and C32-1A).

2. Synthesis of C32-2 and C32-2A

A mixture of C32-1 and C32-1A (8.22 g, 30 mmol), C1-3 (9.77 g, 33 mmol), $Pd(PPh_3)_4$ (3.47 g, 3 mmol), $K_2CO_3$ (8.28 g, 60 mmol) and dioxane/$H_2O$ (120 mL/30 mL) were added into a 250 mL single-neck flask to react at 90° C. overnight under the protection of $N_2$. LC-MS showed that the reaction was completed. The reaction solution was poured into water (300 mL) under stirring, extracted with ethyl acetate for three times, washed with saturated brine, dried over anhydrous sodium sulfate, evaporated, and purified by column chromatography to obtain C32-2A (4.78 g) and C32-2 (7.54 g).

Nuclear magnetic analysis data of compound C32-2A: 1H NMR (400 MHz, CDCl3) δ 7.76 (d, J=8.6 Hz, 1H), 7.37 (d, J=8.6 Hz, 2H), 6.94-6.86 (m, 2H), 6.67 (d, J=8.6 Hz, 1H), 6.58 (d, J=3.4 Hz, 1H), 5.35 (s, 2H), 3.81 (s, 6H), 3.34 (s, 3H), 2.90-2.56 (m, 4H), 2.28-2.06 (m, 2H);

Nuclear magnetic analysis data of compound C32-2: 1H NMR (400 MHz, CDCl3) δ 7.79 (d, J=7.9 Hz, 1H), 7.41 (d, J=8.7 Hz, 2H), 7.03 (d, J=7.9 Hz, 1H), 6.94-6.87 (m, 2H), 6.85 (dd, J=4.6, 3.3 Hz, 1H), 5.46 (s, 2H), 3.81 (d, J=1.4 Hz, 6H), 3.31 (s, 3H), 2.87-2.75 (m, 1H), 2.67-2.50 (m, 3H), 2.32-2.03 (m, 2H).

3. Synthesis of C32-3

C32-2 (1.0 g, 2.45 mmol), dichloromethane (6 mL) and trifluoroacetic acid (4 mL) were added into a 10 mL reactor to react at room temperature for 10 h, and evaporated. Then $K_2CO_3$(aq) was added, and extracted with ethyl acetate three times, washed with saturated brine, dried over anhydrous sodium sulfate, and concentrated to obtain a crude product (583 mg).

4. Synthesis of C32-4

C32-3 (703 mg, 2.4 mmol), toluene (5 mL) and $POCl_3$ (10 mL) were added into a 10 mL reactor to react at 110° C. for 10 h, then concentrated, and saturated $K_2CO_3$ aqueous solution was added. It was extracted with ethyl acetate for three times. Organic phase was washed with saturated brine, dried over anhydrous sodium sulfate, and concentrated under reduced pressure to obtain crude product (430 mg).

5. Synthesis of C32-5

C32-4 (320 mg, 1.05 mmol), C1-17 (227 mg, 1.15 mmol), $Pd_2(dba)_3$ (92 mg, 0.1 mmol), t-BuXPhos (89 mg, 0.21 mmol), KOAc (206 mg, 2.1 mmol) and dioxane (10 mL) were added into a 100 mL single-neck flask to react at 90° C. overnight under $N_2$ atmosphere. LC-MS showed that the reaction was completed, then it was concentrated under reduced pressure. Ethyl acetate was added to the residue, and the organic phase was washed with brine, dried and concentrated to obtain crude product. The crude product was purified by column chromatography to obtain 290 mg of product.

6. Synthesis of C32-6

C32-5 (1.81 g, 3.86 mmol), $LiOH \cdot H_2O$ (648 mg, 15.44 mmol) and $THF/MeOH/H_2O$ (10 mL/10 mL/5 mL) were added into a 50 mL single-neck flask to react at 50° C. for 2 h. LC-MS showed that the reaction was completed, and concentrated under reduced pressure to obtain 1.58 g of crude product.

7. Synthesis of C32

C32-6 (108 mg, 0.3 mmol), C1-7 (92 mg, 0.33 mmol), DMF (7 mL) and diisopropylethylamine (310 mg, 2.4 mmol) were added into a 50 mL single-neck flask, stirred for 5 min at room temperature, and then HATU (134 mg, 0.35 mmol) was added to react at room temperature for 30 min. LC-MS showed that the reaction was completed. The reaction solution was poured into water (20 mL), extracted with ethyl acetate for three times, washed with saturated brine, dried over anhydrous sodium sulfate, evaporated, and purified by column chromatography to obtain crude product. The crude product was separated by Prep-HPLC to obtain C32 (123 mg, purity: 95.7%), [M+H]: 542.3.

Nuclear magnetic analysis data of compound C32: 1H NMR (400 MHz, CDCl3) δ 8.47 (t, J=8.3 Hz, 1H), 8.38 (d, J=4.6 Hz, 2H), 7.92 (d, J=8.5 Hz, 1H), 7.78 (dd, J=8.5, 2.1 Hz, 1H), 7.59 (d, J=4.3 Hz, 1H), 7.25-7.15 (m, 1H), 6.91 (dd, J=7.9, 5.2 Hz, 1H), 6.73 (d, J=8.6 Hz, 1H), 5.86 (d, J=4.3 Hz, 1H), 5.19 (dd, J=9.8, 4.8 Hz, 1H), 3.26 (d, J=5.7 Hz, 3H), 3.08-2.44 (m, 4H), 2.40 (d, J=2.1 Hz, 3H), 2.19-2.01 (m, 2H), 1.60 (d, J=7.0 Hz, 3H).

Test Example 1 Enzyme Activity Test

A biological activity test experiment was conducted below for some compounds of the above Examples and Comparative Example.

The experimental process of biological activity test was as follows:

The activity of the compounds prepared in Examples against wild-type RET kinase was screened using the Kinase activity Assay method at ATP Km concentration, and staurosporine was used as a reference substance. The biological activity screening of the compounds will be determined repeatedly at 10 concentrations.

1. Sample to be Tested

Each sample was prepared into a solution with a concentration of 10 mM.

2. Experimental Method

I. Preparing Basic Buffer Solution and Quenching Buffer Solution for Experimental Kinase 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO.

II. Preparing Compounds for Experimental Kinase

The test compound was dissolved in 100% dimethyl sulfoxide to a specific concentration. Integra Viaflo Assist was used to assist DMSO for (continuous) dilution.

III. Reaction Steps

Kinase was added to the newly prepared basic reaction buffer

Adding any desired cofactors to the substrate solution.

Adding wild-type RET kinase into the substrate solution and gently mixing;

Acoustic technology (Echo 550; Nanoliter range) was used to feed the compounds in 100% of dimethyl sulfoxide into the kinase reaction mixture and incubated at room temperature for 20 minutes.

33P-ATP (specific activity 10 Ci/l) was added to the reaction mixture to start the reaction.

Incubated at room temperature for 2 hours

Radioactivity was detected by filter-binding method.

Kinase activity data was expressed as the percentage of remaining kinase activity in the test sample compared to the vehicle (dimethyl sulfoxide) reaction. Prism (GRAPHPAD software) was used to obtain IC50 value and curve-fitting.

The inhibitory activity IC50 (nM) values of the obtained samples against wild-type RET were shown in Table 1.

TABLE 1

| Compound | Wild-RET IC50 (nM) |
|---|---|
| Staurosporine | 2.53 |
| C1 | 146 |
| C2 | 1.98 |
| C3 | 241 |
| C4 | 1.02 |
| C5 | 100 |
| C6 | 3.53 |
| C7 | 5.34 |
| C8 | 1.53 |
| C9 | 3.38 |
| C10 | 262 |
| C11 | 17.4 |
| C12 | 16.1 |
| C13 | 2.08 |
| C16 | 180 |
| C17 | 1.26 |
| C18 | 1.52 |
| C19 | 64.7 |
| Comparative Example C32 | no activity |

It can be seen from the above table that the compounds synthesized in the present application have good inhibitory ability against wild-type RET kinase through in vitro biological activity screening compared to the reference substance Staurosporine, and the compounds are expected to be further developed into medicaments for regulating RET kinase activity or treating RET-related disease. And from the activity data of C7 and Comparative Example C32, it can be seen that the position of the cyano of the compound has a great influence on the inhibitory activity of the compound against wild-type RET.

Test Example 2 Experiment of Cell Anti-Proliferation

I. Experimental Materials

RPMI-1640 was purchased from BI.

Fetal bovine serum was purchased from BI.

CellTiter-Glo® was purchased from Promega.

Dimethyl Sulfoxide (DMSO) was purchased from TCI.

BaF3 cells were purchased from RIKEN BRC CELL BANK.

Ba/F3-KIF5B-RET, Ba/F3-KIF5B-RET-V804L and Ba/F3-KIF5B-RET-V804M cells were constructed by PreceDo Pharmaceuticals Co., Ltd.

Ba/F3-KIF5B-RET, Ba/F3-KIF5B-RET-V804L and Ba/F3-KIF5B-RET-V804M medium: RPMI-1640+10% FBS+1% P/S.

Board reading instrument: Molecular Devices

II. Experimental Method

1. Dilution of Compounds

A 1000× solution of the compound was prepared with DMSO, the compound was diluted to 20 times final concentration with a growth medium, and 2 μl 1000×cpd 98 μl growth medium was added.

2. Cell Inoculation

The suspended cells were rotated downward, resuscitated in the growth medium, and then counted with a cell counter. The cell suspension was diluted to the desired concentration in the growth medium. 95p L cell suspension was fed to a 96-well plate. 5 μL of 20× compound was added to the 95-well plate, and the final DMSO concentration per well was 0.1%; incubated at 37° C. with 5% CO2 for 72 h 3. Measurement The plate was equilibrated to room temperature before measurement, 50 μl of CellTiter-Glo® reagent was added into each well, mixed on a shaker for 2 minutes, incubated at room temperature for 10 minutes, and recorded with Paradigm.

III. Data Analysis

Cell viability was analyzed using Graphpad 7.0 software according to the formula Cell viability (CV %)=(RLU compound−RLU blank)/(RLU control−RLU blank)*100%, and the corresponding IC50 data were calculated as shown in Table 2

TABLE 2

| Compound | Ba/F3-KIF5B-RET (nM) | Ba/F3-KIF5B-RET-V804L (nM) | Ba/F3-KIF5B-RET-V804M (nM) |
|---|---|---|---|
| C2 | 23.1 | 16.9 | 42.4 |
| C4 | 9.1 | 7.1 | 17.3 |
| C14 | 54.1 | 46.8 | 108.8 |
| C15 | 4.6 | 2.8 | 7.4 |
| C24 | 95.11 | 84.03 | 181.7 |
| C26 | 5.2 | 2.9 | 7.9 |
| C27 | 29.4 | 23 | 51.9 |
| C29 | 145.5 | 118.2 | 252 |

It can be seen from Table 2 that the compounds of the present invention have better inhibitory effect on Ba/F3 (WT-RET, RET-V804L and RET-V804M), especially compounds C15 and C26.

Test Example 3 Metabolism Test of Drugs

Four small molecule compounds of BLU-667, compound C2, compound C4 and compound C8 were administered to SD rats by intravenous and intragastric administration respectively. Blood samples were collected at different time points to determine the concentration of drugs in plasma after administration and calculate the related pharmacokinetics parameters.

1. Preparation of Sample Solution

The preparation of the drug delivery solution of the sample for test was completed in College of Pharmaceutical Sciences, Soochow University. The preparation method was as follows:

The vehicle of BLU-667, C2, C4 and C8 was 10% NMP+49% PEG400+1% Tween80+40% Water. The specific preparation method was as follows: proper amount of tested samples was weighed, dissolved in 10% NMP+49% PEG400+1% Tween80+40% Water, mixed well by vortex for later use.

2. Analysis of Solution of Sample for Test

LC-MS/MS was used by the analysis department of the experimental organization to detect and analyze the prepared solution of sample for test.

3. Animal Reception and Adaptation

Healthy male SD rats were used in this research. Animal weight: 150-200 g. All animals fasted before administration, and resumed feeding 4 hours after administration.

4. Animal Administration

The administration information was shown in Table 3

TABLE 3

| Group | Sample for test | Number of animals | Dosage (mg/kg) | Administration concentration (mg/mL) | Administration volume (mL/kg) | Route of administration | Sample type |
|---|---|---|---|---|---|---|---|
| 1 | BLU-667 | 3 | 2 | 0.4 | 5 | IV | Plasma |
| 2 | BLU-667 | 3 | 10 | 1 | 10 | PO | Plasma |
| 3 | C2 | 3 | 2 | 0.4 | 5 | IV | Plasma |
| 4 | C2 | 3 | 10 | 1 | 10 | PO | Plasma |
| 5 | C4 | 3 | 2 | 0.4 | 5 | IV | Plasma |
| 6 | C4 | 3 | 10 | 1 | 10 | PO | Plasma |
| 7 | C8 | 3 | 10 | 1 | 10 | PO | Plasma |

5. Sample Collection and Processing

Time points for blood collection were:

Intravenous administration (groups 1, 3 and 5): 0.0833, 0.25, 0.5, 1, 2, 4, 8, 12 and 24 hours after administration. (±2 min at time point ≤2 hr, ±15 min at other points.)

Oral administration: (groups 2, 4, 6 and 7): 0.25, 0.5, 1, 2, 4, 8, 12 and 24 hours after administration. (±2 m at time point 2 hr, ≤15 mi at other points.)

About 0.1 mL of blood was collected from each animal through jugular vein every time, and EDTA or heparin sodium was used as anticoagulant. Blood samples were collected and placed on ice, and plasma was separated by centrifugation (centrifugation conditions: 5000 r/min, 6 min, 4° C.).

LC-MS/MS was used by the analysis department of the experimental organization to analyze the plasma samples of rats.

6. Pharmacokinetic Analysis

According to the data of blood drug concentration of the drug, the pharmacokinetic parameters $AUC_{0\rightarrow t}$, $AUC_{0\rightarrow\infty}$, $MRT_{0\rightarrow\infty}$, $C_{Max}$, $T_{Max}$, Vss, F, CL and $T_{1/2}$ as well as their mean and standard deviation of the samples for test were calculated respectively by pharmacokinetic calculation software WinNonlin non-compartment model.

7. Experimental Results

The main pharmacokinetic parameters of BLU-667, compound C2, compound C4 and compound C8 in plasma after intravenous and single oral administration of BLU-667, compound C2, compound C4 and compound C8 in SD rats were shown in Table 3

TABLE 3

| Compound for test | BLU-667 | | C4 | | C2 | | C8 |
|---|---|---|---|---|---|---|---|
| Route of administration | IV | PO | IV | PO | IV | PO | PO |
| Dosage (mg/kg) | 2 | 10 | 2 | 10 | 2 | 10 | 10 |
| $T_{Max}$ (hr) | / | 4 | / | 2 | / | 2 | 2 |
| $C_{Max}$ (ng/mL) | / | 632.33 | / | 2460.00 | / | 324.67 | 823.67 |
| $AUC_{0-last}$ (ng/mL * hr) | 1334.40 | 4079.46 | 4386.38 | 10933.81 | 3851.63 | 2302.66 | 2804.61 |
| $AUC_{INF}$ (ng/mL * hr) | 1406.66 | 4111.44 | 4428.12 | 10972.55 | 3902.71 | 2321.24 | 2831.17 |
| $t_{1/2}$ (hr) | 5.52 | 3.36 | 4.19 | 3.18 | 4.12 | 3.26 | 1.95 |
| $MRT_{INF\_}$ obs (hr) | 6.10 | 5.08 | 3.74 | 4.30 | 4.89 | 6.05 | 2.85 |
| CL_obs (L/hr/kg) | 1.47 | / | 0.46 | / | 0.52 | / | / |
| Vss (L/kg) | 8.53 | / | 1.70 | / | 2.56 | / | / |
| F (%) | 61.14 | | 49.85 | | 11.96 | | / |

It can be seen from Table 3 that the compounds of the present application have good pharmacokinetic properties, especially the compound C4 whose maximum blood drug concentration (Cmax) and plasma exposure amount AUC increased by 3-4 times and 2-3 times respectively compared with the control compound. Therefore, the compounds of the present invention have better bioavailability and are expected to be further developed into a medicament for regulating RET kinase activity or treating RET-related diseases.

The above description is only examples of the present invention, and does not limit the patent scope of the present invention. Any equivalent modifications made by using the contents of the present specification or directly or indirectly applied to other related technical fields are included in the scope of the present invention.

The invention claimed is:

1. A compound, or a pharmaceutically acceptable salt, stereoisomer, or solvate thereof has a structure represented by Formula 6',

6'

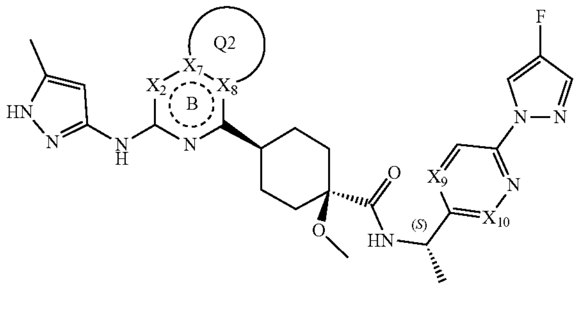

wherein $X_2$, $X_9$, and $X_{10}$ are each independently selected from N or $CR_5$;

$X_7$ and $X_8$ are each independently selected from N or C; and $R_5$ is each independently selected from hydrogen, C1-C6 alkyl, C2-C6 alkenyl, C2-C6 alkynyl, C1-C6 alkoxy, C1-C6 alkylamino, halogen, C1-C6 heteroalkyl, cycloalkyl, nitro, cyano, or amino; wherein alkyl, alkenyl, alkynyl, alkoxy, alkylamino, heteroalkyl, and cycloalkyl are each independently substituted by 0-5 $R^a$; $R^a$ is selected from C1-C6 alkyl, halogen, hydroxy, C1-C6 heteroalkyl, C1-C6 alkoxy, C1-C6 alkylamino, cycloalkyl, heterocycloalkyl, or cyano;

ring Q2 is selected from five-membered, six-membered or seven-membered saturated ring, unsaturated ring, aromatic ring, or heteroaromatic ring, and can contain 0-3 heteroatoms selected from N, O, or S, and any hydrogen atom on the ring Q2 can be substituted by deuterium, hydroxy, halogen, cyano, ester, amide, ketocarbonyl, amino, C1-C6 alkyl, C1-C6 haloalkyl, C1-C6 thioalkyl, C1-C6 alkoxy, C1-C6 heteroalkyl, C1-C6 alkylamino, C3-C6 cycloalkyl, C3-C8 cycloalkylamino, aryl, or heteroaryl.

2. A compound, or a pharmaceutically acceptable salt, stereoisomer, or solvate thereof, wherein the compound is selected from the following compounds:

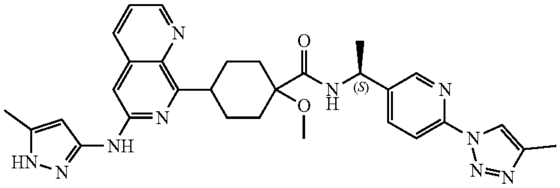
,

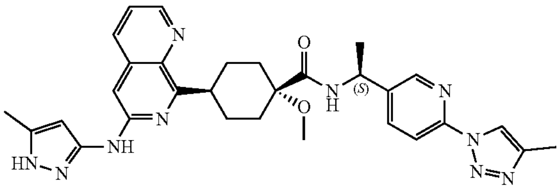
,

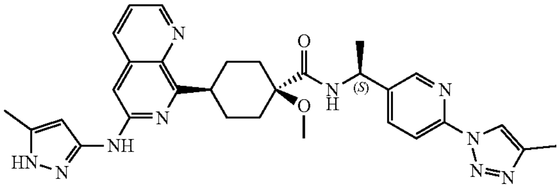
,

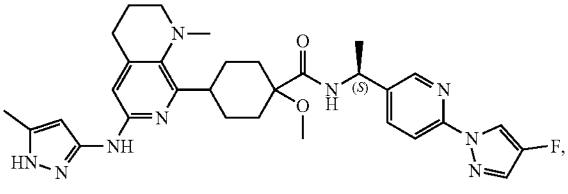
F,

-continued
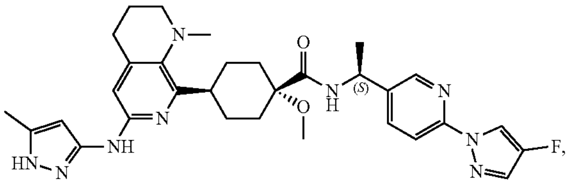
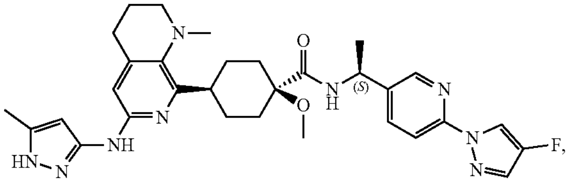
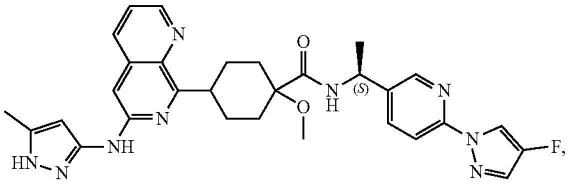
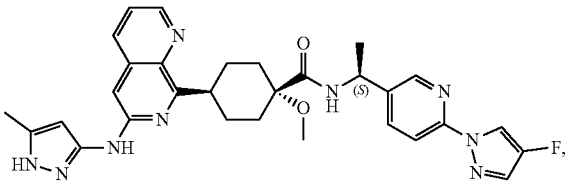
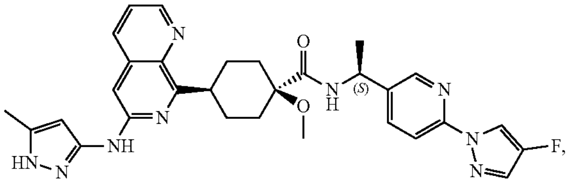
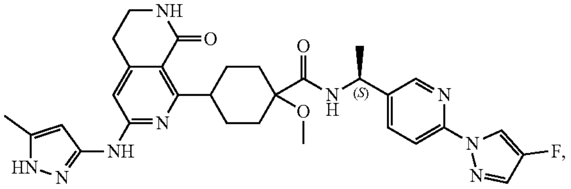
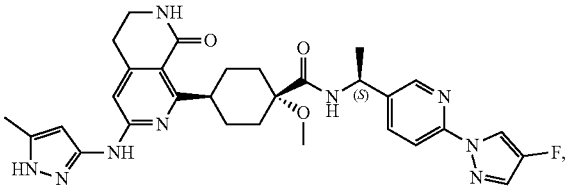
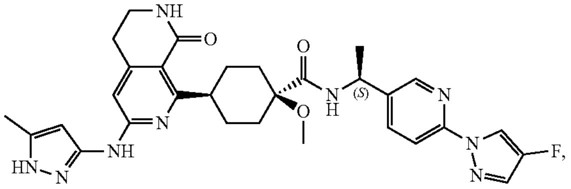
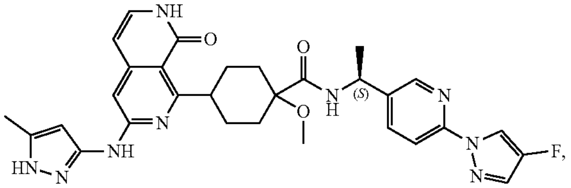
-continued
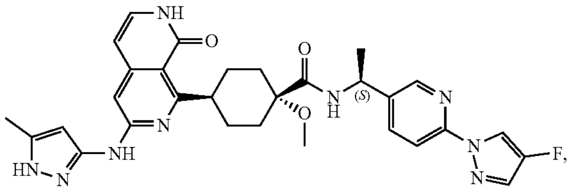
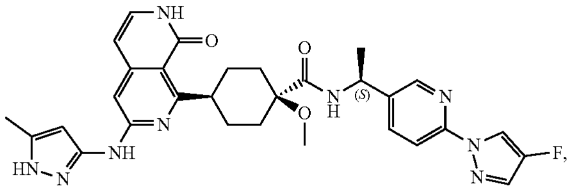
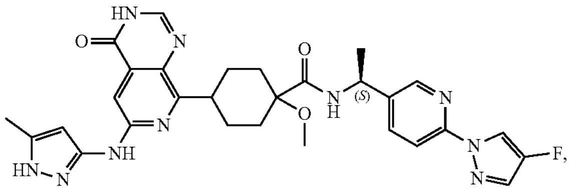
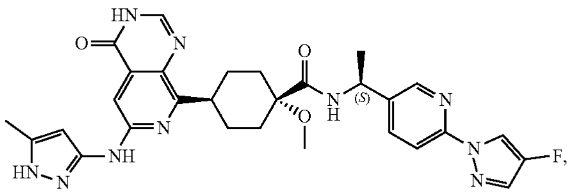
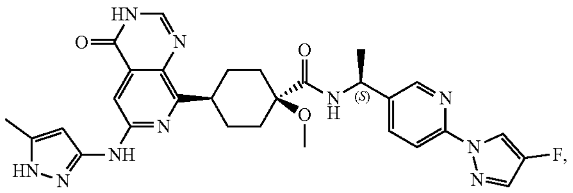
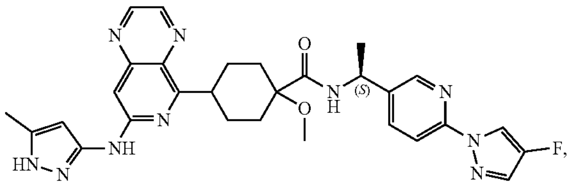
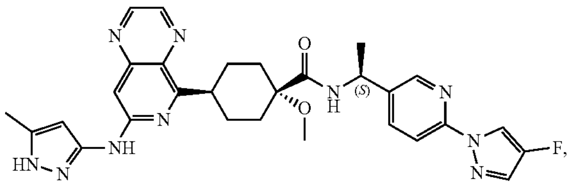
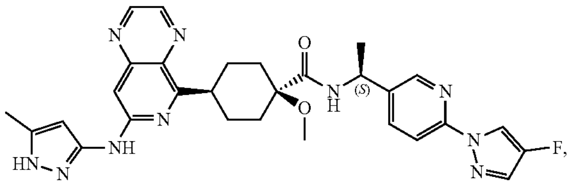
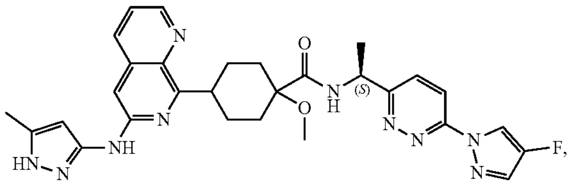

-continued
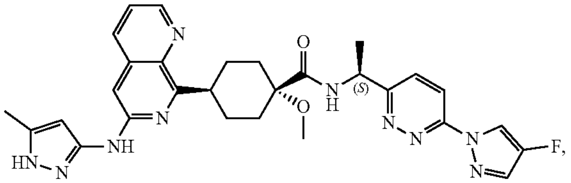
,
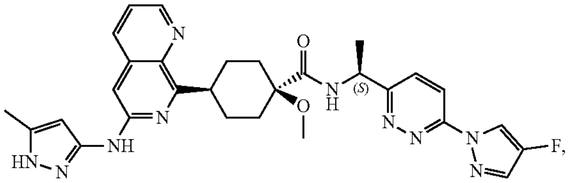
,
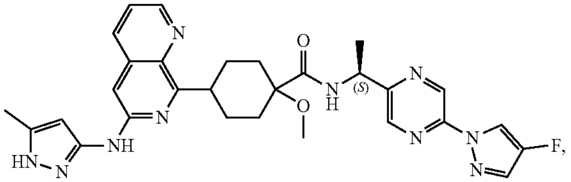
,
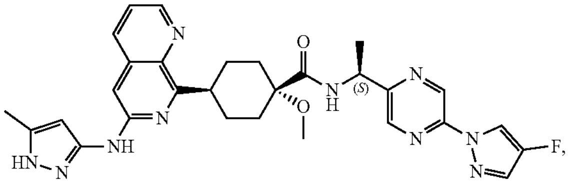
,
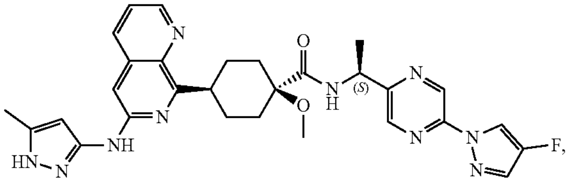
,
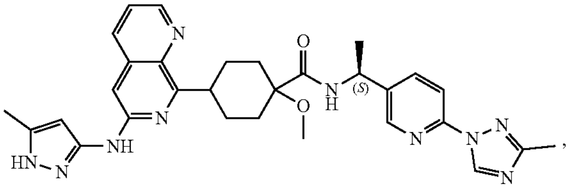
,
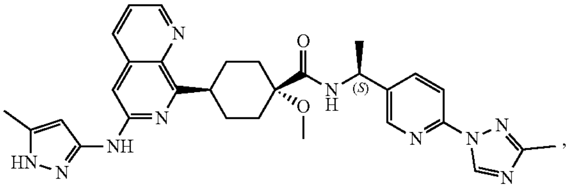
,
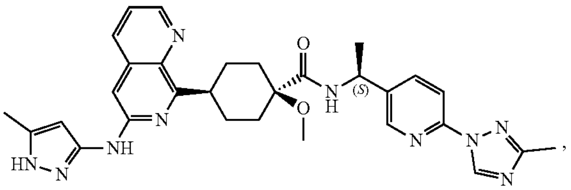
,
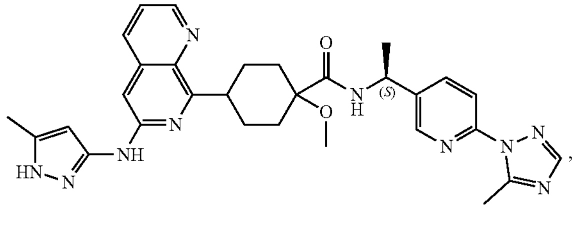
,
-continued
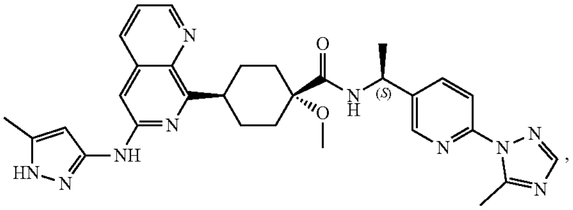
,
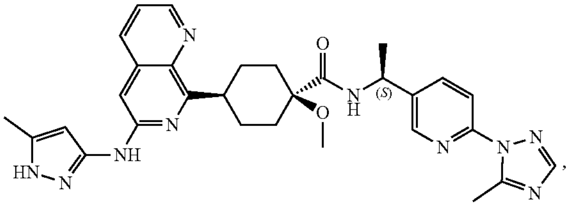
,
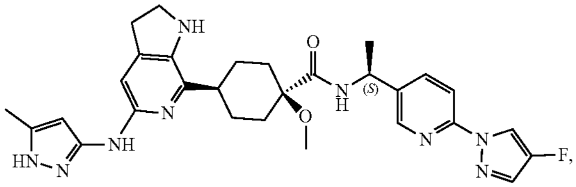
,
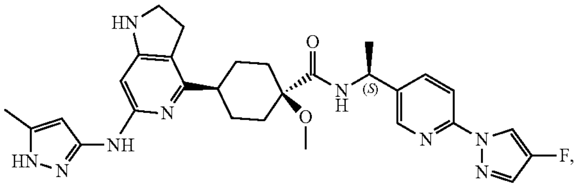
,
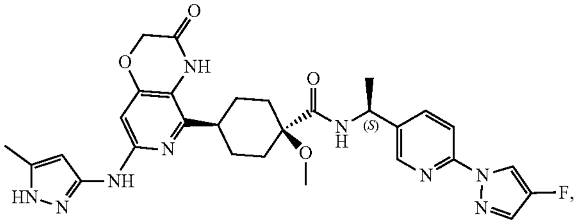
,
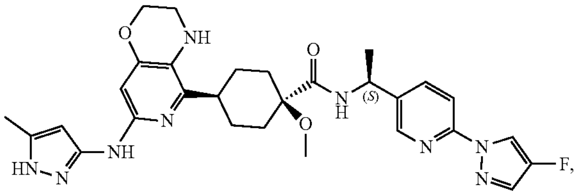
,
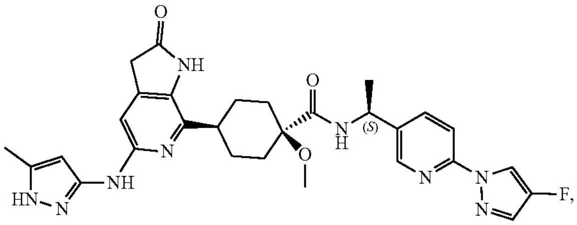
,
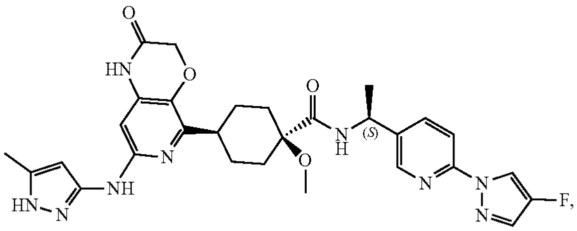
, -continued
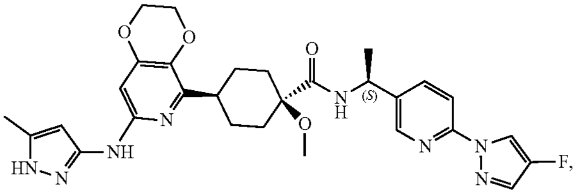
,
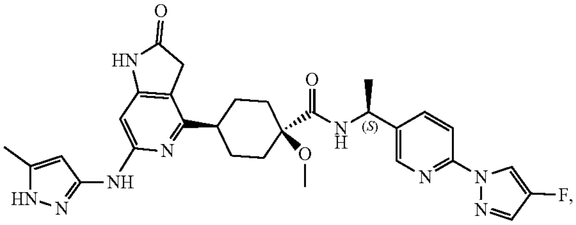
,
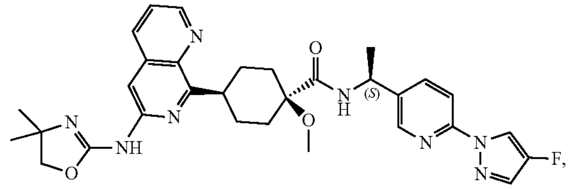
,
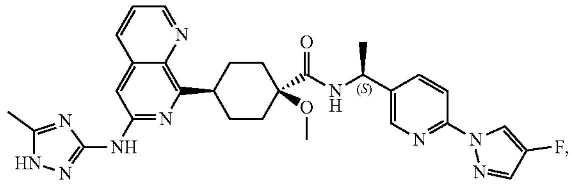
,
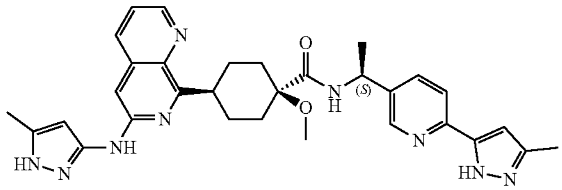
,
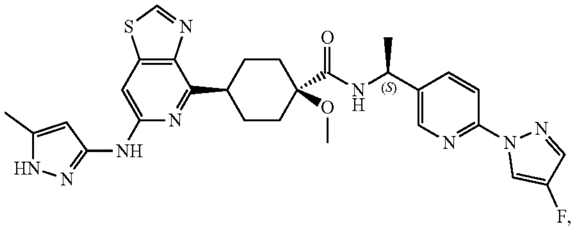
,
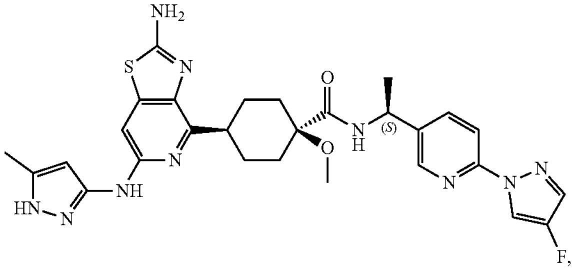
,
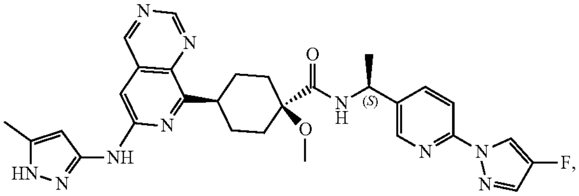
,
-continued
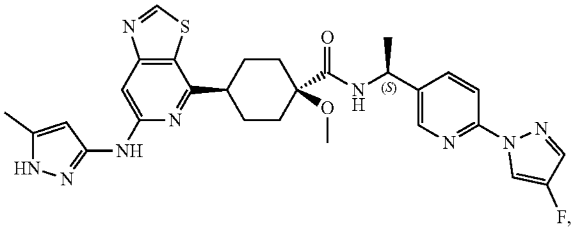
,
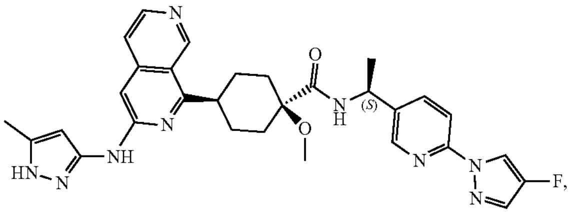
,
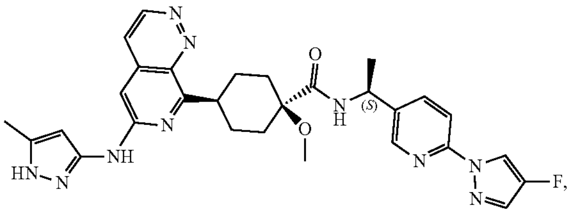
,
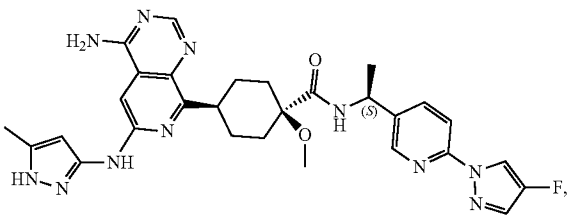
,
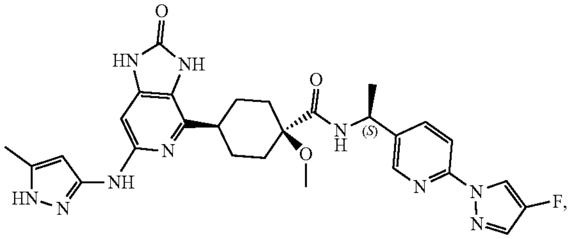
,
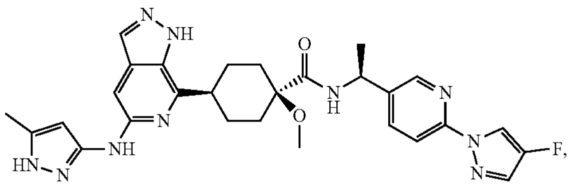
,
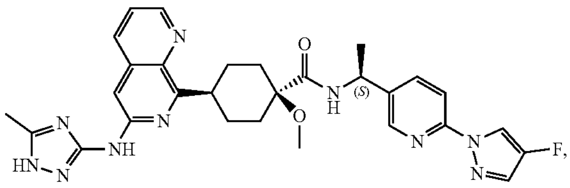
,
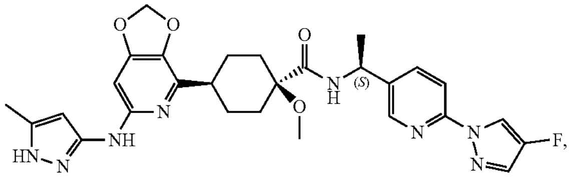
, -continued
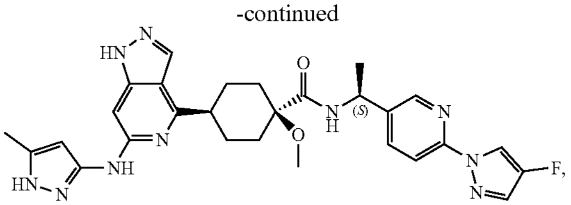
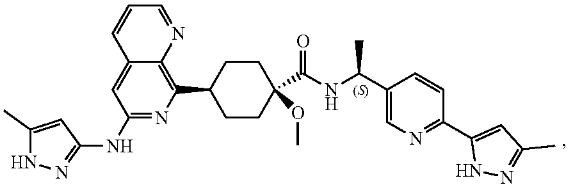
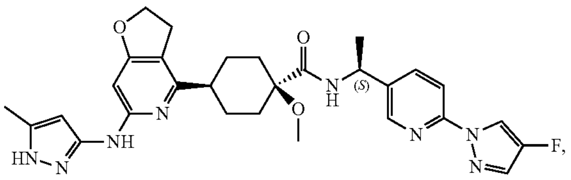
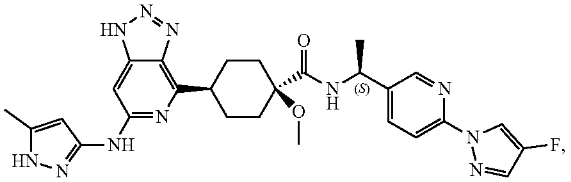
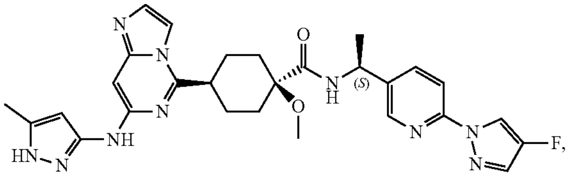
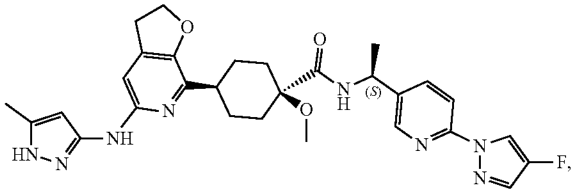
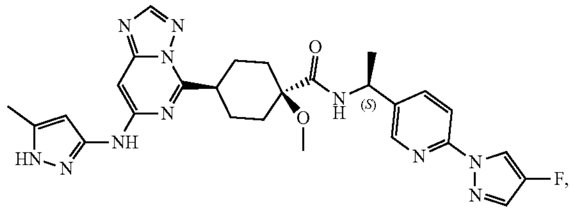
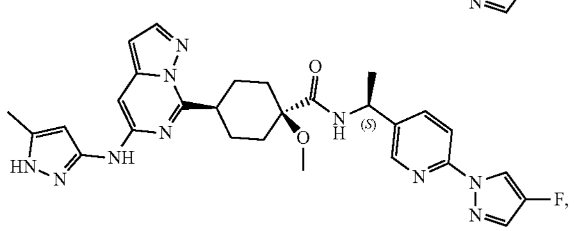
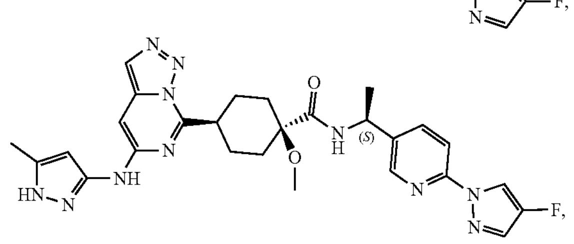
-continued
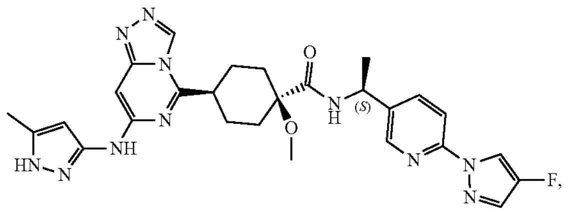
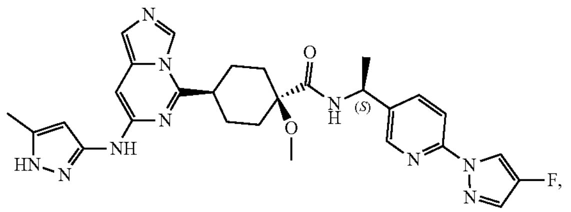
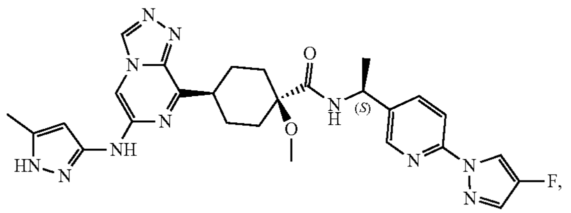
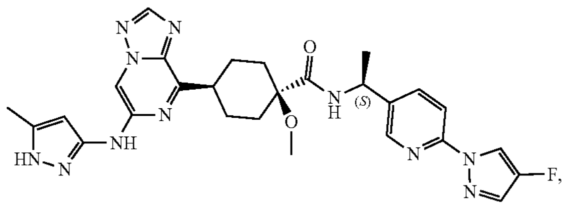
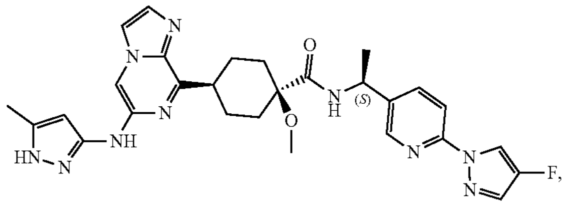
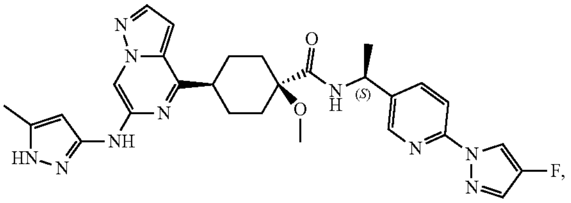
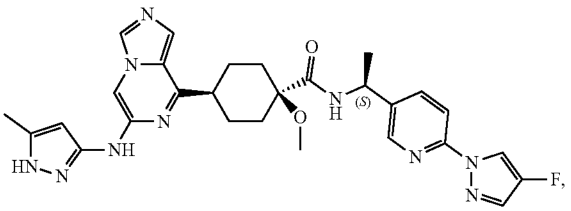
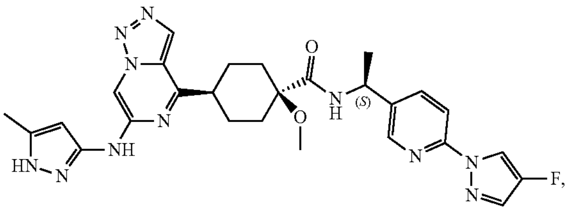

-continued

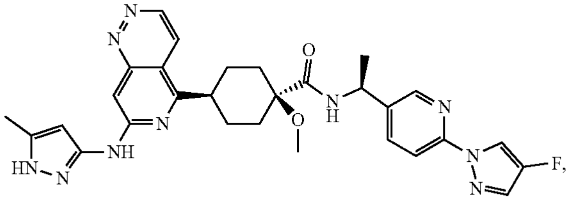

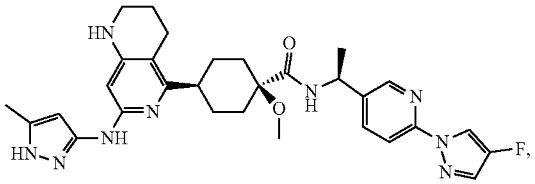

and

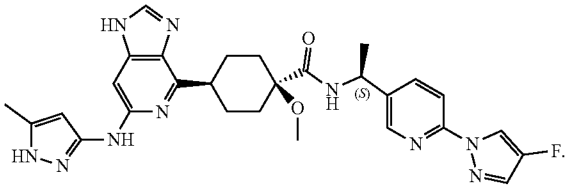

3. The compound of claim 1, or the pharmaceutically acceptable salt, stereoisomer, or solvate thereof, wherein the pharmaceutically acceptable salt is an inorganic acid salt or an organic acid salt, wherein the inorganic acid salt is selected from hydrochloride, hydrobromide, hydroiodide, sulfate, bisulfate, nitrate, phosphate, or acid phosphate; the organic acid salt is selected from formate, acetate, trifluoroacetate, propionate, pyruvate, hydroxyacetate, oxalate, malonate, fumarate, maleate, lactate, malate, citrate, tartrate, methanesulfonate, ethanesulfonate, benzenesulfonate, salicylate, picrate, glutamate, ascorbate, camphorate, or camphor sulfonate.

4. A pharmaceutical composition comprising a therapeutically effective amount of the compound of claim 1, or the pharmaceutically acceptable salt, stereoisomer, or solvate thereof, and a pharmaceutically acceptable carrier.

5. A method of modulating RET kinase activity or treating RET-related diseases comprising administering to a subject in need thereof an effective amount of the compound of claim 1, or the pharmaceutically acceptable salt, stereoisomer, or solvate thereof.

6. The method of claim 5, wherein the RET-related diseases comprise a cancer.

7. The compound of claim 1, or the pharmaceutically acceptable salt, stereoisomer, or solvate thereof, wherein

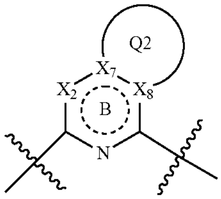

is selected from

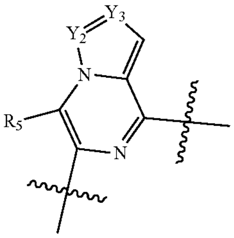,

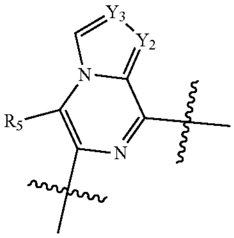,

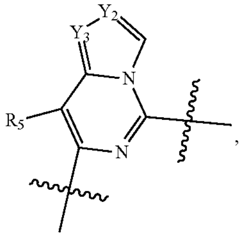, or

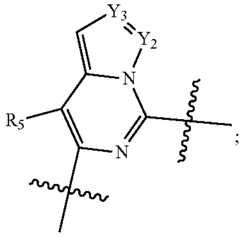;

$R_5$ is independently selected from H, halogen, C1-C6 alkyl, C1-C6 alkoxy, C1-C6 alkylamino, nitro, cyano, or amino;

$Y_2$ and $Y_3$ are each independently selected from O, N, and $CR_{13}$;

$R_{13}$ is each independently selected from H, halogen, C1-C6 alkyl, C1-C6 alkoxy, C1-C6 alkylamino, cyano, or amino.

8. A pharmaceutical composition, wherein the pharmaceutical composition comprises a therapeutically effective amount of the compound of claim 2, or the pharmaceutically acceptable salt, stereoisomer, or solvate thereof, and a pharmaceutically acceptable carrier.

9. A method of modulating RET kinase activity or treating RET-related diseases comprising administering to a subject in need thereof an effective amount of the compound of claim 2, or the pharmaceutically acceptable salt, stereoisomer, or solvate thereof.

10. The method of claim 9, wherein the RET-related diseases comprise a cancer.

* * * * *